United States Patent [19]

Ohta et al.

[11] Patent Number: 5,457,154
[45] Date of Patent: Oct. 10, 1995

[54] BISIMIDE COMPOUNDS, POLYIMIDE RESIN COMPOSITION PREPARED THEREFROM, AND CARBON FIBER-REINFORCED POLYIMIDE RESIN COMPOSITION

[75] Inventors: Masahiro Ohta; Akio Matsuyama; Eiji Senoue; Fumiaki Kuwano; Osamu Yasui; Yasunori Yoshida; Akinori Ryu, all of Fukuoka; Tadashi Kobayashi, Kanagawa, all of Japan

[73] Assignee: Mitsui Toatsu Chemicals, Inc., Tokyo, Japan

[21] Appl. No.: 934,681

[22] PCT Filed: Jan. 20, 1992

[86] PCT No.: PCT/JP92/00039

§ 371 Date: Sep. 11, 1992

§ 102(e) Date: Nov. 9, 1992

[87] PCT Pub. No.: WO92/12967

PCT Pub. Date: Aug. 6, 1992

[30] Foreign Application Priority Data

| Jan. 21, 1991 | [JP] | Japan | 3-004963 |
| Feb. 19, 1991 | [JP] | Japan | 3-024303 |
| Feb. 20, 1991 | [JP] | Japan | 3-025932 |
| Mar. 26, 1991 | [JP] | Japan | 3-061685 |
| Apr. 18, 1991 | [JP] | Japan | 3-086558 |
| Jun. 27, 1991 | [JP] | Japan | 3-156792 |
| Jul. 1, 1991 | [JP] | Japan | 3-160211 |
| Aug. 29, 1991 | [JP] | Japan | 3-218286 |
| Sep. 11, 1991 | [JP] | Japan | 3-231295 |
| Sep. 11, 1991 | [JP] | Japan | 3-231296 |
| Oct. 29, 1991 | [JP] | Japan | 3-282849 |
| Nov. 1, 1991 | [JP] | Japan | 3-287660 |
| Nov. 1, 1991 | [JP] | Japan | 3-287661 |

[51] Int. Cl.⁶ ................................ C08G 73/10
[52] U.S. Cl. ............. 524/600; 524/602; 524/606; 524/607; 525/436; 528/125; 528/128; 528/170; 528/171; 528/172; 528/173; 528/176; 528/185; 528/188; 528/220; 528/229; 528/350; 528/353
[58] Field of Search ............... 525/436; 524/600, 524/602, 607, 606; 528/353, 170, 171, 173, 172, 176, 220, 185, 229, 188, 350, 125, 128

[56] References Cited

U.S. PATENT DOCUMENTS

| 4,024,110 | 5/1977 | Takekoshi | 528/353 |
| 4,847,349 | 7/1989 | Ohta et al. | 528/172 |
| 4,937,316 | 6/1990 | Ohta et al. | 528/353 |
| 4,987,197 | 1/1991 | Ohta et al. | 528/353 |
| 5,041,520 | 8/1991 | Ohta et al. | 528/353 |
| 5,196,506 | 3/1993 | Tamai et al. | 528/353 |
| 5,210,174 | 5/1993 | Tamai et al. | 528/353 |
| 5,243,024 | 9/1993 | Bockrath et al. | 528/353 |
| 5,272,248 | 12/1993 | Pratt et al. | 528/353 |

FOREIGN PATENT DOCUMENTS

| 319916 | 6/1989 | European Pat. Off. . |
| 372935 | 6/1990 | European Pat. Off. . |
| 53-106752 | 9/1978 | Japan . |
| 56-120730 | 9/1981 | Japan . |
| 59-147046 | 8/1984 | Japan . |
| 2-018419 | 1/1990 | Japan . |
| 3-192120 | 8/1991 | Japan . |
| 3-259914 | 11/1991 | Japan . |

*Primary Examiner*—Samuel A. Acquah
*Assistant Examiner*—P. Hampton-Hightower
*Attorney, Agent, or Firm*—Burns, Doane, Swecker & Mathis

[57] ABSTRACT

A moldable polyimide resin composition which has melt-flowability and excellent processability in addition to essential heat-resistant of polyimide and comprises an aromatic bisimide compound and polyimide resin. A further aspect relates to a carbon fiber reinforced polyimide resin composition which has excellent mechanical strengths and comprises a carbon fiber coated with aromatic bisimide compound on the surface and the polyimide resin. A still further aspect relates to a novel bisimide compound which is very useful as the aromatic bisimide compound in the composition.

22 Claims, 5 Drawing Sheets

BISIMIDE COMPOUNDS, POLYIMIDE RESIN COMPOSITION PREPARED THEREFROM, AND CARBON FIBER-REINFORCED POLYIMIDE RESIN COMPOSITION

BACKGROUND OF THE INVENTION

The present invention relates to a bisimide compound, a polyimide resin composition comprising the bisimide compound, and a carbon fiber reinforced polyimide composition comprising a carbon fiber coated on the surface with the bisimide compound.

DESCRIPTION OF THE RELATED ART

Materials having more excellent high-temperature characteristics have recently been required in order to enhance performance and reduce weight on various industrial materials in the fields of electric and electronic devices, space and aeronautical equipment and transport machinery. In these materials, polyimide has mechanical strength, dimensional stability, flame retardance and electrical insulation properties in addition to its excellent high-temperature resistance, and has hence been widely used in the above industrial fields. Polyimide of high molecular weight, however, generally has a high softening point and is insoluble in almost organic solvents. As a result, many difficulties have been encountered for the use of polyimide.

ULTEM(Trade mark of General Electric Co.), a representative thermoplastic polyimide resin, has superior heat resistance and mechanical strength compared to general purpose engineering plastics. Consequently, it is called a super engineering plastic and widely investigated for use in electric and electronical devices, machines. and automobiles.

Accompanied with the recent progress of technology, it has been demanded to develop a novel thermoplastic polyimide resin having heat-resistance and mechanical characteristics which are superior to ULTEM.

For example, U.S. Pat. No. 4,847,349 discloses a process for preparing polyimide resin by reacting etherdiamine with tetracarboxylic acid dianhydride. Japanese Laid-Open Patent Hei 2-018419 proposes a process for preparing polyimide resin by reacting 3,3'-diaminobenzophenone and tetracarboxylic acid dianhydride. Both patents have provided novel polyimides having heat resistance and mechanical characteristics which are superior to conventional polyimide.

The above polyimides are much superior in heat resistance and other characteristics to common engineering plastics represented by polyethylene terephthalate, polybutylene terephthalate, polyether sulfone, polysulfone and polyphenylene sulfide. However, increased molecular weight lowers melt flowability and melt processability of the polyimide is still inferior to these engineering plastics.

In order to enhance the characteristics of polyimide resin, mechanical strength in particular, fibrous reinforcement, particularly carbon fiber, is generally incorporated.

Carbon fiber is frequently used for carbon fiber reinforced plastics which use epoxy resin as a matrix and hence epoxy resin is commonly used for the collecting agent of carbon fiber. As a result, the epoxy resin collecting agent is effective when thermosetting resin such as epoxy resin is used for the matrix. However, epoxy resin has poor adhesion to polyimide resin and a resin composition having good mechanical strength cannot be obtained.

A process of using polyimide resin for the collecting agent of carbon fiber has been disclosed, for example, in Japanese Laid-Open Patent Sho 53-106752. However, polyimide resin must be generally processed at temperatures higher than 300° C. and the collecting agent decomposes by heat in the processing step to cause problems such as formation of voids and reduction of weld strength. Further, Japanese Laid-Open Patent Sho 56-120730 describes a process for using a carbon fiber collected with aromatic polysulfone resin. However, the process leads to merely a small increase in mechanical strengths and has not yet fully satisfied desired characteristics.

An object of the invention is to provide a compound having outstanding processability in addition to excellent heat resistance.

Another object of the invention is to provide a processable polyimide-based resin composition having very excellent melt flowability without impairing the essential characteristics of polyimide.

A further object of the present invention is to provide a polyimide-based resin composition having excellent mechanical strength.

SUMMARY OF THE INVENTION

As a result of an intensive investigation in order to accomplish the above objects, the present inventors have found that a polyimide resin composition comprising an aromatic bisiide compound is excellent in melt flowability and processability and that a polyimide resin composition comprising a carbon fiber coated with the aromatic bisimide compound on the surface has excellent mechanical strength, and further have found a novel bisimide compound which is very useful for the composition. Thus, the present invention has been completed.

That is, one aspect of the invention is a bisimide compound represented by the formula(1):

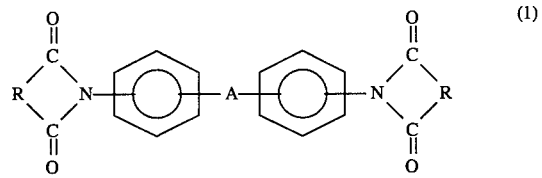

wherein A is a divalent radical selected from the group consisting of radicals having the formulas:

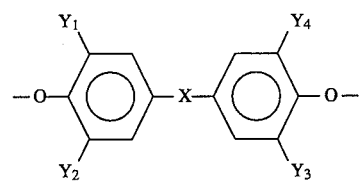

wherein X is a direct bond, a divalent hydrocarbon radical having from 1 to 10 carbon atoms, hexafluorinated isopropylidene, carbonyl, thio or sulfonyl, and $Y_1$–$Y_4Y$, are individually hydrogen atom, lower alkyl radical, lower alkoxy radical, chlorine or bromine atom,

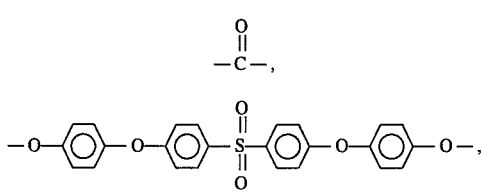

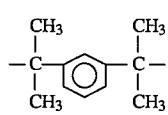

and

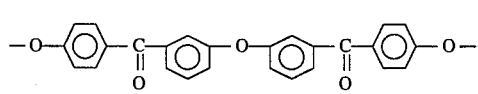

; and R is a divalent radical selected from the group consisting of a monoaromatic radical, condensed polyaromatic radical and noncondensed aromatic radical connected to each other with a direct bond or a bridge member.

Practical compounds are a bisimide compound represented by the formula(2):

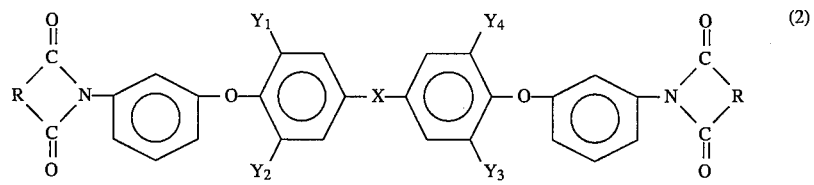

wherein X is a direct bond, a divalent hydrocarbon radical having from 1 to 10 carbon atoms, hexafluorinated isopropylidene, carbonyl, thio or sulfonyl, Y Y, are individually hydrogen, lower alkyl radical, lower alkoxy radical, chlorine or bromine atom, and R is a divalent radical selected from the group consisting of a monoaromatic radical, condensed polyaromatic radical and noncondensed aromatic radical connected to each other with a direct bond or a bridge member; a bisimide compound represented by the formula(3):

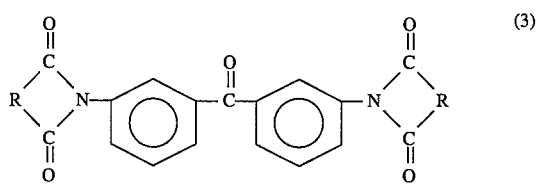

wherein R is a divalent radical selected from the group consisting of a monoaromatic radical, condensed polyaromatic radical and noncondensed aromatic radical connected each other with a direct bond or a bridge member; a bisimide compound represented by the formula(4):

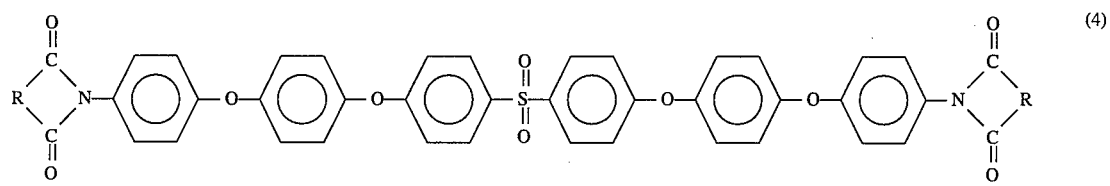

wherein R is a divalent radical selected from the group consisting of a monoaromatic radical, condensed polyaromatic radical and noncondensed aromatic radical connected to each other with a direct bond or a bridge member; a bisimide compound represented by the formula(5):

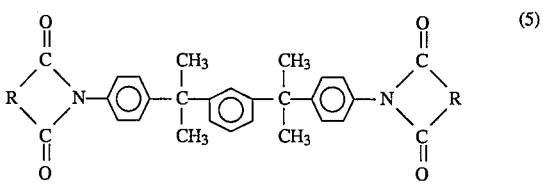

wherein R is a divalent radical selected from the group consisting of a monoaromatic radical, condensed polyaromatic radical and noncondensed aromatic radical connected to each other with a direct bond or a bridge member; a bisimide compound represented by the formula(6):

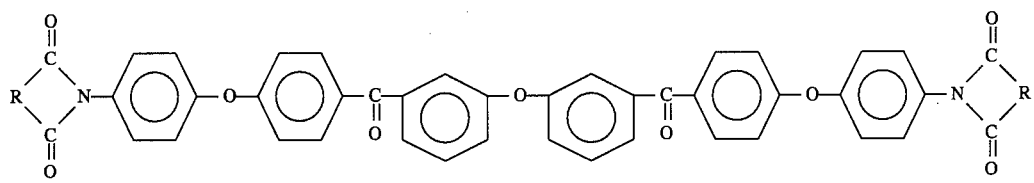

(6)

wherein R is a divalent radical selected from the group consisting of a monoaromatic radical, condensed polyaromatic radical and noncondensed aromatic radical connected each other with a direct bond or a bridge member; and a bisimide compound represented by the formula(7):

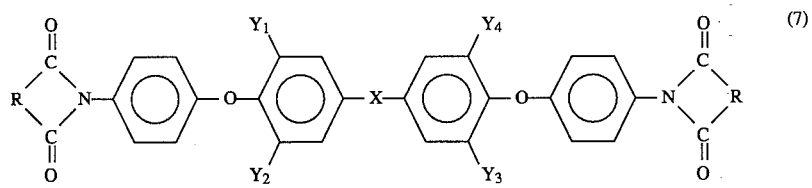

(7)

wherein X is a direct bond, a divalent hydrocarbon radical having from 1 to 10 carbon atoms, hexafluorinated isopropylidene, carbonyl, thio or sulfonyl, Y, Y, are individually hydrogen, lower alkyl radical, lower alkoxy radical, chlorine or bromine atom, and R is a divalent radical selected from the group consisting of a monoaromatic radical, condensed polyaromatic radical and noncondensed aromatic radical connected to each other with a direct bond or a bridge member.

Another aspect of the invention is a polyimide resin composition comprising the aromatic bisimide compound and polyimide, for example, a polyimide resin composition comprising as requisite components ① the bisimide compound represented by the above formula(1) and ② polyimide, particularly the polyimide having recurring structural units of the formula(8):

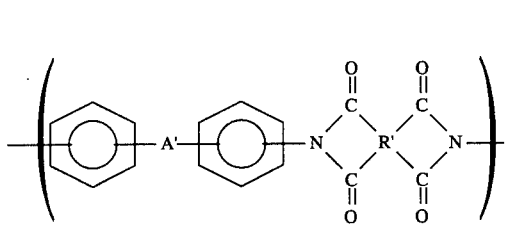

(8)

wherein A' is a divalent radical having the formula:

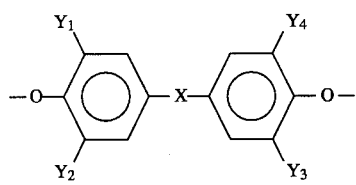

wherein X is a direct bond, a divalent hydrocarbon radical having from 1 to 10 carbon atoms, hexafluorinated isopropylidene, carbonyl, thio or sulfonyl, and $Y_1$-$Y_4$ are individually hydrogen atom, lower alkyl radical, lower alkoxy radical, chlorine or bromine atom; or the formula:

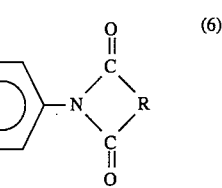

and R' is a tetravalent radical having 2 or more carbon atoms and selected from the group consisting of an aliphatic radical, alicyclic radical, monoaromatic radical, condensed polyaromatic radical and noncondensed aromatic radical connected to each other with a direct bond or a bridge member.

Following polyimide resin compositions are exemplified as preferred combinations of the aromatic bisimide compound and polyimide.

(1) A polyimide resin composition wherein the polyimide has recurring structural units represented by the formula(9):

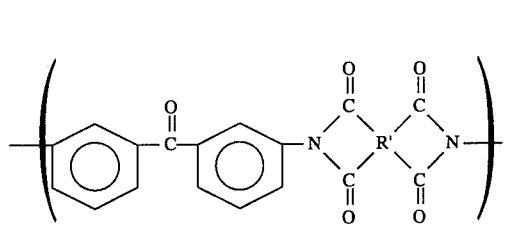

(9)

wherein R' is the same as in the formula(8) and the aromatic bisimide compound is represented by the formula(10):

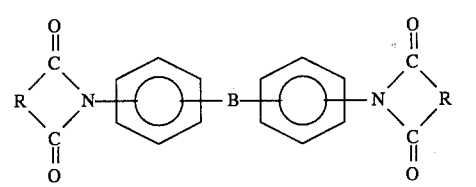

(10)

wherein B is a direct bond, a radical selected from divalent hydrocarbon radical having from 1 to 10 carbon atoms, hexafluorinated isopropylidene, carbonyl, thio, ether and sulfonyl, each nitrogen atom is individually para-, ortho- or meta-located to B and R is a divalent radical selected from the group consisting of a monoaromatic radical, condensed polyaromatic radical, noncondensed aromatic radical connected to each other with a direct bond or a bridge member, and/or by the formula(2):

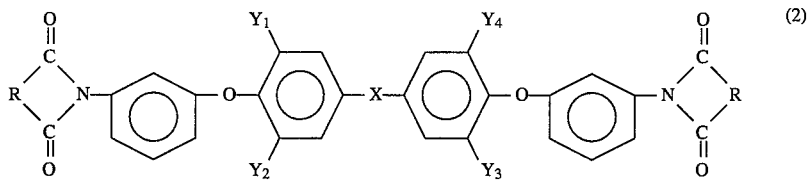

wherein X, $Y_1$–$Y_4$ and R are the same as above.

(2) A polyimide resin composition wherein the polyimide has recurring structural units represented by the formula(11):

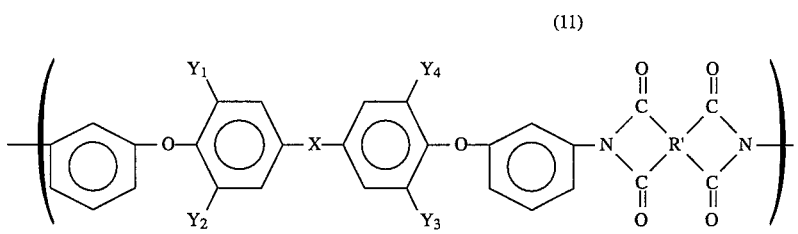

wherein X is a direct bond, a divalent hydrocarbon radical having from 1 to 10 carbon atoms, hexafluorinated isopropylidene, carbonyl, thio or sulfonyl, Y, Y, are individually hydrogen atom, lower alkyl radical, lower alkoxy radical, chlorine or bromine atom, and R' is a tetravalent radical having 2 or more carbon atoms and selected from the group consisting of an aliphatic radical, alicyclic radical, monoaromatic radical, condensed polyaromatic radical and noncondensed aromatic radical connected to each other with a direct bond or a bridge member; and the aromatic bisimide compound is represented by the above formula(10) and/or the formula(2).

(3) A polyimide resin composition wherein the polyimide has recurring structural units of the formula(9):

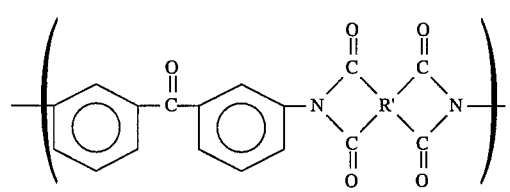

wherein R' is the same as above, and the aromatic bisimide compound is represented by the formula(3):

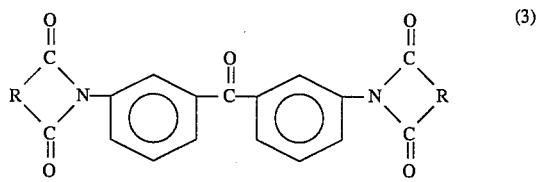

wherein R is the same as above.

(4) A polyimide resin composition wherein the polyimide has recurring structural units of the formula(11):

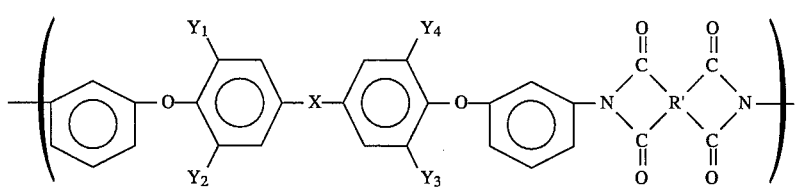

wherein X, $Y_1$–$Y_4$, and R' are the same as above, and the aromatic bisimide compound is represented by the formula(7):

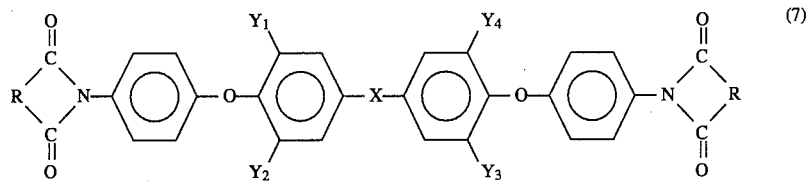

wherein X, $Y_1$–$Y_4$, and R are the same as above, the formula(12):

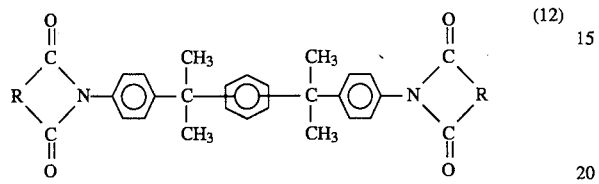

wherein R is a divalent radical selected from the group consisting of a monoaromatic radical, condensed polyaromatic radical, and noncondensed aromatic radical connected to each other with a direct bond or a bridge member, and two isopropylidene radicals are located each at para- or meta- position on a benzene ring, the formula(4):

carbonyl or sulfonyl, and R is a divalent radical having 2 or more carbon atoms and selected from the group consisting of an aliphatic radical, alicyclic radical, monoaromatic radical, condensed polyaromatic radical and noncondensed aromatic radical connected to each other with a direct bond or a bridge member, the formula(15):

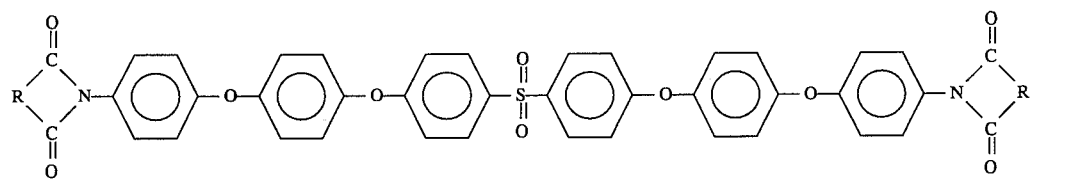

wherein R is the same as above, the formula(13):

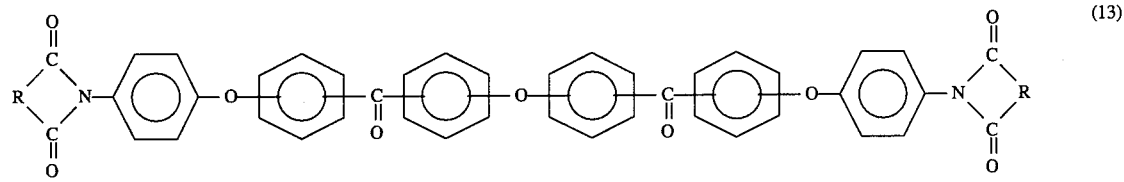

wherein R is a divalent radical selected from the group consisting of a monoaromatic radical, condensed polyaromatic radical and noncondensed aromatic radical connected to each other with a direct bond or a bridge member, and the two carbonyl radicals are located on meta- or para-position to the central ether bond, and other two ether bonds on the outside are located on meta- or para-position to said carbonyl radicals, respectively, the formula(14):

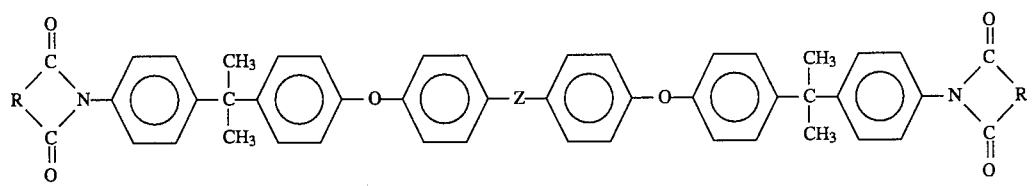

wherein Z is a radical selected from the group consisting of

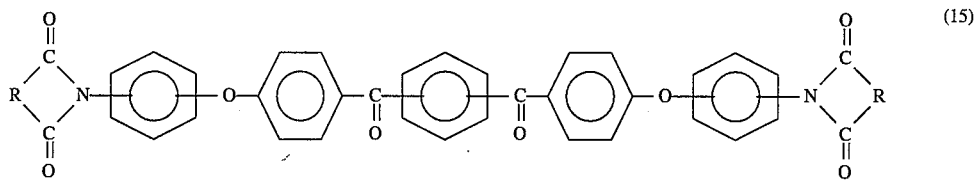

wherein R is a divalent radical selected from the group consisting of a monoaromatic radical, condensed polyaromatic radical and noncondensed aromatic radical connected to each other with a direct bond or a bridge member; the two carbonyl radicals are located other at meta or para-position on the central benzene ring; when the two carbonyl radicals are located on para-position on the central benzene ring, both terminal nitrogen atoms are located at para- or meta-position to the ether linkages, respectively; and when the two carbonyl radicals are located on meta-position on the central benzene ring, both terminal nitrogen atoms are located on para- or meta-position to the ether linkages, respectively, or the formula(16):

atoms and selected from the group consisting of an aliphatic radical, alicyclic radical, monoaromatic radical, condensed polyaromatic radical and noncondensed aromatic radical connected to each other with a direct bond or a bridge member; and the aromatic bisimide compound is represented by the above formula(10), (2), (7), (12), (4), (13), (14), (15) or (16).

A further aspect of the invention is ① a carbon fiber reinforced polyimide resin composition comprising a carbon fiber coated on the surface with an aromatic bisimide compound, preferably a bisimide compound represented by the above formula(2):

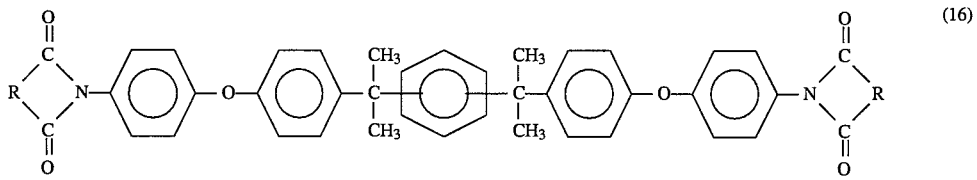

wherein R is a divalent radical selected from the group consisting of a monoaromatic radical, condensed polyaromatic radical and noncondensed aromatic radical connected to each other with a direct bond or bridge member, and the two isopropylidene radicals are located on para- or meta-position on the central benzene ring.

(5) A polyimide resin composition wherein the polyimide has recurring structural units represented by the formula(17):

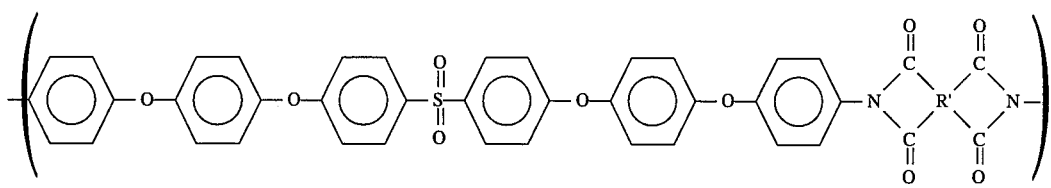

wherein R' is a tetravalent radical having 2 or more carbon

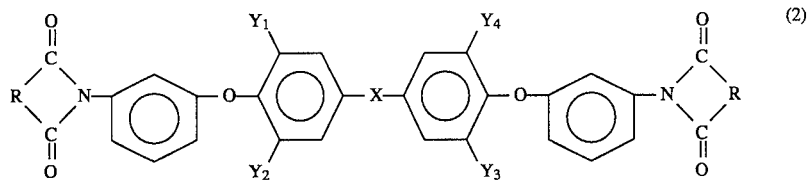

wherein X, $Y_1$–$Y_4$ and R are the same as above, and polyimide, particularly the polyimide having recurring structural units represented by the above formula(11):

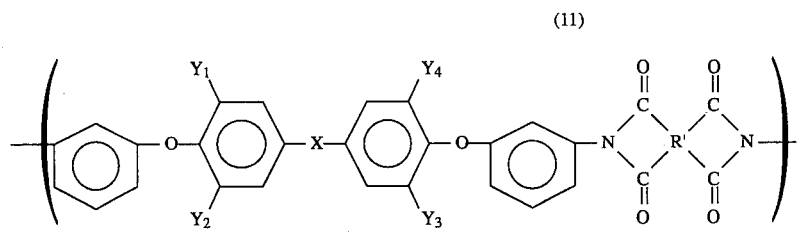

wherein X, $Y_1$–$H_4$, and R' are the same as above, or the polyimide having recurring structural units represented by the formula(9):

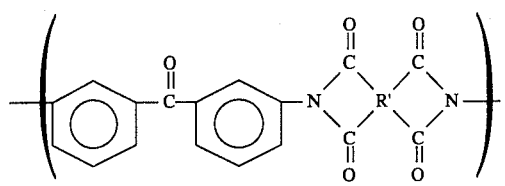

wherein R' is the same as above; or ② a carbon fiber reinforced resin composition comprising a carbon fiber coated on the surface with an aromatic bisimide compound represented by the formula(10):

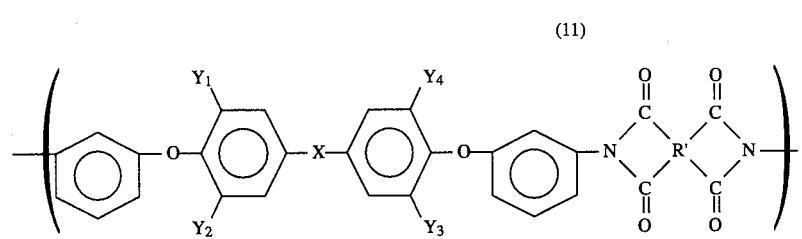

wherein B and R are the same as above, and the polyimide having recurring structural units represented by the formula(11):

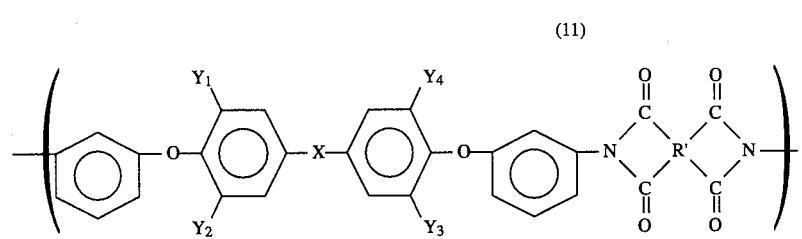

wherein X, $Y_1$–$Y_4$ and R' are the same as above.

The bisimide of the invention can simultaneously provide good heat resistance and processability for polyimide and is useful for heat resistant coatings, heat resistant adhesives, sizing agents of glass fiber and carbon fiber, and plasticizers of heat resistant resin.

Addition of the bisimide compound to polyimide resin can greatly reduce melt-viscosity of the resin and improve processability. Particularly, the polyimide resin composition comprising the bisimide compound of the invention has remarkably improved processability.

The polyimide resin composition comprising the carbon fiber coated with the bisimide compound of the invention has excellent mechanical strength and can be widely used as a material for members of electric and electronic devices, automotive trim, space and aeronautical equipment and general instruments in industry. Therefore, the invention is very valuable in industry.

DESCRIPTION OF THE PREFERRED EMBODIMENTS

Figure 1:
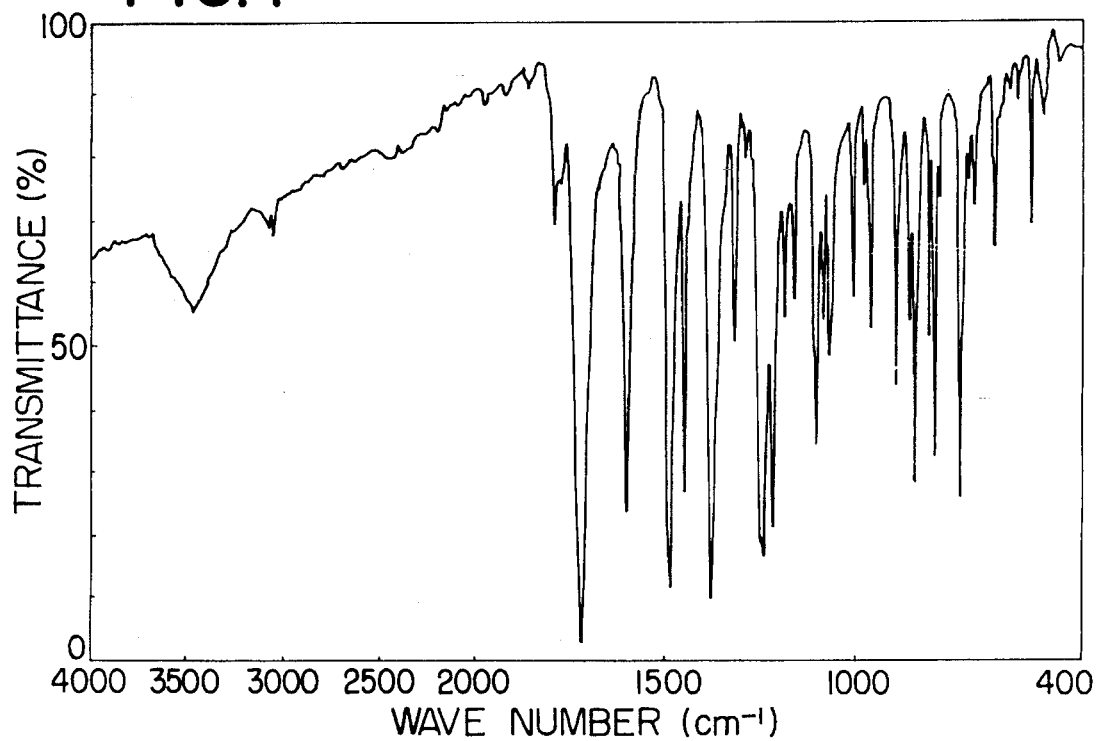
FIG. 1 is an IR absorption spectrum atlas of bisimide obtained in Example.

The bisimide compound of the invention is represented by the above formula(1) and practical compounds are respectively represented by the formulas(2), (3), (4), (5), (6) and (7).

The bisimide compound can be prepared by reacting a diamine compound represented by the formula(1-a):

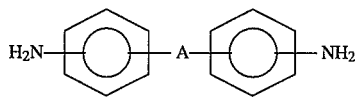

wherein A is a divalent radical selected from the group consisting of radicals having the formulas:

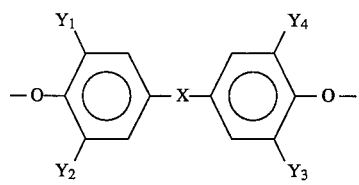

wherein X is a direct bond, a divalent hydrocarbon radical having from 1 to 10 carbon atoms, hexafluorinated isopropylidene, carbonyl, thio or sulfonyl, and $Y_1$–$Y_4$ are individually hydrogen atom, lower alkyl radical, lower alkoxy radical, chlorine or bromine atom,

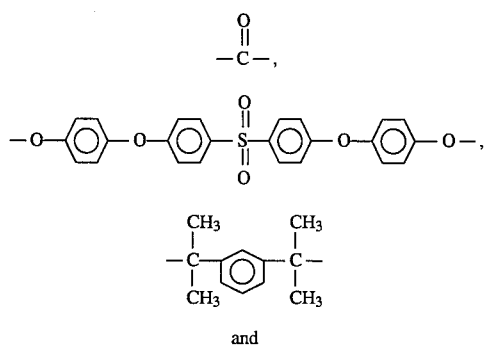

with a dicarboxylic acid anhydride represented by the formula(18):

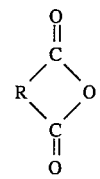

wherein R is a divalent radical selected from the group consisting of a monoaromatic radical, condensed polyaromatic radical and noncondensed aromatic radical connected to each other with a direct bond or a bridge member.

The diamine compounds used for preparing the bisimide compound of the invention are represented by the formula(2-a):

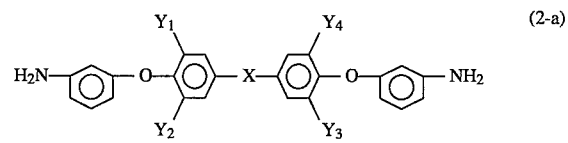

wherein X and $Y_1$–$Y_4$ are the same as in the formula(2).

Exemplary diamine compounds which are represented by the formula(2-a) include:

bis[4-(3-aminophenoxy)phenyl]methane, 1,1-bis[4-{3-aminophenoxy)phenyl]ethane, 2,2-bis[4-(3-aminophenoxy)phenyl]propane, 2-[4-(3-aminophenoxy)phenyl]-2-[4-(3-aminophenoxy)-3-methylphenyl]propane, 2,2-bis[4-(3-aminophenoxy)-3-methylphenyl]propane, 2-[4-(3-aminophenoxy)phenyl]-2-[4-(3-aminophenoxy)-3,5-dimethylphenyl] propane, 2,2-bis[4-(3-aminophenoxy)-3,5-dimethylphenyl]propane, 2,2-bis[4-(3-aminophenoxy)phenyl]butane, 2,2-bis[4-(3-aminophenoxy)phenyl]-1,1,1,3,3,3-hexafluoropropane, 4,4'-bis(3-aminophenoxy)biphenyl, 4,4'-bis(3-aminophenoxy)-3-methylbiphenyl, 4,4'-bis(3-aminophenoxy)-3,3'-dimethylbiphenyl, 4,4'-bis(3-aminophenoxy)-3,5-dimethylbiphenyl, 4,4'-bis(3-aminophenoxy)-3,3',5,5'-tetramethylbiphenyl, 4,4'-bis(3-aminophenoxy)-3,3'-dichlorobiphenyl, 4,4'-bis(3-aminophenoxy)-3,5-dichlorobiphenyl, 4,4'-bis(3-aminophenoxy)-3,3',5,5'-tetrachlorobiphenyl, 4,4'-bis(3-aminophenoxy)-3,3'-dibromobiphenyl, 4,4'-bis(3-aminophenoxy)-3,5-dibromobiphenyl, 4,4'-bis(3-aminophenoxy)-3,3',5,5'-tetrabromobiphenyl, bis[4-(3-aminophenoxy)phenyl]ketone, bis[4-(3-aminophenoxy)phenyl]sulfide, bis[4-(3-aminophenoxy)-3-methoxyphenyl]sulfide, [4-(3-aminophenoxy)phenyl][4-(3-aminophenoxy)-3,5-dimethoxyphenyl]sulfide, bis[4-(3-aminophenoxy)-3,5-dimethoxyphenyl]sulfide, and bis[4-(3-aminophenoxy)phenyl]sulfone.

Other diamine compounds which can be used are 3,3'-diaminobenzophenone of the formula(3-a):

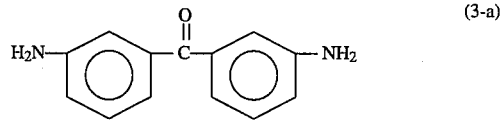

bis[4-{4-(4-aminophenoxy)phenyl}phenyl]sulfone of the formula(4-a):

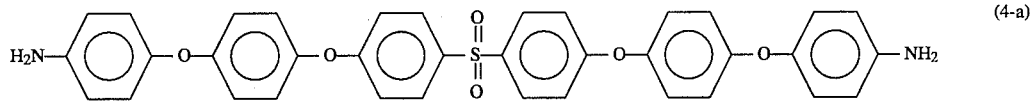 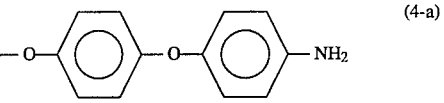

1,3-bis(4-amino-α,α-dimethylbenzyl)benzene of the formula(5-a):

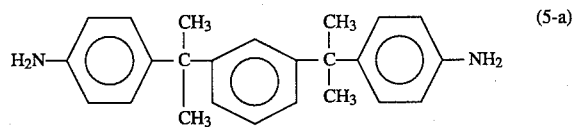

and bis[3-{4-(4-aminophenoxy)benzoyl}phenyl]ether of the formula(6-a):

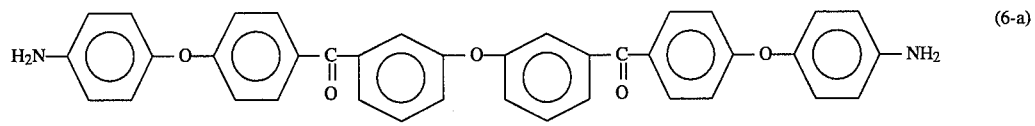

Further diamine compounds which can be used for preparing the bisimide compound are represented by the formula(7-a):

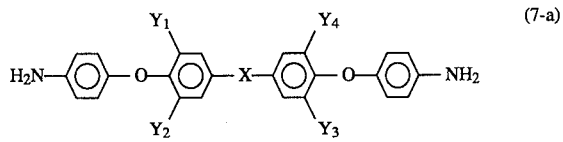

wherein X and $Y_1$–$Y_4$ are the same as in the formula(7).

Exemplary diamine compounds which are represented by the formula(7-a) include:

1,1-bis[4-(4-aminophenoxy)phenyl]methane, 1,1-bis[4-(4-aminophenoxy)phenyl]ethane, 2,2-bis[4-(4-aminophenoxy)phenyl]propane, 2-[4-(4-aminophenoxy)phenyl]-2-[4-(4-aminophenoxy)-3-methylphenyl] propane, 2,2-bis[4-(4-aminophenoxy)-3-methylphenyl]propane, 2-[4-(4-aminophenoxy)phenyl]-2-[4-(4-aminophenoxy)-3,5-dimethylphenyl] propane, 2,2-bis[4-(4-aminophenoxy)-3,5-dimethylphenyl]propane, 2,2-bis[4-(4-aminophenoxy)phenyl]butane, 2,2-bis[4-(4-aminophenoxy)phenyl]-1,1,1,3,3,3-hexafluoropropane, 4,4'-bis(4-aminophenoxy)biphenyl, 4,4'-bis(4-aminophenoxy)-3-methylbiphenyl, 4,4'-bis(4-aminophenoxy)-3,3'-dimethylbiphenyl, 4,4'-bis(4-amnophenoxy)-3,5-dimethylbiphenyl, 4,4'-bis(4-aminophenoxy)-3,3',5,5'-tetramethylbiphenyl, 4,4'-bis(4-aminophenoxy)-3,3'-dichlorobiphenyl, 4,4'-bis(4-amnophenoxy)-3,5-dichlorobiphenyl, 4,4'-bis(4-aminophenoxy)-3,3',5,5'-tetrachlorobiphenyl, 4,4'-bis(4-amnophenoxy)-3,3'-dibromobiphenyl, 4,4'-bis(4-aminophenoxy)-3,5-dibromobiphenyl, 4,4'-bis(4-aminophenoxy)-3,3',5,5'-tetrabromobiphenyl, bis[4-(4-aminophenoxy)phenyl]ketone, bis[4-(4-aminophenoxy)phenyl]sulfide, bis[4-(4-aminophenoxy)-3-methoxyphenyl]sulfide, 4-(4-aminophenoxy)phenyl][4-(4-aminophenoxy)-3,5-dimethoxyphenyl] sulfide, bis[4-(4-aminophenoxy)-3,5-dimethoxyphenyl]sulfide, and bis[4-(4aminophenoxy)phenyl]sulfone.

The diamine compounds enumerated above can be used singly or as a mixture.

The aromatic dicarboxylic acid anhydrides used for the preparation of bisimide compounds of the invention are represented by the formula(18) and include, for example, phthalic anhydride, 3-methylphthalic anhydride, 4-methylphthalic anhydride, 2,3-benzophenonedicarboxylic anhydride, 3,4-benzophenonedicarboxylic anhydride, 2,3-dicarboxyphenyl phenyl ether anhydride, 3,4-dicarboxyphenyl phenyl ether anhydride, 2,3-biphenyldicarboxylic anhydride, 3,4-biphenyldicarboxylic anhydride, 2,3-dicarboxyphenyl phenyl sulfone anhydride, 3,4-dicarboxyphenyl phenyl sulfone anhydride, 2,3-dicarboxyphenyl phenyl sulfide anhydride, 3,4-dicarboxyphenyl phenyl sulfide anhydride, 1,2-naphthalenedicarboxylic anhydride, 2,3-naphthalenedicarboxylic anhydride, 1,8-naphthalenedicarboxylic anhydride, 1,2-anthracenedicarboxylic anhydride, 2,3-anthracenedicarboxylic anhydride, and 1,9-anthracenedicarboxylic anhydride.

These anhydrides are used singly or as a mixture.

No particular restriction is imposed upon the reaction of te diamine with the dicarboxylic acid anhydride. The reaction is preferably carried out in organic solvents in particular.

Exemplary solvents used for the reaction include

N,N-dimethylformamide, N,N-dimethylacetamide, N,N-diethylacetamide, N,N-dimethylmethoxyacetamide, N-methyl-2-pyrrolidone, 1,3-dimethyl-2-imidazolidinone, N-methylcaprolactam, 1,2-dimethoxyethane, bis(2-methoxyethyl) ether, 1,2-bis(2-methoxyethoxy)ethane, bis[2-(2-methoxyethoxy)ethyl]ether, tetrahydrofuran, 1,3-dioxane, 1,4-dioxane, pyridine, picoline, dimethyl sulfoxide, dimethyl sulfone, tetramethylurea, hexamethylphosphoramide, phenol, m-cresol, p-cresol, p-chlorophenol and anisole.

These organic solvents can be used singly or as a mixture.

Reaction temperature is usually 200° C. or less, preferably 50° C. or less. No particular limitation is placed on the reaction pressure. The reaction can be satisfactorily carried out under atmospheric pressure. The reaction time varies depending upon the kind of solvents and reaction temperature. The reaction is usually carried out for sufficient time to complete formation of bisamic acid which is the precursor of the bisimide compound of the invention. The reaction time of from 10 minutes to 24 hours is usually sufficient for the reaction.

The reaction can provide bisamic acids which correspond to the desired bisimide compounds of the invention, that is, the bisamic acid having the formula(2-b):

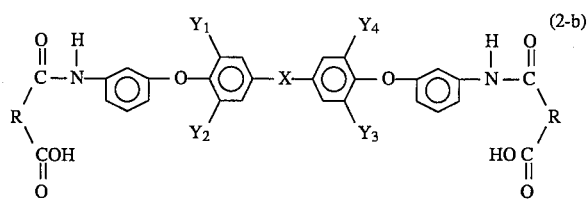

(2-b)

and corresponding to the bisimide compound of the formula(2), the bisamic acid having the formula(3-b):

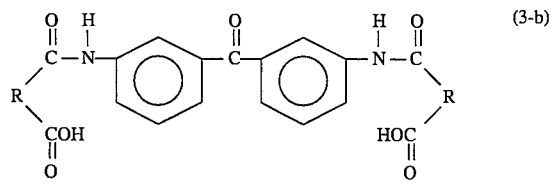

(3-b)

and corresponding to the bisimide compound of the formula(3), the bisamic acid having the formula(4-b);

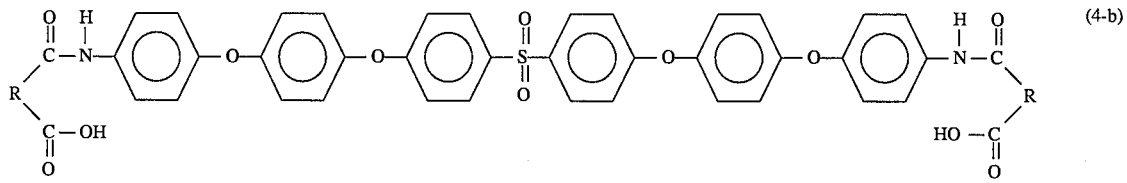

(4-b)

and corresponding to the bisimide compound of the formula(4), the bisamic acid having the formula(5-b):

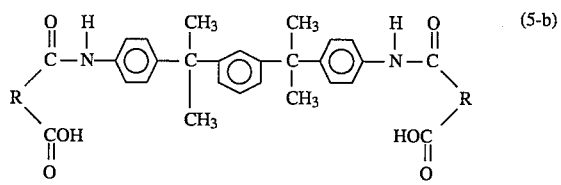

(5-b)

and corresponding to the bisimide compound of the formula(5), the bisamic acid having the formula(6-b):

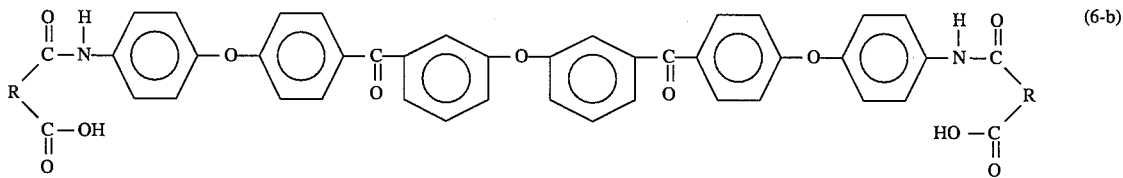

(6-b)

and corresponding to the bisimide compound of the formula(6), and the bisamic acid having the formula(7-b):

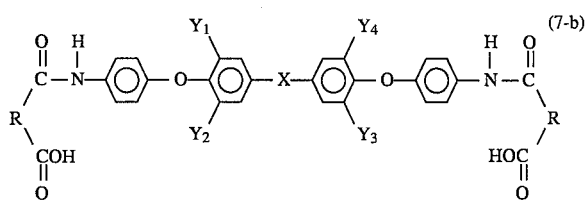

(7-b)

and corresponding to the bisimide compound of the formula(7).

The bisamic acids thus obtained are heat-imidized at temperature of 80° to 400° C. or by chemically imidized with an imidizing agent such as acetic anhydride to give bisimide compounds having the formulas(1) to (7).

Alternatively, the above diamine compound and the above dicarboxylic acid anhydride are suspended or dissolved in an organic solvent, and formation and dehydrating imidization of the resulting bisamic acid can be simultaneously carried out by heating from 50° to 400° C. to give corresponding bisimide compounds.

The bisimide compounds having the formulas(2) and (7) which are prepared from the diemine compounds having the formulas (2-a) and (7-a) have a melting point of 290° C. or less. The bisimide compounds having the formula(3) which are prepared from the diemine compounds having the formula(3-a) have a melting point of 260° C. or less. Thus the bisimide compounds obtained in the invention have lower melting points, can be melt-processed with ease and have excellent processability as compared with high molecular weight polyimide. The bisimide compounds also have solubility of 5% by weight or more in halogenated hydrocarbon solvents such as dichloromethane, chloroform and carbon tetrachloride, and can be used in the form of solutions in these solvents.

The polyimide resin composition of the invention is a novel polyimide resin composition comprising the aromatic bisimide compound and the polyimide as requisite components. The polyimide resin composition prepared by using the novel bisimide compound having the formula(1) of the invention is preferred in particular.

No particular restriction is imposed upon the polyimide used in the polyimide resin composition of the invention. Various kinds of polyimide can be used and particularly preferred polyimide has recurring structural units represented by the formula(8):

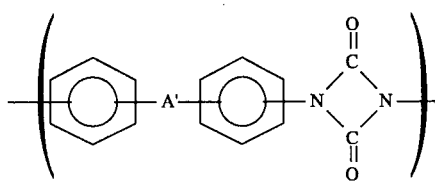  (8)

wherein A' and R' are the same as above. Useful kinds of polyimide include, for example, the polyimide having recurring structural units of the formula(9):

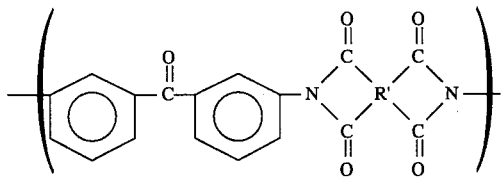  (9)

wherein R' is the same as above, the polyimide having recurring structural units of the formula(11):

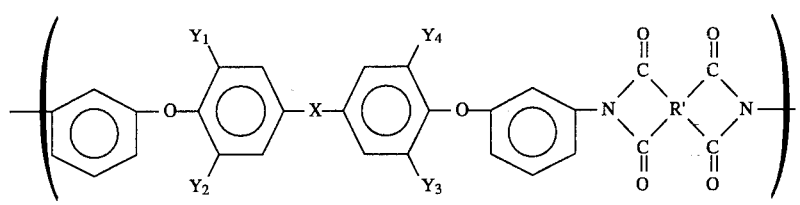  (11)

wherein X, $Y_1$–$Y_4$ and R' are the same as above, and the polyimide having recurring structural units of the formula(17):

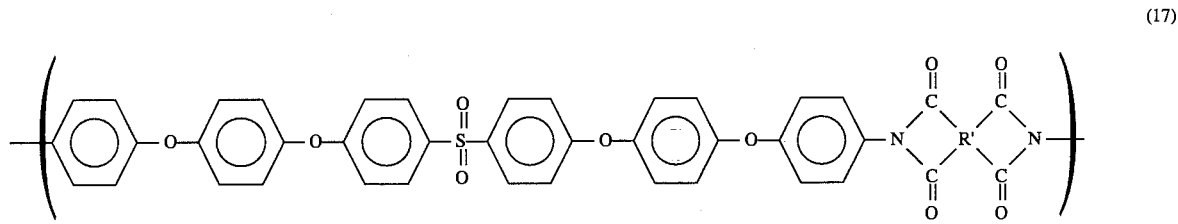  (17)

wherein R' is the same as above.

Consequently, representative embodiments of combination composed of the polyimide resin component and the bisimide compound component include:

(1) the combination of the polyimide having recurring structural units of the formula(9):

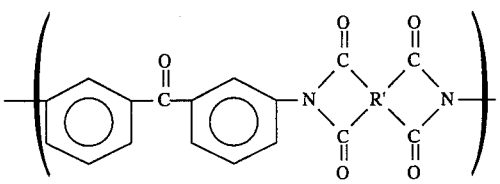  (9)

wherein R' is the same as above, with the bisimide compound having the formula(10):

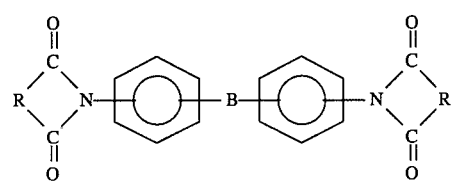  (10)

wherein B and R are the same as above, and/or the formula(2):

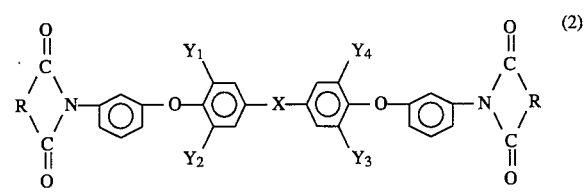  (2)

wherein X, $Y_1$–$Y_4$ and R are the same as above, (2) the combination of the polyimide having recurring structural units of the formula(11):

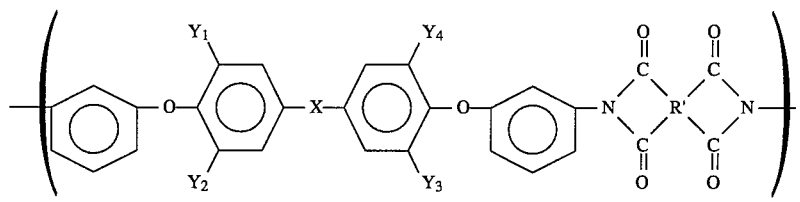

wherein X, $Y_1$–$Y_4$ and R' are the same as above, with the bisimide compound having the formula(10):

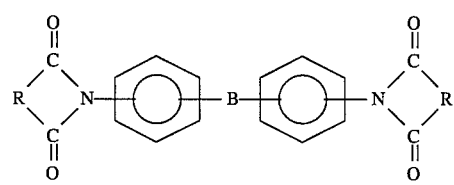

wherein B and R are the same as above, and/or the formula(2):

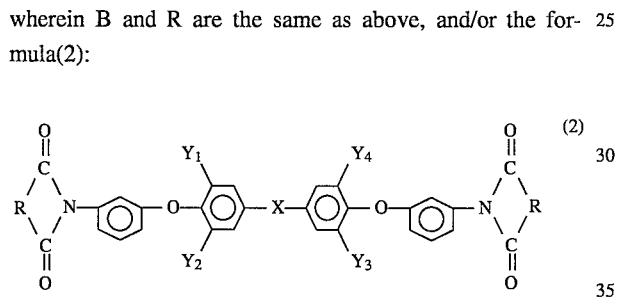

wherein X, $Y_1$–$Y_4$, and R are the same as above, (3) the combination of the polyimide having recurring structural units of the formula(9):

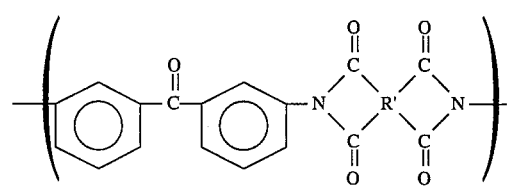

wherein R' is the same as above, with the bisimide compound having the formula(3):

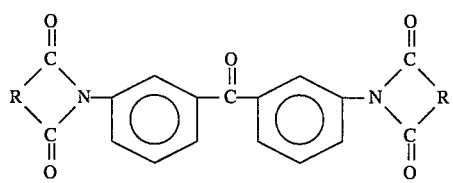

wherein R is the same as above, (4)–(17) the combination of the polyimide having recurring structural units of the formula(11) or (17):

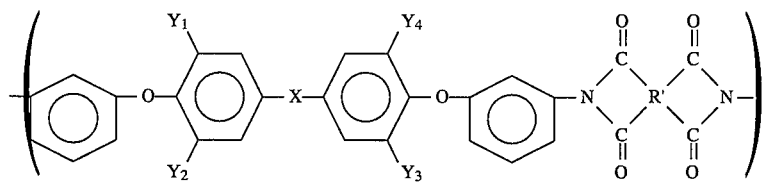

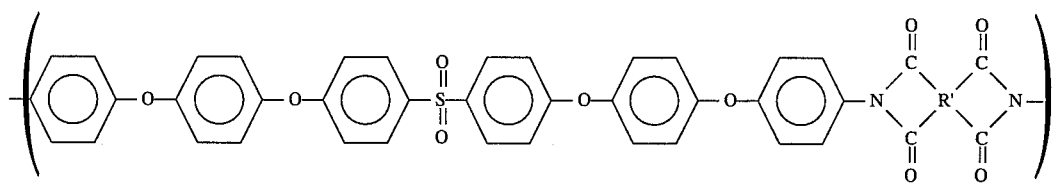

wherein R' and $Y_1$–$Y_4$, are the same as above, with the bisimide compound having the formula(7):

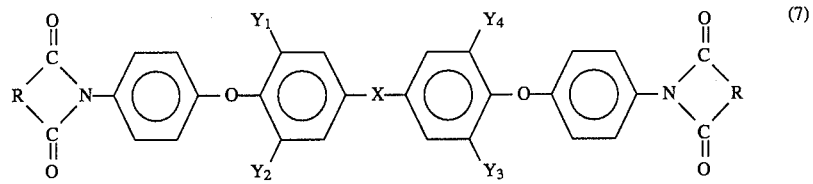
wherein R and $Y_1$-$Y_4$ are the same as above, the formula(12):
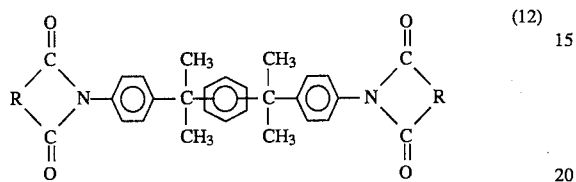
wherein R is the same as above, the formula(4):
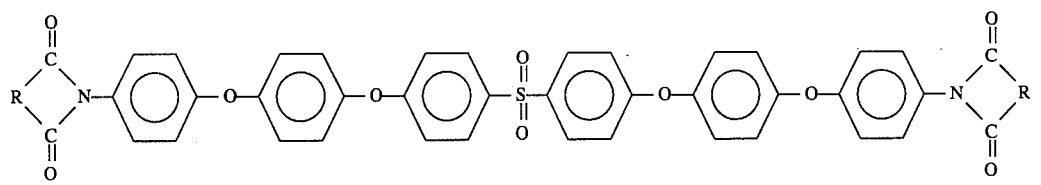
wherein R is the same as above, the formula(13):
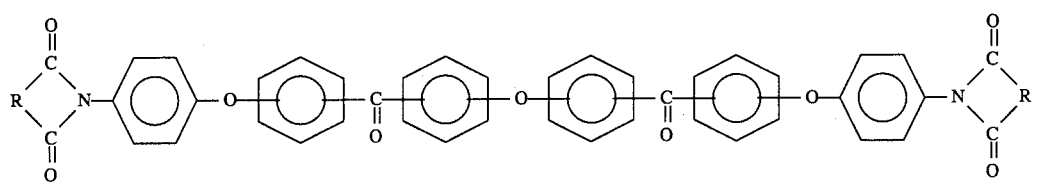
wherein R is the same as above, the formula(14):
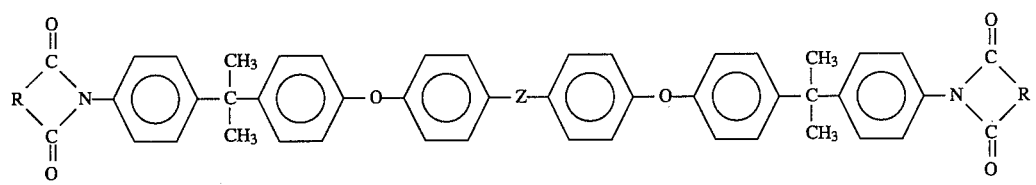
wherein R and Z are the same as above, the formula(15):
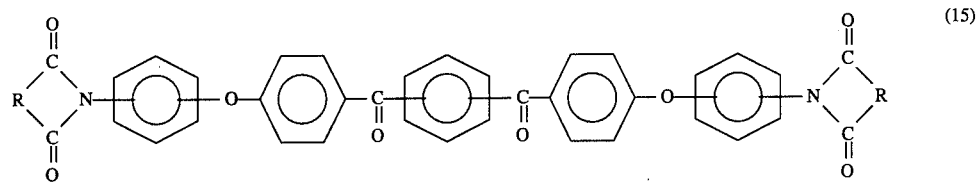
wherein R is the same as above, or the formula(16):

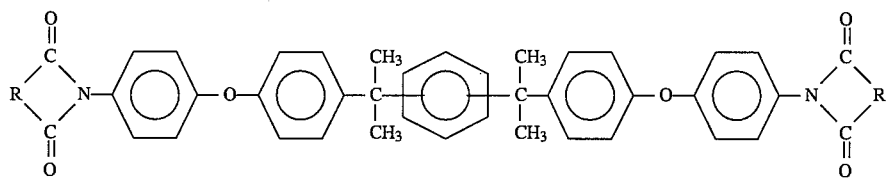

wherein R is the same as above.

The polyimide used in the composition of the invention can be prepared by reacting a diamine compound with a tetracarboxylic acid dianhydride of the formula(19):

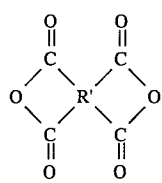

wherein R' is a tetravalent radical having 2 or more carbon atoms and selected from the group consisting of an aliphatic radical, alicyclic radical, monoaromatic radical, condensed polyaromatic radical and noncondensed aromatic radical connected to each other with a direct bond or a bridge member, and successively by carrying out dehydrating cyclization of the resultant polyamic acid.

The polyimide can be practically prepared with ease by the processes disclosed in Japanese Laid-Open Patent Hei 2-022422, 2 -133427 and 2-229124.

Various diamine compounds can be used as raw materials for providing the desired polyimide. For example, the following diamine compounds can be used.

In order to obtain polyimide having recurring structural units of the above formula(9), 3,3-diaminobenzophenone is used.

Exemplary diamines which can provide the polyimide having recurring structural units of the above formula(11) include bis[4-(3-aminophenoxy)phenyl]methane, 1,1-bis[4-(3-aminophenoxy)phenyl]ethane, 2,2-bis[4-(3-aminophenoxy)phenyl]propane, 2-[4-(3-aminophenoxy)phenyl]-2-[4-(3-aminophenoxy)-3-methylphenyl]propane, 2,2-bis[4-(3-aminophenoxy)-3,5-dimethylbenzoyl]propane, 2,2-bis[4-(3-aminophenoxy)-3-methylphenyl]propane, 2-[4-(3-aminophenoxy)phenyl]-2-[4-(3-aminophenoxy)-3,5-dimethylphenyl]propane, 2,2-bis[4-(3-aminophenoxy)phenyl]butane, 2,2-bis[4-(3-aminophenoxy)phenyl]-1,1,1,3,3,3-hexafluoropropane, 4,4'-bis(3-aminophenoxy)biphenyl, 4,4'-bis(3-aminophenoxy)-3-methylbiphenyl, 4,4'-bis(3-aminophenoxy)-3,3'-dimethylbiphenyl, 4,4'-bis(3-aminophenoxy)-3,5'-dimethylbiphenyl 4,4'-bis(3-aminophenoxy)-3,3',5,5'-tetramethylbiphenyl, 4,4'-bis(3-aminophenoxy)-3,3'-dichlorobiphenyl, 4,4'-bis(3-aminophenoxy)-3,5'-dichlorobiphenyl, 4,4'-bis(3-aminophenoxy)-3,3',5,5'-tetrachlorobiphenyl, 4,4'-bis(3-aminophenoxy)-3,3'-dibromobiphenyl, 4,4'-bis(3-aminophenoxy)-3,5'-dibromobiphenyl, 4,4'-bis(3-aminophenoxy)-3,3',5,5'-tetrabromobiphenyl, bis[4-(3-aminophenoxy)phenyl]ketone, bis[4-(3-aminophenoxy)phenyl]sulfide, bis[4-(3-aminophenoxy)-3-methoxyphenyl]sulfide, [4-(3-aminophenoxy)phenyl][4-(3-aminophenoxy)-3,5-dimethoxyphenyl]sulfide, bis[4-(3-aminophenoxy)-3,5-dimethoxyphenyl]sulfide, and bis[4-(3-aminophenoxy)phenyl]sulfone.

These diamine compounds can be used singly or as a mixture.

In order to obtain the polyimide of the above formula(17), bis[4-{4-(4-aminophenoxy)phenoxy}phenyl]sulfone is used.

Tetracarboxylic acid dianhydrides used in the invention and represented by the formula(19) include, for example, ethylenetetracarboxylic dianhydride, butanetetracarboxylic dianhydride, cyclopentanetetracarboxylic dianhydride, pyromellitic dianhydride, 1,1-bis(2,3-dicarboxyphenyl)ethane dianhydride, bis(2,3-dicarboxyphenyl)methane dianhydride, bis(3,4-dicarboxyphenyl)methane dianhydride, 2,2-bis(3,4-dicarboxyphenyl)propane dianhydride, 2,2-bis(2,3-dicarboxyphenyl)propane dianhydride, 2,2-bis(3,4-dicarboxyphenyl)-1,1,1,3,3,3-hexafluoropropane dianhydride, 2,2-bis(2,3-dicarboxyphenyl)-1,1,1,3,3,3-hexafluoropropane dianhydride, 3,3',4,4'-benzophenonetetracarboxylic dianhydride, 2,2',3,3'-benzophenonetetracarboxylic dianhydride, 3,3',4,4'-biphenyltetracarboxylic dianhydride, 2,2',3,3'-biphenyltetracarboxylic dianhydride, bis(3,4-dicarboxyphenyl)ether dianhydride, bis(2,3-dicarboxyphenyl)ether dianhydride, bis(3,4-dicarboxyphenyl)sulfone dianhydride, 4,4'-(p-phenylenedioxy)diphthalic dianhydride, 4,4'-(m-phenylenedioxy)diphthalic dianhydride, 2,3,6,7-naphthalenetetracarboxylic dianhydride, 1,4,5,8-naphthalenetetracarboxylic dianhydride, 1,2,5,6-naphthalenetetracarboxylic dianhydride, 1,2,3,4-benzenetetracarboxylic dianhydride, 3,4,9,10-perylenetetracarboxylic dianhydride, 2,3,6,7-anthracenetetracarboxylic dianhydride, and 1,2,7,8-phenanthrenetetracarboxylic dianhydride.

These tetracarboxylic acid dianhydrides can be used singly or as a mixture.

In the preparation of the polyimide resin, a part of the above diamine can be replaced with other aromatic diamines in the range giving no adverse effect on the good properties of the polyimide of the invention, for example, in the range of usually 50% by weight or less, preferably 30% by weight or less for the amount of the above diamine.

In preparing the polyimide resin, it is preferred in view of improving heat stability to carry out the reaction in the presence of dicarboxylic acid anhydride or monoamine.

Exemplary aromatic diamines which can replace the above diamines include m-phenylenediamine, o-phenylenediamine, p-phenylenediamine, m-aminobenzylamine, p-aminobenzylamine, bis(3-aminophenyl)ether, (3-aminophenyl)(4-aminophenyl)ether, bis(4-aminophenyl)ether, bis(3-aminophenyl)sulfide, (3-aminophenyl)(4-aminophenyl)sulfide, bis(4-aminophenyl)sulfide, bis(3-aminophenyl)sulfoxide, (3-aminophenyl)(4-aminophenyl)sulfoxide, bis(4-aminophenyl)sulfoxide, bis(3-aminophenyl)sulfone, (3-aminophenyl)(4-aminophenyl)sulfone, bis(4-aminophenyl)sulfone, 3,4'-diaminobenzophenone, 4,4'-diaminobenzophenone, bis[4-(4-aminophenoxy)phenyl]methane, 1,1-bis[4-(4-aminophenoxy)phenyl]ethane, 1,2-bis[4-(4-aminophenoxy)phenyl]ethane, 2,2-bis[4-(4-aminophenoxy)phenyl]propane, 2,2-bis[4-(4-aminophenoxy)phenyl]butane, 2,2-bis[4-(4-aminophenoxy)phenyl]-1,1,1,3,3,3-hexafluoropropane, 1,3-bis(3-aminophenoxy)benzene, 1,3-bis(4-aminophenoxy)benzene, 1,4-bis(3-aminophenoxy)benzene, 1,4-bis(4-aminophenoxy)benzene, 4,4'-bis(4-aminophenoxy)biphenyl, bis[4-(4-aminophenoxy)phenyl]ketone, bis[4-(4-aminophenoxy)phenyl]sulfide, bis[4-(4-aminophenoxy)phenyl]sulfoxide, bis[4-(4-aminophenoxy)phenyl]sulfone, bis[4-(3-aminophenoxy)phenyl]ether, bis[4-(4-aminophenoxy)phenyl]ether, 1,4-bis[4-(3-aminophenoxy)benzoyl]benzene, 1,3-bis[4-(3-aminophenoxy)benzoyl]benzene, bis[4-(3-aminophenoxy)phenyl]methane, 1,1-bis[4-(3-aminophenoxy)phenyl]ethane, 2,2-bis[4-(3-aminophenoxy)phenyl]propane, 2-[4-(3-aminophenoxy)phenyl]-2-[4-(3-aminophenoxy)-3-methylphenyl]propane, 2,2-bis[4-(3-aminophenoxy)-3-methylphenyl]propane, 2-[4-(3-aminophenoxy)phenyl]-2-[4-(3-aminophenoxy)-3,5-dimethylphenyl]propane, 2,2-bis[4-(3-aminophenoxy)-3,5-dimethylphenyl]propane, 2,2-bis[4-(3-aminophenoxy)phenyl]butane, 2,2-bis[4-(3-aminophenoxy)phenyl]-1,1,1,3,3,3-hexafluoropropane, 4,4'-bis(3-aminophenoxy)biphenyl, 4,4'-bis(3-aminophenoxy)-3-methylbiphenyl, 4,4'-bis(3-aminophenoxy)-3,3'-dimethylbiphenyl, 4,4'-bis(3-aminophenoxy)-3,5'-dimethylbiphenyl, 4,4'-bis(3-aminophenoxy)-3,3,5,5'-tetramethylbiphenyl, 4,4'-bis(3-aminophenoxy)-3,3'-dichlorobiphenyl, 4,4'-bis(3-amnophenoxy)-3,5'-dichlorobiphenyl, 4,4'-bis(3-amnophenoxy)-3,3,5,5'-tetrachlorobiphenyl, 4,4'-bis(3-aminophenoxy)-3,3'-dibromobiphenyl, 4,4'-bis(3-aminophenoxy)-3,5'-dibromobiphenyl, 4,4'-bis(3-aminophenoxy)-3,3,5,5'-tetrabromobiphenyl, bis[4-(3-aminophenoxy)phenyl]ketone, bis[4-(3-aminophenoxy)phenyl]sulfide, bis[4-(3-aminophenoxy)-3-methoxyphenyl]sulfide, [4-(3-aminophenoxy)phenyl][4-(3-aminophenoxy)-3,5-dimethoxyphenyl] sulfide, bis[4-(3-aminophenoxy)-3,5-dimethoxyphenyl]sulfide, and bis[4-(3-aminophenoxy)phenyl]sulfone.

The polyimide resin powder of the above formula(9) has an inherent viscosity in the range of usually from 0.10 to 1.50 dl/g, preferably from 0.30 to 1.22 dl/g. The viscosity lower than 0.10 dl/g cannot provide the desired mechanical strengths. On the other hand, the viscosity higher than 1.50 dl/g leads to high melt viscosity and poor processability.

The polyimide resin powder of the above formula(11) has an inherent viscosity in the range of usually from 0.10 to 1.50 dl/g, preferably from 0.25 to 1.22 dl/g. The viscosity lower than 0.10 dl/g cannot provide the desired mechanical strengths. On the other hand, the viscosity higher than 1.50 dl/g leads to high melt viscosity and poor processability.

The inherent viscosity indicated herein is measured at 35° C. in a solution containing 0.5 g of the polyimide resin in 100 ml of a solvent mixture of p-chlorophenol/phenol in a ratio of 90/10 by weight.

The aromatic bisimide compounds which can be used as fluidization accelerators in the composition of the invention include the compound of the formula(1), the compounds illustrated by the lower concept, that is, the formula(2), (3), (4), (5), (6) or (7), and other various aromatic bisimide compounds.

In the aromatic bisimide compounds which are used for a component of the composition of the invention, the bisimide compound of the invention can be prepared by the above preparation process and the processes described in detail in the examples.

Other bisimide compounds used for the composition of the invention, that is, the bisimide compounds of the formulas(10), (13), (14), (15) and (17) are prepared by the following processes.

The bisimide compound represented by the formula(10) and/or the formula(2) can be prepared with ease by reacting the diamine represented by the formula(10-a):

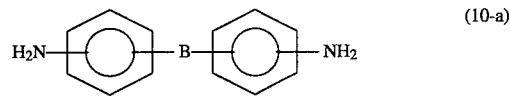

(10-a)

wherein B is the same as in the formula(10), and/or the diamine represented by the formula(2-a), with the aromatic dicarboxylic acid anhydride represented by the formula(19) and successively by carrying out dehydrating cyclization of the resultant bisamic acid.

Useful diamines represented by the formula(10-a) include, for example, 3,3'-diaminodiphenyl ether, 3,4'-diaminodiphenyl ether, 4,4'-diaminodiphenyl ether, 3,3'-diaminodiphenyl sulfide, 3,4'-diaminodiphenyl sulfide, 4,4'-diaminodiphenyl sulfide, 3,3'-diaminodiphenyl sulfone, 3,4'-diaminodiphenyl sulfone, 4,4'-diaminodiphenyl sulfone, 3,3'-diaminobenzophenone, 3,4'-diaminobenzophenone, 4,4'-diaminobenzophenone, 3,3'-diaminodiphenylmethane, 3,4'-diaminodiphenylmethane, 4,4'-diaminodiphenylmethane, 1,1-bis(3-aminophenyl)ethane, 1,1-bis(4-aminophenyl)ethane, 1,1-(3-aminophenyl)(4-aminophenyl)ethane, 2,2-bis(3-aminophenyl)propane, 2,2-bis(4-aminophenyl)propane, 2,2-(3-aminophenyl)(4-aminophenyl)propane, 2,2-bis(3-aminophenyl)-1,1,1,3,3,3-hexafluoropropane, 2,2-bis(4-aminophenyl)-1,1,1,3,3,3-hexafluoropropane and 2,2-(3-aminophenyl)(4-aminophenyl)-1,1,1,3,3,3-hexafluoropropane.

These diamines can be used singly or as a mixture.

The diamines of the formula(2-a) which can be used are compounds practically enumerated above. These diamines can be used singly or as a mixture.

The diamines of the formula(10-a) can be previously mixed with the diamines of the formula(2-a) in the preparation of the bisimide compound.

The aromatic dicarboxylic acid anhydrides which can be used are compounds represented by the formula(18) and include, for example, phthalic anhydride, 3-methylphthalic anhydride, 4-methylphthalic anhydride, 2,3-benzophenonedicarboxylic anhydride, 3,4-benzophenonedicarboxylic anhydride, 2,3-dicarboxyphenyl phenyl ether anhydride, 3,4-dicarboxyphenyl phenyl ether anhydride, 3,4-biphenyldicarboxylic anhydride, 2,3-biphenyldicarboxylic anhydride, 2,3-dicarboxyphenyl phenyl sulfone anhydride, 3,4-dicarboxyphenyl phenyl sulfone anhydride, 2,3-dicarboxyphenyl phenyl sulfide anhydride, 3,4-dicarboxyphenyl phenyl sulfide anhydride, 1,2-naphthalenedicarboxylic anhydride, 2,3-naphthalenedicarboxylic anhydride, 1,8-naphthalenedicarboxylic anhydride, 1,2-anthracenedicarboxylic anhydride, 2,3-anthracenedicarboxylic anhydride and 1,9-anthracenedicarboxylic anhydride.

These compound can be used singly or as a mixture.

The diamine compounds used for preparing the other bisimide compounds of the formula(12) are represented by the formula(12-a):

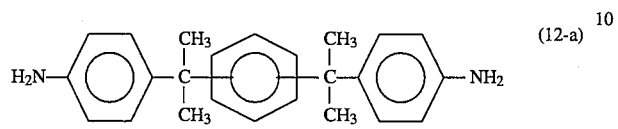

and include
bis[3-{4-(4-aminophenoxy)benzoyl}phenyl]ether, bis[4-{4-(4-aminophenoxy)benzoyl}phenyl]ether, bis[4-{3-(4-aminophenoxy benzoyl}phenyl]ether and bis[3-{3-(4-aminophenoxy)benzoyl}phenyl]ether.

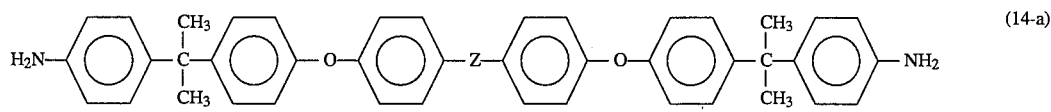

wherein Z is the same as above, and include
4,4'-bis[4-(4-amino-α,α-dimethylbenzyl)phenoxy]benzophenone and bis[4-{4-(4-amino-α,α-dimethylbenzyl)phenoxy}phenyl]sulfone.

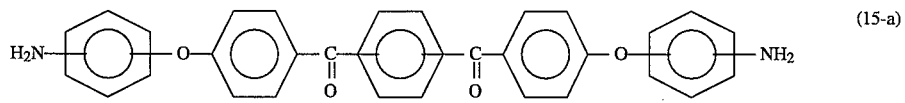

and include, for example,
1,4-bis[4-(3-aminophenoxy)benzoyl]benzene, 1,4-bis[4-(4-aminophenoxy)benzoyl]benzene, 1,3-bis[4-(3-aminophenoxy)benzoyl]benzene and 1,3-bis[3-(3-ami-

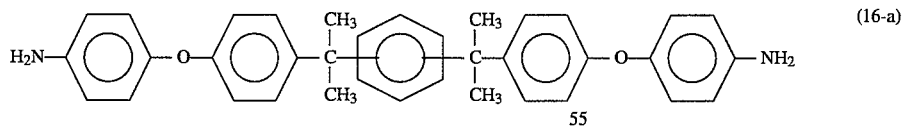

and include, for example,
1,4-bis[4-(4-aminophenoxy)-α,α-dimethylbenzyl]benzene and 1,3-bis[4-(4-aminophenoxy)-α,α-dimethylbenzyl)benzene.

The aromatic dicarboxylic acid anhydride are represented by the above formula(18) and any of the compounds practically enumerated can be used.

No particular restriction is imposed upon the method for reacting the diamine compound with the dicarboxylic acid anhydride. Known methods can be arbitrarily employed. The method for preparing the above bisimide compound of the invention can also be employed.

and include, for example, 1,3-bis(4-amino-α,α-dimethylaminobenzyl) benzene and 1,4-bis(4-amino-α,α-dimethylaminobenzyl)benzene.

Exemplary diamine compounds used for preparing the bisimide compounds of the formula(13) are represented by the formula(13-a):

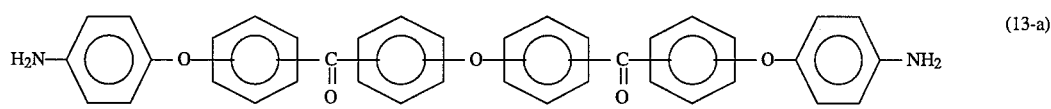

(4-aminophenoxy)benzoyl}phenyl]ether.

Representative diamine compounds used for preparing the bisimide compounds of the formula(14) are represented by the formula(14-a):

Useful diamine compounds for use in the preparation of the bisimide compounds of the formula(15) are represented by the formula(15-a):

nophenoxy)benzoyl]benzene.

The diamine compounds which can be used for the preparation of the bisimide compounds of the formula(16) are represented by the formula(16-a):

In processing the resin composition of the invention, the aromatic bisimide compound is used in the range of from 0.5 to 100 parts by weight for 100 parts by weight of the polyimide. The effect of the aromatic bisimide compound as a fluidization accelerator can be observed in a relatively small amount. Even an amount of 0.5 part by weight of the bisimide compound for 100 parts by weight of the polyimide is also effective. An amount of 1 part by weight or more is particularly effective. However, an amount of the aromatic bisimide compound exceeding 100 parts by weight tends to impair the mechanical strength of the resulting polyimide resin composition, and the range of 100 parts by weight or less is thus preferred.

Preparation of the polyimide resin composition of the invention can be carried out by usually known methods. For example, following methods are preferred.

1. Polyimide resin powder and the aromatic bisimide compound is premixed into powder with a mortar, Henschel mixer, drum blender, tumbling blender, ball mill or ribbon blender.
2. Polyimide resin powder is previously dissolved or suspended in an organic solvent, the aromatic bisimide compound is added to the resulting solution or suspension and uniformly suspended or dissolved, and thereafter the solvent is removed to obtain powder.
3. An aromatic bisimide compound and/or its aromatic bisamic acid precursor are dissolved or suspended in an organic solvent solution of polyamic acid which is the precursor of the polyimide and successively heat-treated at 100 to 400° C. or chemically imidized with a usual imidizing agent. Solvent is removed from the resulting mixture to obtain the powder.

The resin composition thus obtained in the form of powder can be used as intact for various processes such as injection molding, compression molding, transfer molding and extrusion. The powder is more preferably processed after melt-kneading.

Melt-kneading can be carried out with equipment for meltkneading common rubbers or plastics, for example, hot rolls, Banbury mixer, Brabender and extruder. Melt-kneading temperature is usually set higher than melting temperature of the blending system and lower than decomposition initiating temperature of the system. The temperature is usually from 280° to 420° C., preferably from 300° to 400° C.

Injection molding and extrusion forming which can perform uniform melt-kneading and have high productivity are suitable for processing the resin composition of the invention. However, transfer molding, compression molding, sinter molding, and other processing methods can also be applied.

Prepreg for composite materials can be prepared by melt-impregnating carbon fiber or glass fiber with the above uniformly kneaded resin composition or by impregnating various fibers with a uniform solution or dispersion of the polyimide resin and aromaticbisimide compound, and successively by removing the solvent.

Various kinds of additives can be incorporated with the resin composition of the invention.

Useful additives include, for example, solid lubricants such as molybdenum disulfide, graphite, boron nitride, lead monoxide and lead powder; reinforcements such as glass fiber, carbon fiber, aromatic polyimide, silicon carbide fiber, potassium titanate fiber and glass beads; and other common auxiliary agents such as antioxidants, heat stabilizers, ultraviolet absorbers, flame retardants, antistatic agents, lubricants and colorants. These additives can be used singly or as a mixture in an amount giving no adverse effect on the properties of the resin composition of the invention.

A further embodiment of the invention is a polyimide resin composition comprising the polyimide resin and carbon fiber coated on the surface with the aromatic bisimide compound. As result of more detailed investigation by the inventors, the invention is a polyimide resin composition comprising a carbon fiber coated as a collecting agent on the surface with a bisimide compound represented by the above formula(10):

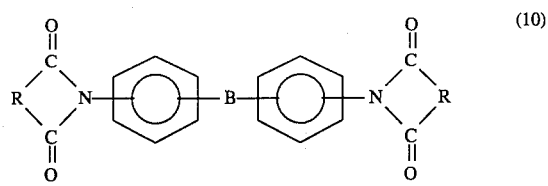

wherein B and R are the same as above, and a polyimide having recurring structural units represented by the formula(11):

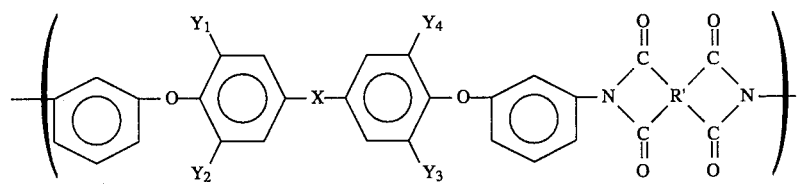

wherein X, $Y_1$–$Y_4$, and R' are the same as above; or a polyimide resin composition comprising a carbon fiber coated as a collecting agent on the surface with a bisimide compound represented by the formula(2):

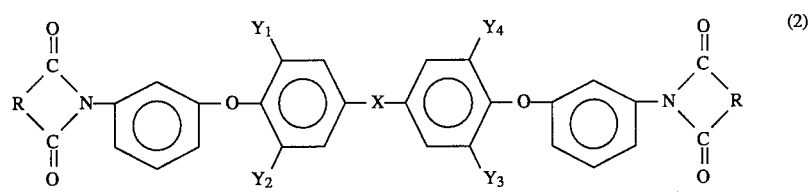

wherein X, $Y_1$–$Y_4$, and R' are the same as above, and a polyimide having recurring structural units represented by the formula(11):

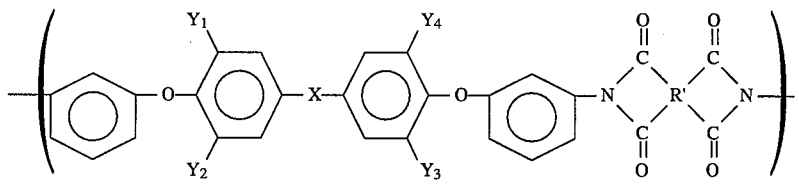

(11)

wherein X, $Y_1$–$Y_4$ and R' are the same as above, or a polyimide having recurring structural units represented by the formula(9):

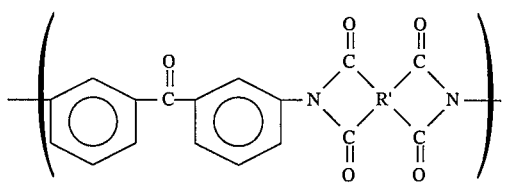

(9)

wherein R' is the same as above.

When the bisimide compound of the formula(15) is applied to the carbon fiber, the polyimide having recurring structural units of the formula(11) is preferably used in particular. When the bisimide compound of the formula(2) is applied to the carbon fiber, the polyimides having recurring structural units of the formula(11) and recurring structural units of the formula(9) are preferably used.

The polyimide used for the composition of the invention and the bisimide compound applied to the carbon fiber can be prepared by using the same or different diamine as a raw material component. That is, X and $Y_1$–$Y_4$ in the formula(11) can be the same as or different from X and $Y_1$–$Y_4$ in the formula(2).

Exemplary carbon fibers which can be coated with the bisimide compound include acrylic carbon fiber, rayon-based carbon fiber, lignin-based carbon fiber and pitch-based carbon fiber. Acrylic carbon fiber is most preferably used in the invention because of its highest fiber strength.

wherein R' is the same as above.

The bisimide compound which is applied to the carbon fiber in the invention is represented by the formula(10) or the formula(2) which is obtained by reacting the diamine with the dicarboxylic acid anhydride as described above.

The polyimide resin which can be used for the composition of the invention has recurring structural units represented by the formula(11):

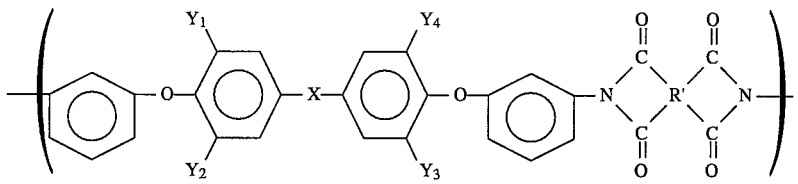

(11)

wherein X, $Y_1$–$Y_4$, and R' are the same as above, or recurring structural units represented by the formula(9):

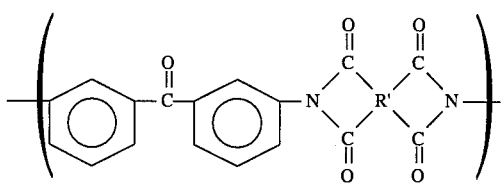

(9)

The form of carbon fiber can be any kind such as chopped strand, roving and woven fabric. The surface of carbon fiber is more preferably oxidation-treated in advance by ozone or electrolytic oxidation.

In order to apply the bisimide compound to carbon fiber, the bisimide compound is dissolved in a solvent such as dichloromethane, chloroform, 1,2-dichloroethane, 1,1,2,2-tetrachloroethane, dimethyl sulfoxide, N,N-dimethylacetamide, N-methyl-pyrrolidone, methyl ethyl ketone, 1,1,2-trichloroethane, m-cresol, p-cresol, o-cresol, p-chlorophenol, o-chlorophenol, m-chlorophenol and phenol.

Carbon fiber is immersed in the resulting bisimide solution and successively dried by removing the solvent to obtain the bisimide coated carbon fiber.

The bisimide compound of the formula(2) which can be used in the invention has a melting point of 290° C. or less and the bisimide compound of the formula(15) has a melting point of 350° C. or less. Both bisimide compounds can be melt processed and thus the bisimide coated carbon fiber can also be prepared by a melt-immersion method.

The coating amount of the bisimide compound on the carbon fiber is preferably in the range of from 0.1 to 10 parts by weight, morepreferably from 0.5 to 9 parts by weight, most preferably from 1 to 8 parts by weight for 100 parts by weight of the coated carbon fiber.

Various methods can be used for mixing the bisimide coated carbon fiber thus obtained and the polyimide resin. For example, the coated carbon fiber is cut into a length of 3 to 8 mm. The cut fiber thus obtained and the polyimide resin can be separately fed to an extruder and melt-mixed, or are previously blended in a mixer such as a Henschel mixer, super mixer and ribbon blender, and successively fed to the extruder. Alternatively, the coated carbon fiber roving can be directly fed to the extruder and mixed with the polyimide resin.

The amount of the bisimide coated carbon fiber and the polyimide resin matrix in the composition of the invention is from 5 to 50 parts by weight, preferably from 10 to 50 parts by weight of the carbon fiber and from 95 to 50 parts by weight, preferably from 90 to 50 parts by weight of the polyimide resin. When the amount of the carbon fiber is less than 5 parts by weight, increase of tensile strength of the resulting resin composition is unfavorably small. When the amount of the carbon fiber exceeds 50 parts by weight, uniform mixing of molten resin composition becomes difficult and melt-flowability is severely decreased to impair processability such as injection molding ability.

Other additives can be incorporated, if desired, with the composition of the invention in addition to the polyimide resin and the bisimide coated carbon fiber. Exemplary additives include talc, calcium carbonate, mica, glass beads and other fillers, glass fiber, potassium titanate fiber, aramide fiber, ceramic fiber and other fibrous reinforcements, stabilizers and colorants. These additives can be used in an amount giving no adverse effect on the quality and performance of the composition of the invention.

As mentioned above, the resin composition of the invention comprising the bisimide coated carbon fiber and the polyimide resin can be processed into desired articles by injection molding, extrusion forming, transfer molding, compression molding and other known processing methods. The resin composition of the invention thus processed has excellent mechanical strength, at high temperatures in particular, and is hence used for mechanical members and automotive parts which require high mechanical strength at high temperatures, for example, gear, cam, bushing, pulley and sleeve, and also for members of internal combustion engines, for example, gas exhausting parts for a silencer such as an impeller and manifold of an integrated centrifugal compressor, valve guide, valve stem, piston skirt, oil pan, front cover and locker cover.

The carbon fiber reinforced polyimide resin composition of the invention is usually used in the form of pellets which can be handled with ease. Molded articles are prepared by injection molding. The pellets are prepared by kneading and extruding the polyimide resin and the carbon fiber strand with a known single or twin screw extruder and successively by cutting the resulting strand of the composition.

Injection molding of the pellets thus obtained is carried out with a common injection molding machine at a cylinder temperature of 360° to 420° C. and a mold temperature of 160° to 210° C., preferably 180° to 200° C. Complex shaped members of internal combustion engines such as an impeller of an integrated centrifugal compressor can also be prepared with ease.

The present invention will hereinafter be illustrated in detail by way of examples and comparative examples.

EXAMPLE 1

To a reaction vessel equipped with a stirrer, reflux condenser and a nitrogen inlet tube, 368g(1.0 mole) of 4,4'-bis(3-aminophenoxy) biphenyl and 5.215 g of N,N-dimethylacetamide were charged, and 311 g(2.1 moles) of phthalic anhydride was added at room temperature and stirred for 2 hours.

Successively, 404 g(4 moles) of triethyl amine and 306 g(3 moles) of acetic anhydride were added dropwise to the resulting solution and stirred for 2 hours. The slurry thus formed was poured into methanol. The precipitate was filtered, dispersed in methanol, and filtered again. The procedures were repeated again. The filtered precipitate was dried at 150° C. for 2 hours to obtain 475 g of white powder. The powder had a melting point of 286° C. by DSC, a melt-initiation temperature of about 280° C. and good melt processability.

Results of elemental analysis were as follows.

| Elemental analysis ($C_{40}H_{24}N_2O_6$) | | | |
|---|---|---|---|
| | C | H | N |
| Calculated (%) | 76.40 | 3.82 | 4.46 |
| Found (%) | 76.27 | 3.80 | 4.49 |

An IR-absorption spectrum atlas is illustrated in FIG. 1. In the spectrum atlas, characteristic absorption band of imide at around 1780 $cm^{-1}$ and 1720 $cm^{-1}$ and characteristic absorption band of ether at around 1240 $cm^{-1}$ were remarkably found.

According to the identification by the preparation process, results of elemental analysis and IR absorption spectrum atlas, the powder thus obtained was bisimide having the structure of the formula(20): The bisimide had solubility of 5% by weight or

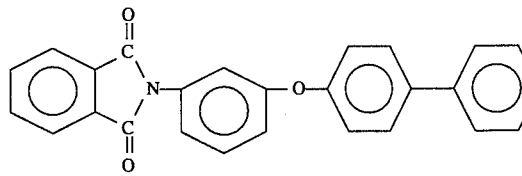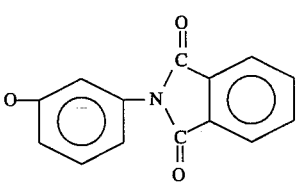

(20)

more in dichloromethane, chloroform and carbon tetrachloride, and also had good processability.

EXAMPLES 2–4

Each bisimide powder was prepared by carrying out the same procedures as conducted in Example 1 except that diamines were used as illustrated in Table 1.

The melting point and results of elemental analysis on the powder thus obtained are illustrated in Table 1

Any bisimide compound had solubility of 5% by weight or more in dichloromethane, chloroform and carbon tetrachloride and also had good processability.

TABLE 1

| Example | Diamine Amount g (mole) | Melting point (°C.) |
|---|---|---|
| 2 | bis[4-(3-aminophenoxy)phenyl] ketone 396.5 (1.0) | 270 |
| 3 | bis(4-(3-aminophenoxy)phenyl]-sulfide 400.5 (1.0) | 230 |
| 4 | 2,2'-bis[4-(3-aminophenoxy)phenyl] propane 410.5 (1.0) | 250 |

| | Elemental analysis (%) | | | |
|---|---|---|---|---|
| | C | H | N | S |
| Calculated | 75.00 | 3.66 | 4.27 | 0 |
| Found | 74.85 | 3.60 | 4.31 | 0 |
| Calculated | 72.70 | 3.64 | 4.24 | 4.85 |
| Found | 72.56 | 3.60 | 4.34 | 4.88 |
| Calculated | 77.01 | 4.48 | 4.18 | 0 |
| Found | 76.92 | 4.42 | 4.21 | 0 |

COMPARATIVE EXAMPLE 1

The same procedures were carried out as conducted in Example 1 except that 368 g of 4,4'-bis(3-aminophenoxy)biphenyl was replaced by 195.6 g(2.1 moles) of aniline and 311 g of phthalic anhydride was replaced by 218.1 g(2.1 moles) of pyromellitic dianhydride. Light yellow powder thus obtained was 360 g.

Results on the elemental analysis of the powder are as follows.

| Elemental analysis ($C_{22}H_{12}N_2O_4$) | | | |
|---|---|---|---|
| | C | H | N |
| Calculated (%) | 71.74 | 3.26 | 7.61 |
| Found (%) | 71.70 | 3.20 | 7.65 |

Figure 2:
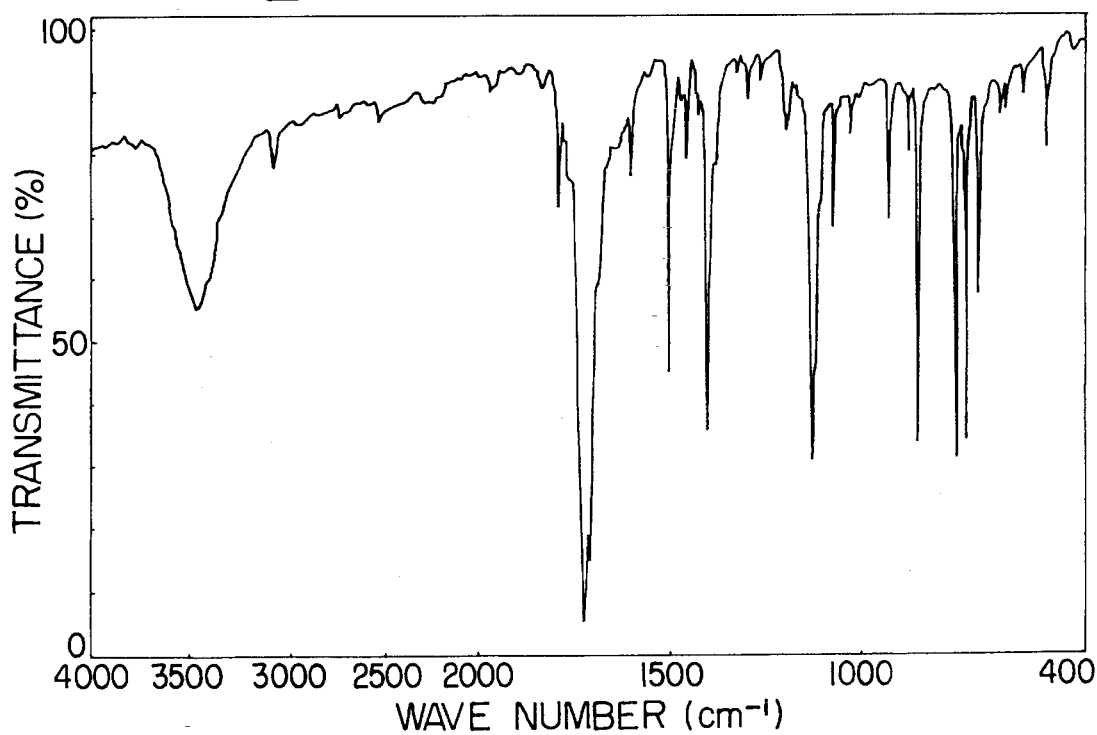
FIG. 2 is an IR absorption spectrum atlas of bisimide obtained in Comparative Example 1.

An IR absorption spectrum of the powder is illustrated in FIG. 2. In the spectrum atlas, the characteristic absorption band of imide around 1780 cm$^{-1}$ and 1720 cm$^{-1}$, and the characteristic absorption band of ether around 1240 cm$^{-1}$ were remarkably found.

According to the identification by the preparation process, results of elemental analysis and IR absorption spectrum atlas, the powder thus obtained was bisimide having the structure of the formula(21): The bisimide had solubility of 0.01% by weight or

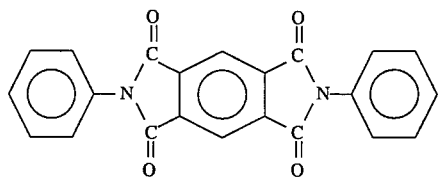

(21)

less in dichloromethane, chloroform and carbon tetrachloride, was poor in processability and had a very high melting point of 442° C.

EXAMPLE 5

To the same reaction vessel as used in Example 1, 212 g(1.0 mole) of 3,3'-diaminobenzophenone and 5215 g of N,N-dimethylacetamide were charged and 311 g(2.1 moles) of phthalic anhydride was added at room temperature and stirred for 2 hours.

Successively, 404 g(4 moles) of triethylamine and 306 g(3 moles) of acetic anhydride were added dropwise to the resultant solution and stirred for 2 hours at room temperature. The reaction mixture was poured into methanol. The precipitate was filtered, dispersed in methanol and filtered again. The procedures were repeated again. The precipitate thus obtained was dried at 150° C. for 2 hours. White powder thus obtained was 453 g, had a melting point of 240° C. and a melt initiation point of about 230° C., and was good in melt processability.

Results on the elemental analysis are as follows.

| Elemental analysis ($C_{29}H_{16}N_2O_5$) | | | |
|---|---|---|---|
| | C | H | N |
| Calculated (%) | 73.73 | 3.39 | 5.93 |
| Found (%) | 73.61 | 3.30 | 5.96 |

Figure 3:
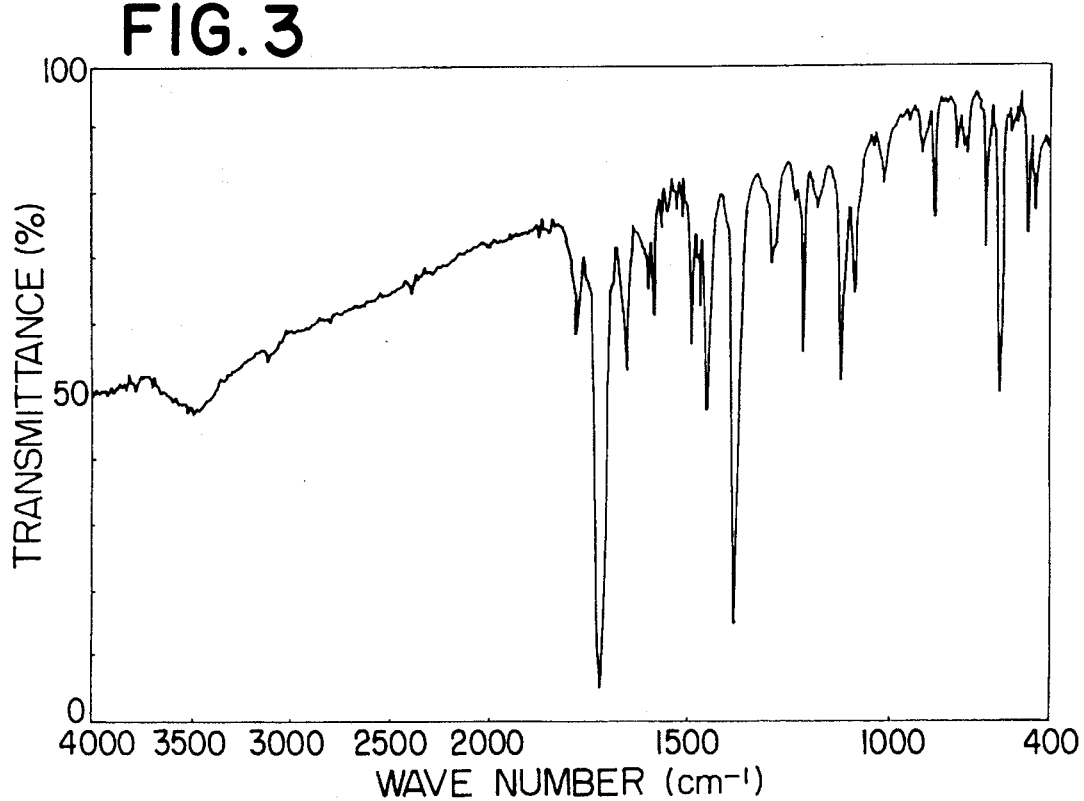
FIG. 3 is an IR absorption spectrum atlas of bisimide obtained in Example 5.

An IR absorption spectrum of the powder is illustrated in FIG. 3. In the spectrum atlas, characteristic absorption band of imide around 1780 cm$^{-1}$ and 1720 cm$^{-1}$ was remarkably observed.

According to the identification by the preparation process, results of elemental analysis and IR absorption spectrum, the powder thus obtained was bisimide having the structure of the formula(22):

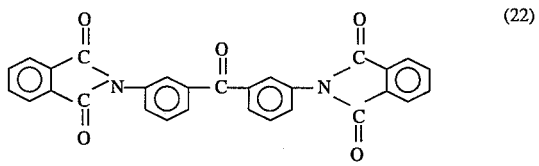

(22)

The bisimide had solubility of 5% by weight or more in dichloromethane, chloroform and carbon tetrachloride, and also had good processability.

EXAMPLE 6

To the same reaction vessel as used in Example 1, 616.7 g(1.0 mole) of bis[4-{4-(4-aminophenoxy)phenoxy}phenyl] sulfone and 1850 g of m-cresylic acid were charged, and 325.6 g(2.2 moles) of phthalic anhydride was added at room temperature. The mixture was heated to 140° C. and reacted for 2 hours.

Successively, the reaction mixture was poured into methanol and resulting precipitate was filtered, washed 3 times with methanol and dried at 150° C. for 2 hours to obtain 873.7 g(96.4% yield) of white powder having a melting point of 217° C.

Following results were obtained on elemental analysis.

| Elemental analysis ($C_{52}H_{32}N_2S_1O_{10}$) | | | | |
|---|---|---|---|---|
| | C | H | N | S |
| Calculated (%) | 71.2 | 3.6 | 3.2 | 3.6 |
| Found (%) | 70.8 | 3.7 | 3.3 | 3.6 |

Figure 4:
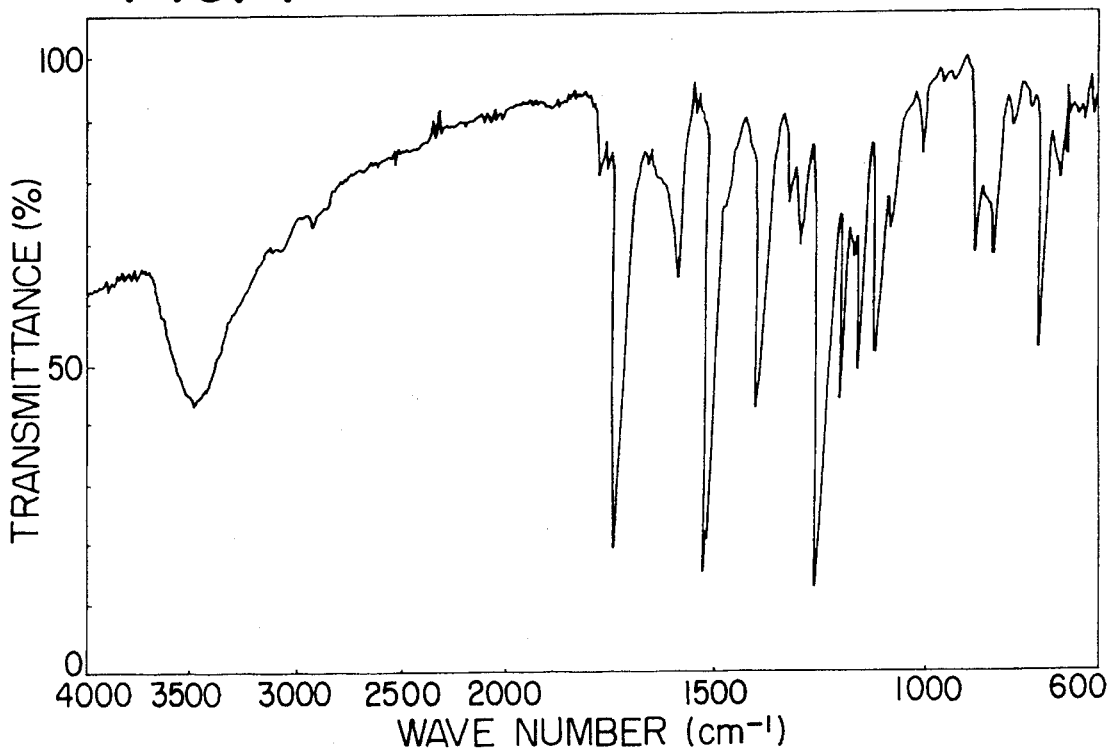
FIG. 4 is an IR absorption spectrum atlas of bisimide obtained in Example 6.

An IR absorption spectrum of the powder is illustrated in FIG. 4. In the spectrum atlas, the characteristic absorption spectrum of imide around 1780 cm$^{-1}$ and 1720 cm$^{-1}$ was remarkably found.

According to the identification by the preparation process, results of elemental analysis and IR absorption spectrum, the powder thus obtained was bisimide having the structure of the formula(23):

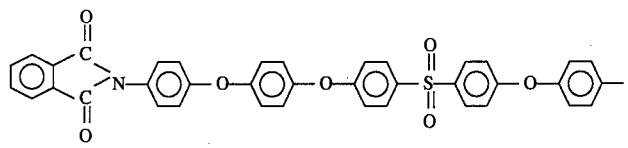

(23)

The bisimide thus obtained had solubility of 5% by weight or more in dichloromethane, chloroform and carbon tetrachloride and also had good processability.

EXAMPLE 7

The same procedures as conducted in Example 6 were carried out except that 325.6 g(2.2 moles) of phthalic anhydride was replaced by 436 g(2.2 moles) of 2,3-naphthalenedicarboxylic anhydride. White powder thus obtained was 938 g(96% yield) and had a melting point of 218° C. Following results were obtained on the elemental analysis.

| Elemental analysis ($C_{60}H_{36}N_2S_1O_{10}$) | | | | |
|---|---|---|---|---|
| | C | H | N | S |
| Calculated (%) | 73.8 | 3.7 | 2.9 | 3.3 |
| Found (%) | 73.6 | 3.5 | 3.0 | 3.3 |

In an IR absorption spectrum atlas, characteristic absorption band of imide around 1780 cm$^{-1}$ and 1720 cm$^{-1}$ was remarkably found.

According to the identification by the preparation process, results of elemental analysis and IR absorption spectrum, the powder thus obtained was bisimide having the structure of the formula(24):

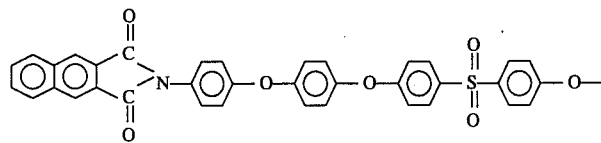

(24)

The bisimide had solubility of 5% by weight or more in dichloromethane, chloroform and carbon tetrachloride and also had good processability.

EXAMPLE 8

To the same reaction vessel as used in Example 1, 344.5 g(1.0 mole) of 1,3-bis(4-amino-α,α-dimethylbenzyl)benzene and 3426 g of m-cresylic acid were charged and 325.6 g(2.2 moles) of phthalic anhydride was added at room temperature. The mixture was heated to 140° C. and reacted for 2 hours. Successively, the reaction mixture was poured into methanol. The precipitate was filtered, washed several times with methanol and dried at 100° C. for 16 hours under reduced pressure. White powder thus obtained was 590.6 g(97.7% yield) and had a melting point of 240° C. Following results were obtained on elemental analysis.

| Elemental analysis ($C_{40}H_{32}N_2O_4$) | | | |
|---|---|---|---|
| | C | H | N |
| Calculated (%) | 79.47 | 5.30 | 4.64 |
| Found (%) | 79.73 | 5.43 | 4.60 |

Figure 5:
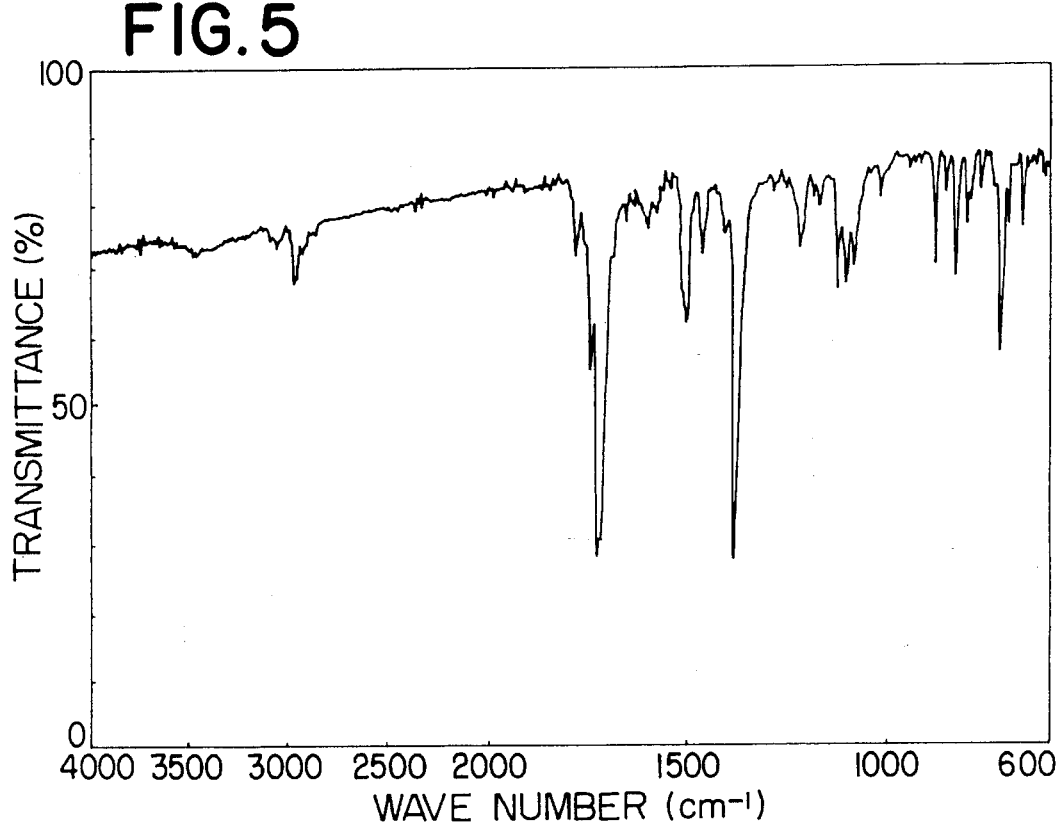
FIG. 5 is an IR absorption spectrum of bisimide obtained in Example 8.

An IR absorption spectrum atlas is illustrated in FIG. 5. In the spectrum atlas, the characteristic absorption band of imide around 1780 cm$^{-1}$ and 1720 cm$^{-1}$ was remarkably found. On the other hand, the characteristic absorption band of amic acid around 1550 cm$^{-1}$, the characteristic absorption band of diamine around 3200–3400 cm$^{-1}$, and the characteristic absorption band of acid anhydride around 1850 cm$^{-1}$ were not found.

According to the identification by the preparation process, results of elemental analysis and IR absorption spectrum, the powder thus formed is bisimide having the structure of the formula(25):

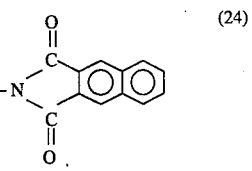

(25)

The bisimide had a solubility of 5% by weight or more in dichloromethane, chloroform and carbon tetrachloride, and also had good processability.

EXAMPLE 9

The same procedures as conducted in Example 8 were carried out except that 325.6 g(2.2 moles) of phthalic anhydride was replaced by 436 g(2.2 moles) of 2,3-naphthalenedicarboxylic anhydride. White powder obtained was 687 g(97% yield), had a melting point of 241° C., and gave following results on elemental analysis.

| Elemental analysis ($C_{48}H_{40}N_2O_4$) | | | |
|---|---|---|---|
| | C | H | N |
| Calculated (%) | 81.36 | 5.65 | 3.95 |
| Found (%) | 81.05 | 5.58 | 3.94 |

In an IR absorption spectrum atlas, characteristic absorption band of imide around 1780 $cm^{-1}$ and 1720 $cm^{-1}$ was remarkably found. On the other hand, characteristic absorption band of amic acid around 1550$cm^{-1}$, characteristic absorption band of diamine around 3200– 3400 $cm^{-1}$, and characteristic absorption band of acid anhydride around 1850 $cm^{-1}$ were not found.

According to the identification by the preparation process, results of elemental analysis and IR absorption spectrum atlas, the powder thus obtained is bisimide having the structure of the formula(26): The bisimide had a solubility of 5% by weight or

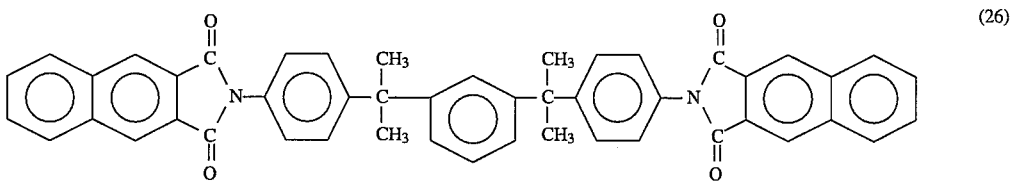
(26)

more in dichloromethane, chloroform and carbon tetrachloride and also had good processability.

EXAMPLE 10

To the same reaction vessel as used in Example 1, 592.7 g(1.0 mole) of bis[3-{4-(4-aminophenoxy)benzoyl}phenyl] ether and 4832 g of m-cresylic acid were charged and 325.6 g(2.2 moles) of phthalic anhydride was added at room temperature. The mixture was heated to 140° C. and reacted for 2 hours.

Successively, the reaction mixture was poured into methanol. The precipitate formed was filtered, washed several times with methanol and dried at 100° C. for 16 hours under reduced pressure.

Yellow powder thus obtained was 820.3 g(96.2% yield). The powder had a melting point of 202° C.

Following results were obtained on the elemental analysis of the powder.

| Elemental analysis ($C_{54}H_{32}N_2O_9$) | | | |
|---|---|---|---|
| | C | H | N |
| Calculated (%) | 76.06 | 3.76 | 3.29 |
| Found (%) | 76.18 | 3.85 | 3.42 |

Figure 6:
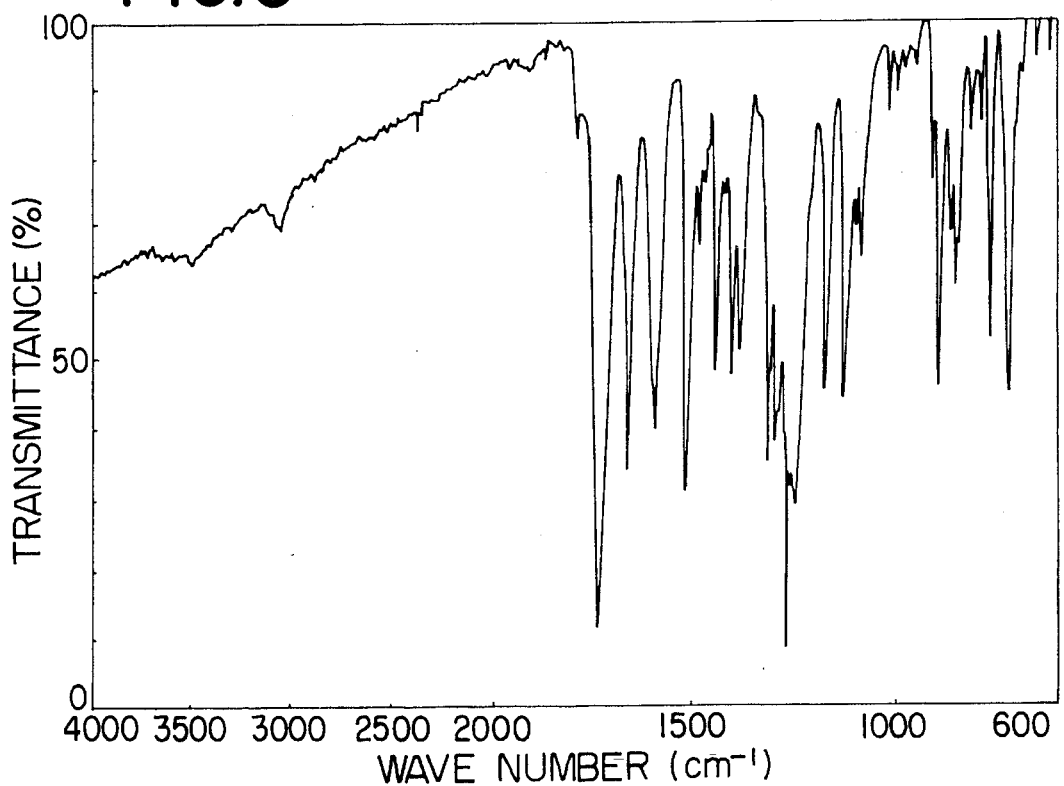
FIG. 6 is an IR absorption spectrum atlas of bisimide obtained in Example 10.

An IR absorption spectrum atlas is illustrated in FIG. 6. In the spectrum atlas, the characteristic absorption band of imide around 1780 $cm^{-1}$ and 1720 $cm^{-1}$ was remarkably found. On the other hand, the characteristic absorption band of amic acid around 1550 $cm^{-1}$, the characteristic absorption band of diamine around 3200–3400 $cm^{-1}$, and the characteristic absorption band of acid anhydride around 1850 $cm^{-1}$ were not found.

According to the identification by the preparation process, results of elemental analysis and IR absorption spectrum, the powder thus formed is bisimide having the structure of the formula(27):

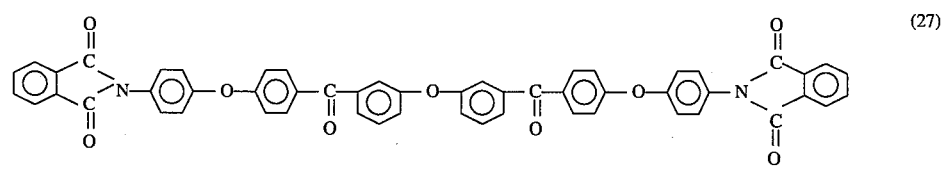
(27)

The bisimide had a solubility of 5% by weight or more in dichloromethane, chloroform and carbon tetrachloride, and also had good processability.

EXAMPLE 11

The same procedures as conducted in Example 10 were carried out except that 325.6 g(2.2 moles) of phthalic anhydride was replaced by 436 g(2.2 moles) of 2,3-naphthalenedicarboxylic anhydride. Yellow powder obtained was 909 g(95% yield), had a melting point of 176° C., and gave following results on elemental analysis.

| Elemental analysis ($C_{62}H_{32}N_2O_9$) | | | |
|---|---|---|---|
| | C | H | N |
| Calculated (%) | 77.82 | 3.35 | 2.93 |
| Found (%) | 77.68 | 3.45 | 3.02 |

In an IR absorption spectrum atlas, characteristic absorption band of imide around 1780 $cm^{-1}$ and 1720 $cm^{-1}$ was remarkably found. On the other hand, characteristic absorption band of amic acid around 1550 $cm^{-1}$, characteristic absorption band of diamine around 3200–3400 $cm^{-1}$, and characteristic absorption band of acid anhydride around 1850 $cm^{-1}$ were not found.

According to the identification by the preparation process, results of elemental analysis and IR absorption spectrum atlas, the powder thus obtained is bisimide having the structure of the formula(28): The bisimide had a solubility of 5% by weight or

| Elementary analysis ($C_{40}H_{24}N_2O_6$) | | | |
|---|---|---|---|
| | C | H | N |
| Calculated (%) | 76.40 | 3.82 | 4.46 |
| Found (%) | 76.72 | 3.92 | 4.51 |

Figure 7:
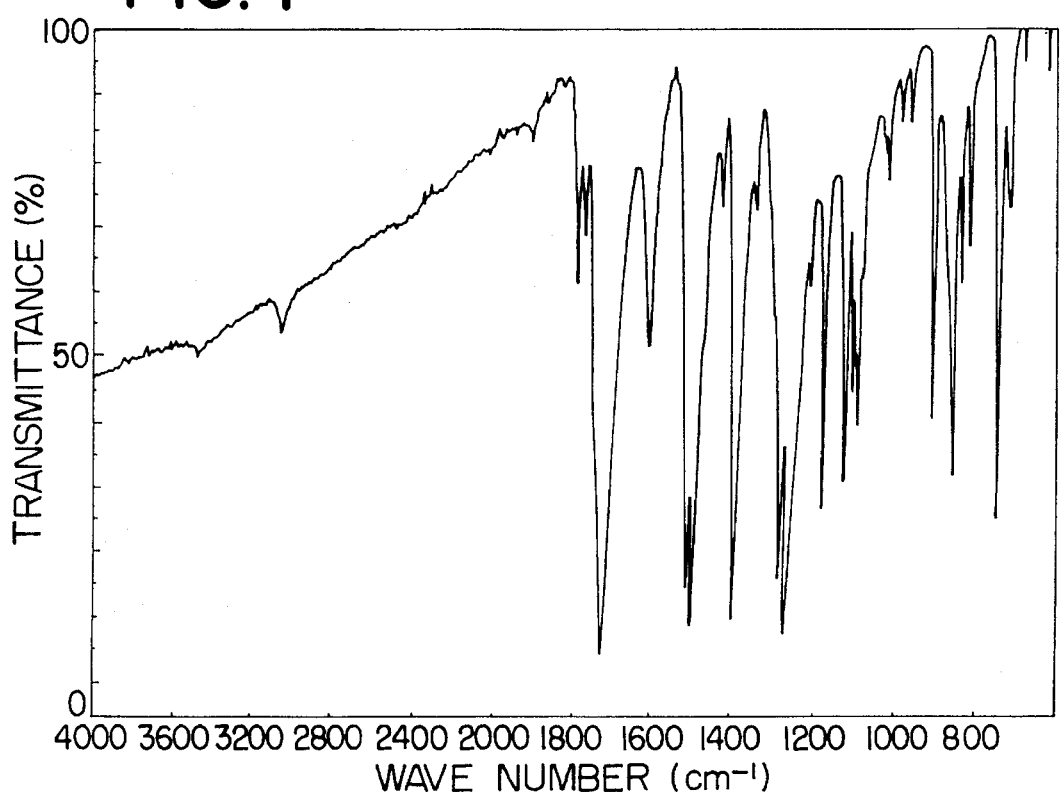
FIG. 7 is an IR absorption spectrum atlas of bisimide obtained in Example 12.

An IR absorption spectrum atlas is illustrated in FIG. 7. In the spectrum atlas, the characteristic absorption band of imide around 1780 $cm^{-1}$ and 1720 $cm^{-1}$ was remarkably found. On the other hand, the characteristic absorption band of amic acid around 1550 $cm^{-1}$, the characteristic absorption band of diamine around 3200–3400 $cm^{-1}$, and the characteristic absorption band of acid anhydride around 1850 $cm^{-1}$ were not found.

According to the identification by the preparation process, results of elemental analysis and IR absorption spectrum, the powder thus formed is bisimide having the structure of the formula(29):

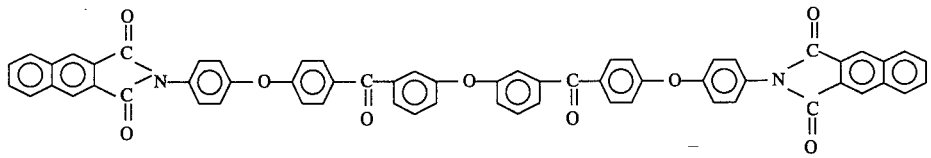

(28)

more in dichloromethane, chloroform and carbon tetrachloride and also had good processability.

EXAMPLE 12

To the same reaction vessel as used in Example 1, 368.4 g(1.0 mole) of 4,4'-bis(4-aminophenoxy)biphenyl and 3561 g of m-cresol were charged and 325.6 g(2.2 moles) of phthalic anhydride was added at room temperature. The mixture was heated to 140° C. and reacted for 2 hours.

Successively, the reaction mixture was poured into methanol. The precipitate formed was filtered, washed several times with methanol and dried at 100° C. for 16 hours under reduced pressure.

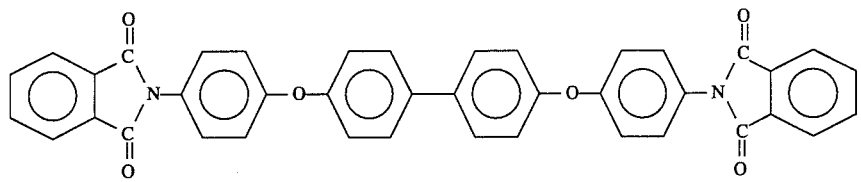

(29)

Yellow powder thus obtained was 600.1 g(95.5% yield). The powder had a melting point of 292° C.

Following results were obtained on the elemental analysis of the powder.

The bisimide had a solubility of 5% by weight or more in dichloromethane, chloroform and carbon tetrachloride, and also had good processability.

EXAMPLE 13

The same procedures as conducted in Example 12 were carried out except that 325.6 g(2.2 moles) of phthalic anhydride was replaced by 436 g(2.2 moles)of 2,3-naphthalenedicarboxylic anhydride. Light yellow powder obtained was 696 g(95% yield), had a melting point of 293° C., and gave following results on elemental analysis.

| Elemental analysis (C₄₈H₃₂N₂O₆) | | | |
|---|---|---|---|
| | C | H | N |
| Calculated (%) | 78.69 | 4.37 | 3.83 |
| Found (%) | 78.70 | 4.28 | 3.61 |

In an IR absorption spectrum atlas, characteristic absorption band of imide around 1780 cm$^{-1}$ and 1720 cm$^{-1}$ was remarkably found.

On the other hand, characteristic absorption band of amic acid around 1550 cm$^{-1}$, characteristic absorption band of diamine around 3200–3400 cm$^{-1}$, and characteristic absorption band of acid anhydride around 1850 cm$^{-1}$ were not found.

According to the identification by the preparation process, results of elemental analysis and IR absorption spectrum atlas, the powder thus obtained is bisimide having the structure of the formula(30): The bisimide had a solubility of 5% by weight or

| Elementary analysis (C₄₃H₃₀N₂O₆) | | | |
|---|---|---|---|
| | C | H | N |
| Calculated (%) | 77.01 | 4.48 | 4.18 |
| Found (%) | 76.84 | 4.55 | 4.26 |

Figure 8:
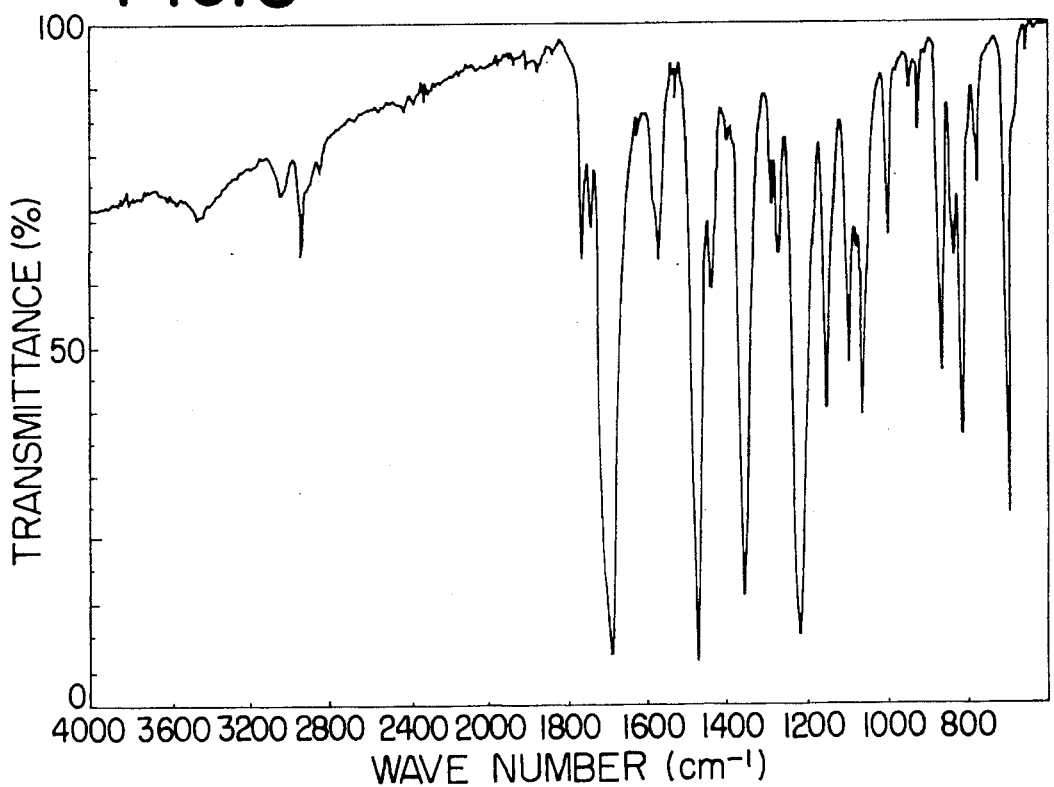
FIG. 8 is an IR absorption spectrum atlas of bisimide obtained in Example 14.

An IR absorption spectrum atlas is illustrated in FIG. 8. In the spectrum atlas, the characteristic absorption band of imide around 1780cm$^{-1}$ and 1720 cm$^{-1}$ was remarkably found. On the other hand, the characteristic absorption band of amic acid around 1550 cm$^{-1}$, the characteristic absorption band of diamine around 3200–3400 cm$^{-1}$, and the characteristic absorption band of acid anhydride around 1850 cm$^{-1}$ were not found.

According to the identification by the preparation process, results of elemental analysis and IR absorption spectrum, the powder thus formed is bisimide having the structure of the formula(31):

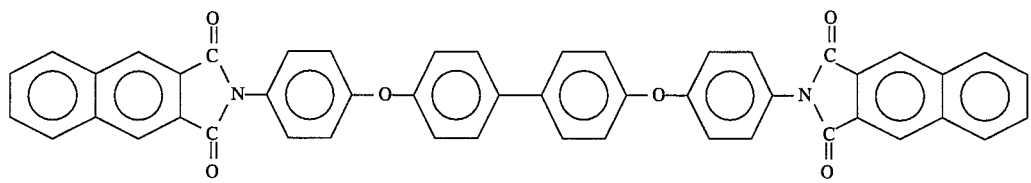

(30)

more in dichloromethane, chloroform and carbon tetrachloride and also had good processability.

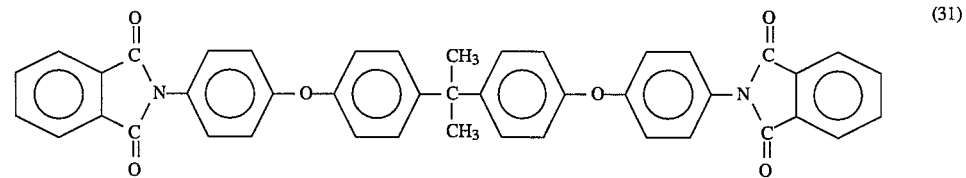

(31)

EXAMPLE 14

To the same reaction vessel as used in Example 1, 410.5 g(1 mole) of 2,2-bis[4-(4-aminophenoxy)phenyl]propane, and 3800 g of m-cresol were charged and 325.6 g(2.2 moles) of phthalic anhydride was added at room temperature. The mixture was heated to 140° C. and reacted for 2 hours.

Successively, the reaction mixture was poured into methanol. The precipitate formed was filtered, washed several times with methanol and dried at 100° C. for 16 hours under reduced pressure.

Light yellow powder thus obtained was 612.8 g(91.4% yield). The powder had a melting point of 218° C.

Following results were obtained on the elemental analysis of the powder.

The bisimide had a solubility of 5% by weight or more in dichloromethane, chloroform and carbon tetrachloride and also had good processability.

EXAMPLE 15

The same procedures as conducted in Example 14 were carried out except that 325.6 g(2.2 moles) of phthalic anhydride was replaced by 436 g(2.2 moles) of 2,3-naphthalenedicarboxylic anhydride. White powder obtained was 697 g(90% yield), had a melting point of 219° C., and gave following results on elemental analysis.

| Elementary analysis (C$_{51}$H$_{38}$N$_2$O$_6$) | | | |
|---|---|---|---|
| | C | H | N |
| Calculated (%) | 79.07 | 4.91 | 3.62 |
| Found (%) | 78.72 | 5.05 | 3.54 |

In an IR absorption spectrum atlas, characteristic absorption band of imide around 1780 cm$^{-1}$ and 1720 cm$^{-1}$ was remarkably found. On the other hand, characteristic absorption band of amic acid around. 1550 cm$^{-1}$, characteristic absorption band of diamine around 3200–3400 cm$^{-1}$, and characteristic absorption band of acid anhydride around 1850 cm$^{-1}$ were not found.

According to the identification by the preparation process, results of elemental analysis and IR absorption spectrum atlas, the powder thus obtained is bisimide having the structure of the formula(32): The bisimide had a solubility of 5% by weight or

| Elemental analysis (C$_{40}$H$_{24}$N$_2$O$_6$S) | | | | |
|---|---|---|---|---|
| | C | H | N | S |
| Calculated (%) | 72.70 | 3.64 | 4.24 | 4.85 |
| Found (%) | 72.66 | 3.73 | 4.26 | 4.99 |

Figure 9:
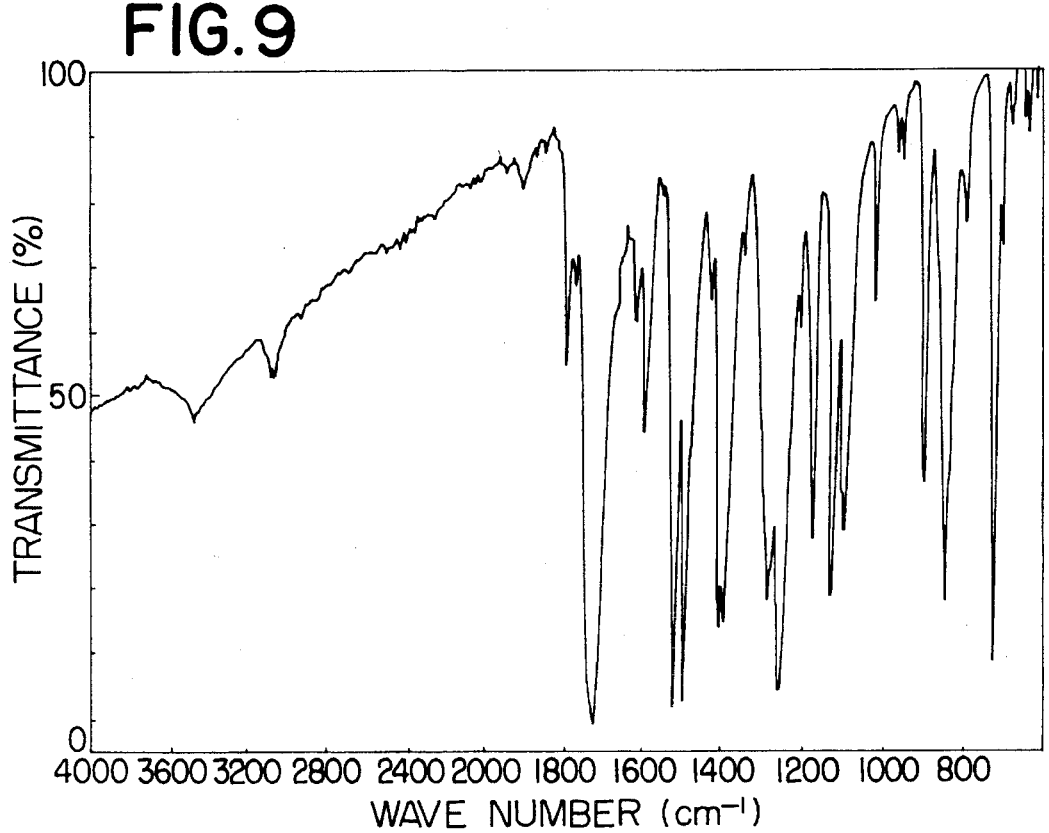
FIG. 9 is an IR absorption spectrum atlas of bisimide obtained in Example 16.

An IR absorption spectrum atlas is illustrated in FIG. 9. In the spectrum atlas, the characteristic absorption band of imide around 1780 cm$^{-1}$ and 1720 cm$^{-1}$ was remarkably found. On the other hand, the characteristic absorption band of amic acid around 1550 cm$^{-1}$, the characteristic absorption band of diamine around 3200–3400 cm$^{-1}$, and the characteristic absorption band of acid anhydride around 1850 cm$^{-1}$ were not found.

According to the identification by the preparation process, results of elemental analysis and IR absorption spectrum, the powder thus formed is bisimide having the structure of the formula(33):

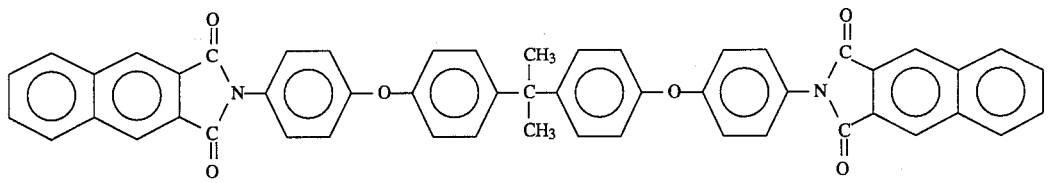

(32)

more in dichloromethane, chloroform and carbon tetrachloride and also had good processability.

EXAMPLE 16

To the same reaction vessel as used in Example 1, 400.5 g(1.0 mole) of bis[4-(4-aminophenoxy)phenyl]sulfide and 3743 g of m-cresol were charged and 325.6 g(2.2 moles) of phthalic anhydride was added at room temperature. The mixture was heated to 140° C. and reacted for 2 hours.

Successively, the reaction mixture was poured into methanol. The precipitate formed was filtered, washed several times with methanol and dried at 100° C. for 16 hours under reduced pressure.

White powder thus obtained was 612.9 g(92.8% yield). The powder had a melting point of 252° C.

Following results were obtained on the elemental analysis of the powder.

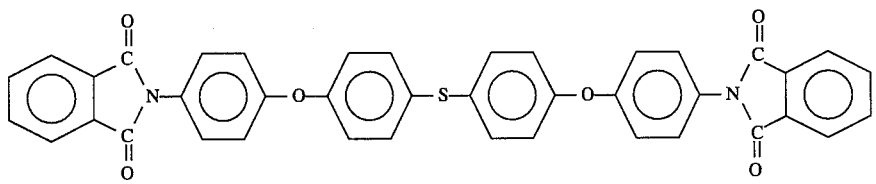

(33)

The bisimide had a solubility of 5% by weight or more in dichloromethane, chloroform and carbon tetrachloride, and also had good processability.

EXAMPLE 17

The same procedures as conducted in Example 16 were carried out except that 325.6 g(2.2 moles) of phthalic anhydride was replaced by, 436 g(2.2 moles) of 2,3-naphthalenedicarboxylic anhydride. White powder obtained was 703 g(92% yield), had a melting point of 253 , and gave following results on elemental analysis.

| Elemental analysis ($C_{48}H_{32}N_2O_6S$) | | | | |
|---|---|---|---|---|
| | C | H | N | S |
| Calculated (%) | 75.39 | 4.19 | 3.66 | 4.19 |
| Found (%) | 75.52 | 4.26 | 3.42 | 3.88 |

In an IR absorption spectrum atlas, characteristic absorption band of imide around 1780 $cm^{-1}$ and 1720 $cm^{-1}$ was remarkably found. On the other hand, characteristic absorption band of amic acid around 1550 $cm^{-1}$, characteristic absorption band of diamine around 3200–3400 $cm^{-1}$, and characteristic absorption band of acid anhydride around 1850 $cm^{-1}$ were not found.

According to the identification by the preparation process, results of elemental analysis and IR absorption spectrum atlas, the powder thus obtained is bisimide having the structure of the formula(34): The bisimide had a solubility of 5% by weight or more in dichloromethane, chloroform and carbon tetrachloride and also had good processability.

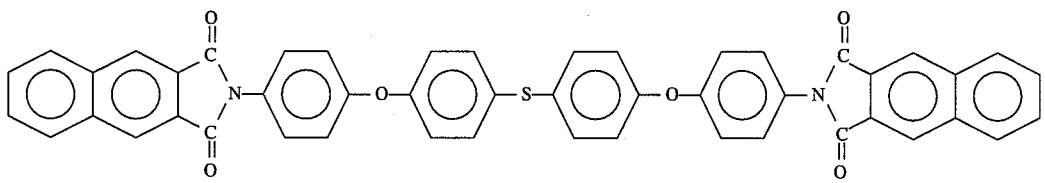

(34)

SYNTHESIS EXAMPLE

Synthesis of Polyimide-1

According to the example described Japanese Laid-Open Patent Hei 2-18419, 3,3'-diaminobenzophenone was reacted with 3,3',4,4'-benzophenonetetracarboxylic dianhydride in the presence of phthalic anhydride to obtain polyimide powder.

The polyimide powder had an inherent viscosity of 0.52 dl/g, glass transition temperature of 250° C. and melting point of 298° C.

The inherent viscosity was measured at 35° C. in a solution containing 0.5 g of the polyimide in a solvent mixture of p-chlorophenol/phenol in a ratio of 90/10 by weight. The melting point was measured by DSC. The measuring methods will be the same hereinafter.

Synthesis of Polyimide-2

The same procedures as conducted in Synthesis of Polyimide-1 were carried out except that the ratio of the diamine to the tetracarboxylic acid dianhydride and phthalic anhydride was changed. The polyimide powder thus obtained had an inherent viscosity of 0.85 dl/g, glass transition temperature of 262° C. and melting point of 298° C.

Synthesis of Polyimide-3

According to the description in Japanese Laid-Open Patent Hei 1-110530, 4,4'-bis(3-aminophenoxy)biphenyl was reacted with pyromellitic dianhydride and phthalic anhydride to obtain polyimide powder.

The polyimide powder obtained had an inherent viscosity of 0.53 dl/g, glass transition temperature of 250° C. and melting point of 390° C.

Synthesis of Polyimide-4

The same procedures as conducted in Synthesis of Polyimide-3 were carried out except that the ratio of the diamine to tetracarboxylic acid dianhydride and phthalic anhydride was changed.

The polyimide powder thus obtained had an inherent viscosity of 0.78 dl/g, glass transition temperature of 254° C. and melting point of 390° C.

Synthesis of Polyimide-5

The same procedures as conducted in Synthesis of Polyimide-3 were carried out by using bis[4-(3-aminophenoxy)phenyl]sulfide, pyromellitic dianhydride and phthalic anhydride.

The polyimide thus obtained had an inherent viscosity of 0.49 dl/g and glass transition temperature of 235° C.

Synthesis of Polyimide-6

The same procedures as conducted in Synthesis of Polyimide-3 were carried out by using bis[4-(3-aminophenoxy)phenyl]ketone, bis(3,4-dicarboxyphenyl)ether dianhydride and phthalic anhydride.

The polyimide thus obtained had an inherent viscosity of 0.51 dl/g and glass transition temperature of 201° C.

Synthesis of Polyimide-7

According to Japanese Laid-Open Patent Hei 1-221428, bis[4-{4-(4-aminophenoxy)phenoxy}phenyl]sulfone was reacted with pyromellitic dianhydride and phthalic anhydride.

The polyimide thus obtained had an inherent viscosity of 0.57 dl/g, glass transition temperature of 285° C. and melting point of 420° C.

Synthesis of Polyimides-8–12

The same procedures as conducted in Synthesis of Polyimide-7 were carried out except that tetracarboxylic acid dianhydride was changed to obtain various kinds of polyimide.

The raw materials and properties of these polyimides and the results on Polyimide-7 are summarized in Table 2.

TABLE 2

| Polyimide | Raw Material | | |
|---|---|---|---|
| | Diamine | Tetracarboxylic acid dianhydride | Dicarboxylic acid anhydride |
| 7 | bis[4-{4-(4-aminophenoxy) | pyromellitic dianhydride | phthalic anhydride |

TABLE 2-continued

| | phenoxy} phenyl]sulfone | | |
|---|---|---|---|
| 8 | ↑ | ↑ | ↑ |
| 9 | ↑ | 3,3[40 ,4,4'-biphenyl-tetracarboxylic dianhydride | ↑ |
| 10 | ↑ | bis(3,4-dicarboxy-phenyl)ether dianhydride | ↑ |
| 11 | ↑ | 3,3',4,4'-benzophenone-tetracarboxylic dianhydride | ↑ |
| 12 | ↑ | 4,4'-(p-phenylenedioxy) diphthalic dianhydride | ↑ |

| | Polymer properties | | |
|---|---|---|---|
| Polyimide | Inherent viscosity (dl/g) | Glass transition temperature (°C.) | Melting point (°C.) |
| 7 | 0.57 | 285 | 420 |
| 8 | 0.70 | 288 | 420 |
| 9 | 0.60 | 263 | — |
| 10 | 0.59 | 237 | — |
| 11 | 0.60 | 245 | — |
| 12 | 0.59 | 220 | — |

Synthesis of Bisimide Compound-1

Bisimide was prepared from 4,4'-bis(3-aminophenoxy)biphenyl and phthalic anhydride by carrying out the same procedures as Example 1. The bisimide compound obtained had a melting point of 286° C.

Synthesis of Bisimide Compound-2

Bisimide was prepared from bis[4-(3-aminophenoxy)phenyl]sulfide and phthalic anhydride by the same procedures as conducted in Synthesis of Bisimide Compound-1.

The bisimide compound thus obtained had a melting point of 230° C.

Synthesis of Bisimide Compound-3

To a reaction vessel equipped with a stirrer, reflux condenser and nitrogen inlet tube, 200 g(1.0 mole) of 4,4'-diaminodiphenyl ether and 4000 g of m-cresol were charged and 311 g(2.1 moles) of phthalic anhydride was added at room temperature. The mixture was then heated to 200° C. and stirred for 2 hours at the same temperature.

Successively, the reaction mixture was poured into methanol. The precipitate formed was filtered, washed several times with methanol and dried at 150° C. for 2 hours. The white powder thus obtained was 450 g, had a melting point of 295° C. and melt-initiation point of about 290° C., and also had good melt-processability.

Following results were obtained on elemental analysis.

| Elemental analysis ($C_{28}H_{16}N_2O_4$) | | | |
|---|---|---|---|
| | C | H | N |
| Calculated (%) | 73.36 | 3.06 | 6.11 |
| Found (%) | 73.30 | 3.10 | 6.16 |

Figure 10:
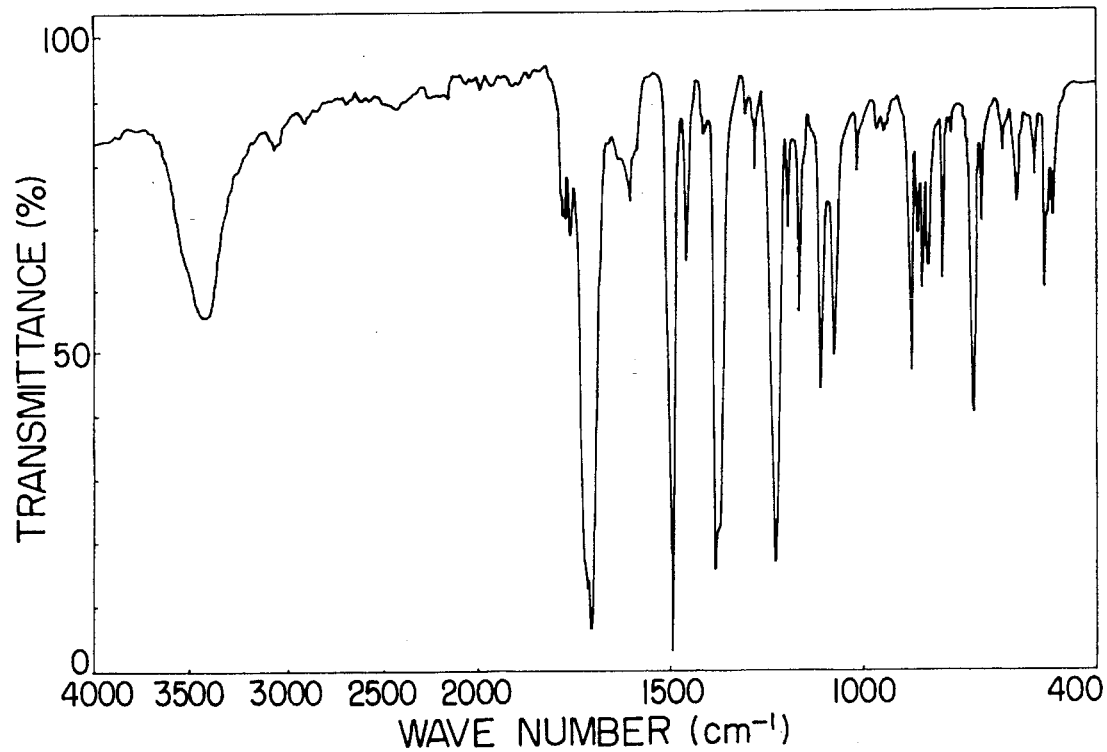
FIG. 10 is an IR absorption spectrum atlas of bisimide-3 obtained in the Synthesis Example.

An IR absorption spectrum atlas is illustrated in FIG. 10.

In the spectrum atlas, the characteristic absorption band of imide around 1780 cm$^{-1}$ and 1720 cm$^{-1}$ and the characteristic absorption band of ether around 1240 cm$^{-1}$ were remarkably found.

According to the identification by the preparation process, results of elemental analysis and IR absorption spectrum, the powder thus obtained is bisimide having the structure of the formula(35):

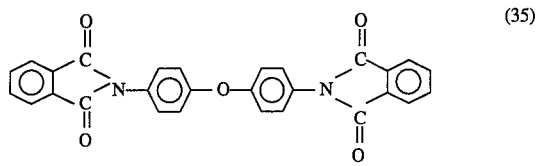

(35)

Synthesis of Bisimide Compound-4

Bisimide was prepared from 3,3 '-diaminobenzophenone and phthalic arthydride by carrying out the same procedures as conducted in Example 5.

The bisimide compound obtained had a melting point of 240° C.

Synthesis of Bisimide Compound-5

Bisimide was prepared from 4,4'-bis(4-aminophenoxy)biphenyl and phthalic anhydride by carrying out the same procedures as conducted Ln Example-12.

Synthesis of Bisimde Compounds-6–12

The same procedures as conducted in Synthesis of Bisimide Compound-5 were carried out except that diamines were changed o obtain various kinds of bLsimide.

Table 3 summarizes he raw materials and properties of the bisimide and also results on Aromatic Bisimide Compound-5.

TABLE 3

| | Raw material | | Bisimide Melting point (°C.) |
|---|---|---|---|
| Bisimide | Diamine | Dicarboxylic acid anhydride | |
| 5 | 4,4'-bis(4-aminophenoxy) biphenyl | Phthalic anhydride | 292 |
| 6 | 2,2-bis[4-(4-aminophenoxy) phenyl]propane | ↑ | 218 |
| 7 | 1,3-bis(4-amino-α, α-dimethylbenzyl)benzene | ↑ | 240 |
| 8 | bis[4- {4-(4-aminophenoxy) phenoxy} phenyl]sulfone | ↑ | 217 |
| 9 | bis[3- {4-(4-aminophenoxy) benzoyl} phenyl]ether | ↑ | 202 |
| 10 | bis[4- {4-(4-amino-α, α-dimethylbenzyl)phenoxy} phenyl]sulfone | ↑ | 160 |
| 11 | 1,4-bis[4-(3-aminophenoxy)-benzoyl]benzene | ↑ | 220 |
| 12 | 1,3- bis[4-(4-aminophenoxy)-α, α-dimethylbenzyl]benzene | ↑ | 180 |

EXAMPLES 18–20, COMPARATIVE EXAMPLE 2

Polyimide-1 and Bisimide Compound-1 were dry blended in proportions illustrated in Table 4. Melt viscosity of the resin composition obtained was measured with a Koka type flow tester CFT-500 (Trade mark of Shimadzu Seisakusho Co.) by using an orifice having a diameter of 0.1 cm and a length of 1 cm. The resin composition was maintained in the cylinder at 380° C. for 5 minutes and then extruded under a load of 100 kg. Results are illustrated in Table 4.

Melt viscosity rapidly decreased with increase in the proportion of the bisimide compound, and thus illustrated improvement of processability.

EXAMPLES 21–23, COMPARATIVE EXAMPLE 3

Polyimide-2 and Bisimide Compound-2 were dry blended in proportions illustrated in Table 4. Melt viscosity of the resulting composition was measured by the same procedures as conducted in Examples 18–20, Comparative Example 2 except that the resin composition was maintained at 400° C. for 5 minutes in the cylinder of the flow tester. Results obtained are illustrated in Table 4.

EXAMPLES 24–26

The same procedures as conducted in Examples 18–20 were carried out except that Bisimide Compound-3 was used in place of Bisimide Compound-1 and dry blended in proportions illustrated in Table 4. Melt viscosity was measured by extruding under 100 kg load after maintaining at 380° C. for 5 minutes. Results are illustrated in Table 4.

TABLE 4

|  | Polyimide (wt. part) |  | Bisimide (wt. part) |  | Melt viscosity (poise) |
|---|---|---|---|---|---|
| Example 18 | Polyimide | 100 | Bisimide | 1 | 8000 |
| Example 19 | -1 | 100 | Compound | 5 | 6300 |
| Example 20 |  | 100 | -1 | 20 | 1800 |
| Comparative Example 2 |  | 100 |  | 0 | 10500 |
| Example 21 | Polyimide | 100 | Bisimide | 2 | 91400 |
| Example 22 | -2 | 100 | Compound | 10 | 51400 |
| Example 23 |  | 100 | -2 | 50 | 2500 |
| Comparative Example 3 |  | 100 |  | 0 | 120000 |
| Example 24 | Polyimide | 100 | Bisimide | 5 | 6400 |
| Example 25 | -1 | 100 | Compound | 20 | 1800 |
| Example 26 |  | 100 | -3 | 70 | **<100 |

**: Melt viscosity is less than 100 poise and a measurement of melt viscosity was not possible.

EXAMPLES 27–32, COMPARATIVE EXAMPLE 4

Polyimide-3 and Bisimide Compound-1 or Bisimide Compound-3 were dry blended in proportions illustrated in Table 5. Melt viscosity of the resin composition obtained was measured with a Koka type flow tester CFT-500 (Trade mark of Shimadzu Seisakusho Co.) by using an orifice having a diameter of 0.1 cm and a length of 1 cm. The resin composition was maintained in the cylinder at 400° C. for 5 minutes and then extruded under a load of 100 kg. Results are illustrated in Table 5.

Melt viscosity rapidly decreased with increase in the proportion of the bisimide compound, and thus illustrated improvement of processability.

EXAMPLES 33–35, COMPARATIVE EXAMPLE 5

Polyimide-5 and Bisimide Compound-2 were dry blended in proportions illustrated in Table 5. Melt viscosity of the resulting composition was measured by the same procedures as conducted in Examples 27–32, Comparative Example 4 except that the resin composition was maintained at 360° C. for 5 minutes in the cylinder of the flow tester. Results obtained are illustrated in Table 5.

EXAMPLE 36–38, COMPARATIVE EXAMPLE 6

Polyimide-6 and Bisimide Compound-1 were dry blended in proportions illustrated in Table 5. Melt viscosity of the resulting composition was measured by extruding under 100 kg load after maintaining at 340° C. for 5 minutes in the cylinder of the flow tester. Results are illustrated in Table 5.

TABLE 5

|  | Polyimide (wt. part) |  | Bisimide (wt. part) |  | Melt viscosity (poise) |
|---|---|---|---|---|---|
| Example 27 | Polyimide | 100 | Bisimide | 1 | 5100 |
| Example 28 | -3 | 100 | Compound | 5 | 3600 |
| Example 29 |  | 100 | -1 | 20 | 1000 |
| Comparative Example 4 |  | 100 |  | 0 | 6000 |
| Example 30 | Polyimide | 100 | Bisimide | 2 | 4900 |
| Example 31 | -3 | 100 | Compound | 10 | 2700 |
| Example 32 |  | 100 | -3 | 50 | 150 |
| Example 33 | Polyimide | 100 | Bisimide | 5 | 5500 |
| Example 34 | -5 | 100 | Compound | 20 | 1500 |
| Example 35 |  | 100 | -2 | 70 | **<100 |
| Comparative Example 5 |  | 100 |  | 0 | 9000 |
| Example 36 | Polyimide | 100 | Bisimide | 1 | 6400 |
| Example 37 | -6 | 100 | Compound | 5 | 4500 |
| Example 38 |  | 100 | -1 | 20 | 1300 |
| Comparative Example 6 |  | 100 |  | 0 | 8000 |

EXAMPLES 39–2, COMPARATIVE EXAMPLE 7

Polyimide-1 and Bisimide Compound-4 were dry blended in proportions illustrated in Table 6. Melt viscosity of the resin composition obtained was measured with a Koka Type flow tester CFT-500 (Trade mark of Shimadzu Seisakusho Co.) by using an orifice having a diameter of 0.1 cm and a length of 1 cm. The resin composition was maintained in the cylinder at 380° C. for 5 minutes and then extruded under a load of 100 kg. Results are illustrated in Table 6.

Melt viscosity rapidly decreased with increase in the proportion of the bisimide compound, and thus illustrated improvement of processability.

EXAMPLES 43–45, COMPARATIVE EXAMPLE 8

Polyimide-2 and Bisimide Compound-4 were dry blended in proportions illustrated in Table 6. Melt viscosity of the resulting composition was measured by the same procedures as conducted in Examples 39–42 except that the resin composition was maintained at 400° C. for 5 minutes in the cylinder of the flow tester. Results are illustrated in Table 6.

TABLE 6

|  | Polyimide (wt. part) |  | Bisimide (wt. part) |  | Melt viscosity (poise) |
|---|---|---|---|---|---|
| Example 39 | Polyimide | 100 | Bisimide | 1 | 8100 |
| Example 40 | -1 | 100 | Compound | 5 | 5700 |
| Example 41 |  | 100 | -4 | 20 | 1600 |
| Example 42 |  | 100 |  | 70 | **<100 |
| Comparative Example 7 |  | 100 |  | 0 | 10500 |

TABLE 6-continued

|  | Polyimide (wt. part) | | Bisimide (wt. part) | | Melt viscosity (poise) |
|---|---|---|---|---|---|
| Example 43 | Polyimide | 100 | Bisimide | 2 | 77000 |
| Example 44 | -2 | 100 | Compound | 10 | 43700 |
| Example 45 |  | 100 | -4 | 50 | 2300 |
| Comparative Example 8 |  | 100 |  | 0 | 120000 |

EXAMPLES 46–51, COMPARATIVE EXAMPLE 9

Polyimide-3 and Bisimide Compound-5 or Bisimide Compound-7 were dry blended in proportions illustrated in Table 7. Melt viscosity of the resin composition obtained was measured with a Koka Type flow tester CFT-500 (Trade mark of Shimadzu Seisakusho Co.) by using an orifice having a diameter of 0.1 cm and a length of 1 cm. The resin composition was maintained in the cylinder at 400° C. for 5 minutes and then extruded under a load of 100 k. Results are illustrated in Table 7.

Melt viscosity rapidly decreased with increase in the proportion of the bisimide compound, and thus illustrated improvement of processability.

EXAMPLES 52–57, COMPARATIVE EXAMPLE 10

Polyimide-4 and Bisimide Compound-5 or Bisimide Compound-11 were dry blended in proportions illustrated in Table 7. Melt viscosity of the resulting composition was measured by the same procedures as conducted in Examples 46–51, Comparative Example 9.

EXAMPLES 58–63, COMPARATIVE EXAMPLE 11

Polyimide-5 and Bisimide Compound-6 or Bisimide Compound-8 were dry blended in proportions illustrated in Table 7. Melt viscosity of resulting polyimide composition was measured by extruding under load of 100 kg after maintaining at 360° C. for 5 minutes in the cylinder of the flow tester. Results are illustrated in Table 7.

EXAMPLES 63–71, COMPARATIVE EXAMPLE 12

Polyimide-6 and Bisimide Compounds-9, -10 or -12 were dry blended in proportions illustrated in Table 7. Melt viscosity of the resulting polyimide composition was measured by extruding under load of 100 kg after maintaining at 340° C. for 5 minutes in the cylinder of the flow tester. Results are illustrated in Table 7.

TABLE 7

|  | Polyimide (wt. part) | | Bisimide (wt. part) | | Melt viscosity (poise) |
|---|---|---|---|---|---|
| Example 46 | Polyimide | 100 | Bisimide | 1 | 5200 |
| Example 47 | -3 | 100 | Compound | 5 | 3500 |
| Example 48 |  | 100 | -5 | 20 | 1100 |
| Comparative Example 9 |  | 100 |  | 0 | 6000 |
| Example 49 |  | 100 | Bisimide | 2 | 4800 |
| Example 50 |  | 100 | Compound | 10 | 2500 |
| Example 51 |  | 100 | -7 | 40 | 200 |
| Example 52 | Polyimide | 100 | Bisimide | 2 | 83000 |
| Example 53 | -4 | 100 | Compound | 10 | 46000 |
| Example 54 |  | 100 | -5 | 25 | 6000 |
| Comparative Example 10 |  | 100 |  | 0 | 370000 |
| Example 55 |  | 100 | Bisimide | 5 | 72000 |
| Example 56 |  | 100 | Compound | 15 | 15000 |
| Example 57 |  | 100 | -11 | 30 | 1300 |
| Example 58 | Polyimide | 100 | Bisimide | 2 | 7400 |
| Example 59 | -5 | 100 | Compound | 10 | 3800 |
| Example 60 |  | 100 | -6 | 15 | 2400 |
| Comparative Example 11 |  | 100 |  | 0 | 9000 |
| Example 61 |  | 100 | Bisimide | 5 | 5800 |
| Example 62 |  | 100 | Compound | 20 | 1500 |
| Example 63 |  | 100 | -8 | 30 | 640 |
| Example 63 | Polyimide | 100 | Bisimide | 2 | 6800 |
| Example 64 | -6 | 100 | Compound | 5 | 5200 |
| Example 65 |  | 100 | -9 | 10 | 3400 |
| Comparative Example 12 |  | 100 |  | 0 | 8000 |
| Example 66 |  | 100 | Bisimide | 10 | 3300 |
| Example 67 |  | 100 | Compound | 20 | 1400 |
| Example 68 |  | 100 | -10 | 55 | **<100 |
| Example 69 |  | 100 | Bisimide | 1 | 7200 |
| Example 70 |  | 100 | Compound | 5 | 5200 |
| Example 71 |  | 100 | -12 | 10 | 3200 |

EXAMPLES 72–77, COMPARATIVE EXAMPLE 13

Polyimide-7 and B is imide Compound-1 or Bisimide Compound-3 were dry blended in proportions illustrated in Table 8. Melt viscosity of the resin composition obtained was measured with a Koka Type flow tester CFT-500 (Trade mark of Shimadzu Seisakusho Co.) by using an orifice having a diameter of 0.1 cm and a length of 1 cm. The resin composition was maintained in the cylinder at 420° C. for 5 minutes and then extruded under a load of 100 kg. Results are illustrated in Table 8.

Melt viscosity rapidly decreased with increase in the proportion of the bisimide compound, and thus illustrated improvement of processability.

EXAMPLES 78–83, COMPARATIVE EXAMPLE 14

Polyimide-8 and Bisimide Compound-5 or Bisimide Compound-7 were dry blended in proportions illustrated in Table 8. Melt viscosity of the resulting composition was measured by the same procedures as conducted in Examples 72–77, Comparative Example 13.

EXAMPLES 84–89, COMPARATIVE EXAMPLE 15

Polyimide-9 and Bisimide Compound-1 or Bisimide Compound-8 were dry blended in proportions illustrated in Table 8. Melt viscosity of resulting polyimide composition was measured by extruding under load of 100 kg after maintaining at 380° C. for 5 minutes in the cylinder of the flow tester. Results are illustrated in Table 8.

EXAMPLES 90–93, COMPARATIVE EXAMPLE 16

Polyimide-10 and Bisimide Compounds-9 or -11 were dry blended in proportions illustrated in Table 8. Melt viscosity of the resulting polyimide composition was measured by extruding under load of 100 kg after maintaining at 360° C. for 5 minutes in the cylinder of the flow tester. Results are illustrated in Table 8.

EXAMPLES 94–96, COMPARATIVE EXAMPLE 17

Polyimide-11 and Bisimide Compound-12 were dry blended in proportions illustrated in Table 8. Melt viscosity of the resulting composition was measured by extruding under load of 100 kg after maintaining at 370° C. for 5 minutes in the cylinder of the flow tester. Results are illustrated in Table 8.

EXAMPLES 97–99, COMPARATIVE EXAMPLE 18

Polyimide-12 and Bisimide Compound-10 were dry blended in proportions illustrated in Table 8. Melt viscosity was measured by extruding under load of 100 kg after maintaining at 340° C. for 5 minutes in the cylinder of the flow tester. Results are illustrated in Table 8.

By the addition of bisimide, melt viscosity of the resin was remarkably decreased and processability was improved.

TABLE 8

| | Polyimide (wt. part) | | Bisimide (wt. part) | | Melt viscosity (poise) |
|---|---|---|---|---|---|
| Example 72 | Polyimide-7 | 100 | Bisimide Compound-1 | 1 | 7200 |
| Example 73 | | 100 | | 5 | 5000 |
| Example 74 | | 100 | | 10 | 3200 |
| Comparative Example 13 | | 100 | | 0 | 8500 |
| Example 75 | | 100 | Bisimide Compound-3 | 5 | 5400 |
| Example 76 | | 100 | | 15 | 2400 |
| Example 77 | | 100 | | 25 | 1000 |
| Example 78 | Polyimide-8 | 100 | Bisimide Compound-5 | 2 | 46000 |
| Example 79 | | 100 | | 10 | 17000 |
| Example 80 | | 100 | | 30 | 1300 |
| Comparative Example 14 | | 100 | | 0 | 68000 |
| Example 81 | | 100 | Bisimide Compound-7 | 5 | 34000 |
| Example 82 | | 100 | | 15 | 8000 |
| Example 83 | | 100 | | 30 | 1000 |
| Example 84 | Polyimide-9 | 100 | Bisimide Compound-1 | 10 | 4200 |
| Example 85 | | 100 | | 30 | 700 |
| Example 86 | | 100 | | 60 | **<100 |
| Comparative Example 15 | | 100 | | 0 | 10000 |
| Example 87 | | 100 | Bisimide Compound-8 | 5 | 5400 |
| Example 88 | | 100 | | 10 | 3600 |
| Example 89 | | 100 | | 20 | 1500 |
| Example 90 | Polyimide-10 | 100 | Bisimide Compound-9 | 2 | 5000 |
| Example 91 | | 100 | | 5 | 3400 |
| Comparative Example 16 | | 100 | | 0 | 6000 |
| Example 92 | | 100 | Bisimide Compound-11 | 10 | 2200 |
| Example 93 | | 100 | | 15 | 1200 |
| Example 94 | Polyimide-11 | 100 | Bisimide Compound-12 | 10 | 3000 |
| Example 95 | | 100 | | 30 | 300 |
| Example 96 | | 100 | | 50 | **<100 |
| Comparative Example 17 | | 100 | | 0 | 9500 |
| Example 97 | Polyimide-12 | 100 | Bisimide Compound-10 | 2 | 4000 |
| Example 98 | | 100 | | 5 | 2800 |
| Example 99 | | 100 | | 10 | 1400 |
| Comparative Example 18 | | 100 | | 0 | 5500 |

EXAMPLES 100–102

The bisimide compound which was prepared by reacting 4,4'-bis(3-aminophenoxy)biphenyl with phthalic anhydride according to Example 1 and had an inherent viscosity of 0.52 dl/g, glass transition temperature of 250° C. and melting point of 298° C. (hereinafter referred to simply as Bisimide-A) was used as a raw material. A bisimide solution compound of 20% by weight of Bisimide-A, 40% by weight of dichloromethane and 40% by weight of 1,1,2-trichloroethane was prepared.

An oxidation-treated acrylic carbon fiber roving, HTA(Trade mark of Toho Rayon Co.; used as carbon fiber in the below examples and comparative examples, unless otherwise noted) was continuously immersed in the bisimide solution at a rate of 60 m/hr, dried to remove the solvents and cut into a length of 3 mm to obtain chopped strand. The adhered amount of the bisimide was 5% by weight for the weight of the carbon fiber. The carbon fiber chopped strand thus obtained was dry blended with Polyimide-4 in proportions illustrated in Table 9. The resin composition thus obtained was fed to an extruder having a bore diameter of 40 mm, melt-kneaded at 400° C. and extruded to obtain uniformly blended pellets.

The above uniform pellets were injection molded with a common injection molding machine at a cylinder temperature of 410° C. and mold temperature of 200° C. to form dumbbell specimens. Tensile strength of the dumbbell specimens was measured at 23° C. at a pulling rate of 5 mm/min. Results are illustrated in Table 9.

COMPARATIVE EXAMPLES 19–20

The same procedures as conducted in Examples 100–102 were carried out except that the carbon fiber chopped strand coated with the bisimide compound was replaced by an epoxyresin collected acrylic carbon fiber. Dumbbell specimens of carbon fiber reinforced polyimide resin thus prepared were subjected to tensile strength test and results are illustrated in Table 9.

TABLE 9

| | Composition | | | | Tensile strength (kg/cm$^2$) |
|---|---|---|---|---|---|
| | Polyimide resin | | Carbon fiber | | |
| | Kind of resin | Amount (wt. %) | Collecting agent | Amount (wt. %) | |
| Example 100 | Polyimide-4 | 80 | Bisimide A | 20 | 2610 |
| Example 101 | | 70 | | 30 | 3060 |
| Example 102 | | 60 | | 40 | 3400 |
| Comparative Example | Polyimide-4 | 80 | epoxy resin | 20 | 1880 |

TABLE 9-continued

| | Polyimide resin | | Carbon fiber | | Tensile |
|---|---|---|---|---|---|
| | Kind of resin | Amount (wt. %) | Collect-ing agent | Amount (wt. %) | strength (kg/cm²) |
| Example 20 | | 70 | | 30 | 2060 |
| Example 21 | | 60 | | 40 | 2200 |

EXAMPLES 103–105

The bisimide compound which was prepared by reacting bis[4-(3-aminophenoxy)phenyl]sulfide with phthalic anhydride according to Example 3 and had a melting point of 230° C. (hereinafter referred to simply as Bisimide-B) was used as a raw material.

As oxidation-treated carbon fiber roving was continuously immersed in molten Bisimide-B at 240° C. at a rate of 30 m/hr and cut into a length of 3 mm to obtain chopped strand. The amount of adhered bisimide compound was 7% by weight for the weight of carbon fiber.

The carbon fiber chopped strand thus obtained was dry blended with Polyimide-5 in proportions illustrated in Table 10. The resin composition obtained was fed to an extruder having a bore diameter of 40 mm, melt-kneaded at 360° C. and extruded to obtain uniformly blended pellets.

The above uniform pellets were injection molded with a common injection molding machine at a cylinder temperature of 360° C. and mold temperature of 180° C. to form dumbbell specimens. Tensile strength of the dumbbell specimens was measured at 23° C. at a pulling rate of 5 mm/min. Results are illustrated in Table 10.

COMPARATIVE EXAMPLES 22–23

The same procedures as conducted in Examples 102–104 were carried out except that proportions of the bisimide coated carbon fiber were changed. Results are illustrated in Table 10. Pellets containing 60% by weight of carbon fiber had poor melt flowability and hence dumbbell specimens could not be prepared by injection molding.

TABLE 10

| | Polyimide resin | | Carbon fiber | | Tensile |
|---|---|---|---|---|---|
| | Kind of resin | Amount (wt. %) | Collect-ing agent | Amount (wt. %) | strength (kg/cm²) |
| Example 103 | Polyimide-5 | 80 | Bisimide-B | 20 | 2970 |
| Example 104 | | 70 | | 30 | 3450 |
| Example 105 | | 60 | | 40 | 3880 |
| Comparative Example 22 | Polyimide-5 | 40 | epoxy resin | 60 | molding impossible |
| Example 23 | | 98 | | 20 | 1650 |

TABLE 10-continued

| | Polyimide resin | | Carbon fiber | | Tensile |
|---|---|---|---|---|---|
| | Kind of resin | Amount (wt. %) | Collect-ing agent | Amount (wt. %) | strength (kg/cm²) |

EXAMPLES 106–108

The same procedures as conducted in Examples 100–102 were carried out except that Polyimide-4 was replaced by Polyimide-6 and the composition was melt-kneaded at 320° C. to obtain uniformly blended pellets. The pellets thus obtained was injection molded with a common injection molding machine at a cylinder temperature of 330° C. and mold temperature of 160° C. to prepare dumbbell specimens. Tensile strength of the dumbbell specimens was measured at 23° C. at a pulling rate of 5 mm/min. Results are illustrated in Table 11.

COMPARATIVE EXAMPLE 24

Dumbbell specimens were prepared by carrying out the same procedures as conducted in Examples 106–108 except that the polyimide resin was used alone without carbon fiber. Results are illustrated in Table 11.

TABLE 11

| | Polyimide resin | | Carbon fiber | | Tensile |
|---|---|---|---|---|---|
| | Kind of resin | Amount (wt. %) | Collect-ing agent | Amount (wt. %) | strength (kg/cm²) |
| Example 106 | Polyimide-6 | 80 | Bisimide-A | 20 | 2600 |
| Example 107 | | 70 | | 30 | 2910 |
| Example 108 | | 60 | | 40 | 3260 |
| Comparative Example 24 | Polyimide-6 | 100 | Bisimide-A | 0 | 1180 |

EXAMPLES 109–111

Uniformly blended pellets were prepared by carrying out the same procedures as conducted in Examples 106–108 except that Polyimide-6 is replaced by polyimide-1 and the composition was melt-kneaded at 360° C.

Dumbbell specimens were prepared from the uniformly blended pellets by injection molding at a cylinder temperature of 380° C. and mold temperature 180° C. Tensile strength of the specimens was measured at 23° C. at a pulling rate of 5 mm/min. Results are illustrated in Table 12.

COMPARATIVE EXAMPLE 25–27

Dumbbell specimens of carbon fiber reinforced polyimide resin were prepared by carrying out the same procedures as conducted in Examples 109–111 except that the carbon fiber chopped strand coated with the bisimide compound was replaced by an acrylic carbon fiber collected with an epoxy resin. Tensile strength of the specimens was measured under the same conditions as in Examples 109–111 and results are illustrated in Table 12.

TABLE 12

| | Composition | | | | Tensile strength (kg/cm$^2$) |
|---|---|---|---|---|---|
| | Polyimide resin | | Carbon fiber | | |
| | Kind of resin | Amount (wt. %) | Collecting agent | Amount (wt. %) | |
| Example 109 | Polyimide-1 | 80 | Bisimide-A | 20 | 2680 |
| Example 110 | | 70 | | 30 | 3120 |
| Example 111 | | 60 | | 40 | 3510 |
| Comparative Example 25 | Polyimide-1 | 80 | epoxy resin | 20 | 1930 |
| Example 26 | | 70 | | 30 | 2100 |
| Example 27 | | 60 | | 40 | 2270 |

EXAMPLES 112–114

A bisimide solution composed of 40% by weight of dichloromethane, 40% by weight of 1,1,2-trichloroethane and 20% by weight of Bisimide Compound-3(hereinafter referred to simply as Bisimide-C) was prepared. An oxidation-treated acrylic carbon fiber roving, HTA(Trade Mark of Toho Rayon Co.) was continuously immersed in the bisimide solution at a rate of 60 m/hr, dried to remove the solvents and cut into a length of 3 mm to obtain chopped strand. The adhered amount of the bisimide was 5% by weight for the weight of the carbon fiber.

The carbon fiber chopped strand thus obtained was dry blended with polyimide-4 in proportions illustrated in Table 13. The resin composition thus obtained was fed to an extruder having a bore diameter of 40 mm, melt-kneaded at 400° C. and extruded to obtain uniformly blended pellets.

The above uniform pellets were injection molded with a common injection molding machine at a cylinder temperature of 400° C. and mold temperature of 200° C. to form dumbbell specimens. Tensile strength of the dumbbell specimens was measured at 23° C. at a pulling rate of 5 mm/min. Results are illustrated in Table 13.

COMPARATIVE EXAMPLES 28–30

The same procedures as conducted in Examples 112–114 were carried out except that the carbon fiber chopped strand coated with the bisimide compound was replaced by an epoxy-resin collected acrylic carbon fiber. Dumbbell specimens of carbon fiber reinforced polyimide resin thus prepared were subjected to tensile strength test and results are illustrated in Table 13.

TABLE 13

| | Composition | | | | Tensile strength (kg/cm$^2$) |
|---|---|---|---|---|---|
| | Polyimide resin | | Carbon fiber | | |
| | Kind of resin | Amount (wt. %) | Collecting agent | Amount (wt. %) | |
| Example 112 | Polyimide-4 | 80 | Bisimide-C | 20 | 2630 |
| Example 113 | | 70 | | 30 | 3080 |
| Example 114 | | 60 | | 40 | 3430 |
| Comparative Example 28 | Polyimide-4 | 80 | epoxy resin | 20 | 1880 |
| Example 29 | | 70 | | 30 | 2060 |
| Example 30 | | 60 | | 40 | 2200 |

EXAMPLES 115–117

A carbon fiber roving which was previously oxidation-treated on the surface was continuously immersed in molten Bisimide-C at a rate of 30 m/hr and cut into a length of 3 mm to obtain chopped strand.

The adhered amount of the bisimide was 5% by weight for the weight of the carbon fiber.

The carbon fiber chopped strand thus obtained was dry blended with polyimide-5 in proportions illustrated in Table 14. The resin composition thus obtained was fed to an extruder having a bore diameter of 40 mm, melt-kneaded at 360° C. and extruded to obtain uniformly blended pellets.

The above uniform pellets were injection molded with a common injection molding machine at a cylinder temperature of 360° C. and mold temperature of 180° C. to form dumbbell specimens. Tensile strength of the dumbbell specimens was measured at 23° C. at a pulling rate of 5 mm/min. Results are illustrated in Table 14.

COMPARATIVE EXAMPLES 31–32

The same procedures as conducted in Examples 115–117 were carried out except that the proportion of the polyimide to the carbon fiber coated with the bisimide was changed. Results are illustrated in Table 14.

The pellets containing 60% by weight of carbon fiber had poor melt flowability and hence dumbbell specimens could not be prepared by injection molding.

TABLE 14

| | Composition | | | | Tensile strength (kg/cm$^2$) |
|---|---|---|---|---|---|
| | Polyimide resin | | Carbon fiber | | |
| | Kind of resin | Amount (wt. %) | Collecting agent | Amount (wt. %) | |
| Example 115 | Polyimide-5 | 80 | Bisimide-C | 20 | 2980 |
| Example 116 | | 70 | | 30 | 3500 |
| Example | | 60 | | 40 | 3950 |

TABLE 14-continued

| | Composition | | | | |
|---|---|---|---|---|---|
| | Polyimide resin | | Carbon fiber | | Tensile |
| | Kind of resin | Amount (wt. %) | Collect- ing agent | Amount (wt. %) | strength (kg/cm²) |
| 117 Comparative Example 31 | Polyimide -5 | 40 | Bisimide -C | 60 | molding impossible |
| Example 32 | | 98 | | 2 | 1650 |

EXAMPLES 118–120

Uniformly blended pellets were prepared by carrying out the same procedures as conducted in Examples 112–114 except that Polyimide-4 is replaced by Polyimide-6 and melt-kneading was carried out at 320° C. The uniform pellets obtained were injection molded with a common injection molding machine at a cylinder temperature of 320° C. and mold temperature of 160° C. to prepare dumbbell specimens. Tensile strength of the specimens was measured at 23° C. at a pulling rate of 5 mm/min. Results are illustrated in Table 15.

COMPARATIVE EXAMPLE 33

Dumbbell specimens were prepared by carrying out the same procedures as conducted in Examples 118–120 except that polyimide resin was used alone without carbon fiber. Results are illustrated in Table 15.

TABLE 15

| | Composition | | | | |
|---|---|---|---|---|---|
| | Polyimide resin | | Carbon fiber | | Tensile |
| | Kind of resin | Amount (wt. %) | Collect- ing agent | Amount (wt. %) | strength (kg/cm²) |
| Example 118 | Polyimide -6 | 80 | Bisimide -C | 20 | 2630 |
| Example 119 | | 70 | | 30 | 3000 |
| Example 120 | | 60 | | 40 | 3320 |
| Comparative Example 33 | Polyimide -6 | 100 | Bisimide -C | 0 | 1180 |

The polyimide resin composition of the present invention is a composition comprising an aromatic bisimide compound in polyimide resin and has improved processability.

The resin composition of the invention composed of an improved carbon fiber and polyimide resin can be processed into a desired shape by injection molding, extrusion forming, transfer molding, compression molding and other known processing methods.

The resin composition of the invention thus processed has excellent mechanical strength, particularly mechanical strengths at high temperatures, and hence can be used for mechanical members and automotive parts which require high mechanical strengths at high temperatures, for example, gear, cam, bushing, pulley and sleeve, and also for members of internal combustion engines, for example, gas exhaustingparts for a silencer such as an impeller and manifold of an integrated centrifugal compressor, valve guide, valve stem, piston skirt, oil pan, front cover and locker cover.

The carbon fiber reinforced polyimide resin composition of the invention is usually used in the form of pellets which can be handled with ease. Molded articles are prepared by injection molding. The pellets are prepared by kneading and extruding the polyimide resin and the carbon fiber strand with a known single or twin screw extruder and successively by cutting the resulting strand of the composition.

Injection molding of the pellets thus obtained is carried out with a common injection molding machine at a cylinder temperature of 360° to 420° C. and a mold temperature of 160° to 210° C., preferably 180° to 200° C. Complex shaped members of internal combustion engines such as an impeller of an integrated centrifugal compressor can also be prepared with ease.

The carbon fiber reinforced polyimide resin composition of the invention has excellent mechanical strength and can be widely used as a material for members of electric and electronic devices, automotive trim, space and aeronautical equipment and general instruments in industry. Thus, the polyimide resin composition is valuable in industry.

Further, the bisimide compound of the invention is very useful for the preparation of the polyimide resin composition having these excellent properties.

We claim:

1. A polyimide resin composition comprising a polyimide and a bisimide compound represented by the formula (1):

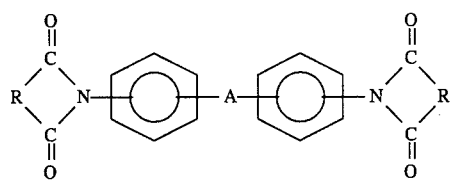

wherein A is a divalent radical selected from the group consisting of radicals having the formulas:

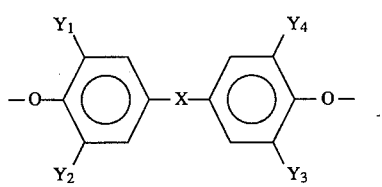

where X is a direct bond, a divalent bond, a divalent hydrocarbon radical having from 1 to 10 carbon atoms, hexafluorinated isopropylidene, carbonyl, thio or sulfonyl, and $Y_1$–$Y_4$ are individually hydrogen atom, methyl radical, methoxy radical, chlorine or bromine atom,

-continued

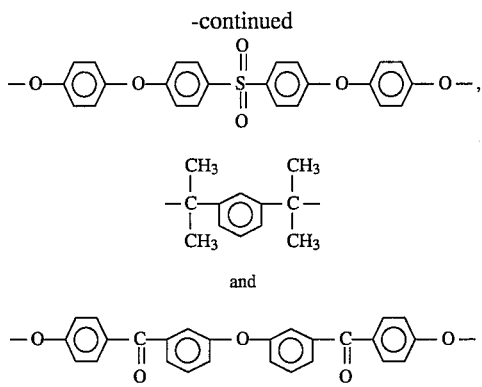

and and R is a divalent radical selected from the group consisting of a monoaromatic radical, condensed polyaromatic radical, and noncondensed aromatic radical connected to each other with a direct bond or a bridge member.

2. A polyimide resin composition comprising a polyimide having recurring structural units represented by the formula (9):

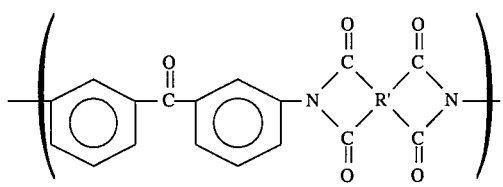

(9)

wherein R' is a tetravalent radical having 2 or more carbon atoms and selected from the group consisting of an aliphatic radical, alicyclic radical, monoaromatic radical, condensed polyaromatic radical and noncondensed aromatic radical connected to each other with a direct bond or a bridge member, and art aromatic bisimide compound represented by the formula (10):

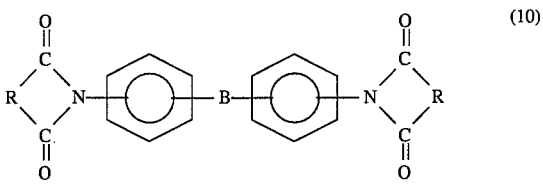

(10)

wherein B is a radical selected from a direct bond, divalent hydrocarbon radical having from 1 to 10 carbon atoms, hexafluorinated isopropylidene, carbonyl, thio, ether and sulfonyl, each nitrogen atom is individually para-, ortho- or meta-located to B and R is a divalent radical selected from the group consisting of a monoaromatic radical, condensed polyaromatic radical, noncondensed aromatic radical connected to each other with a direct bond or a bridge member, and/or by the formula (2):

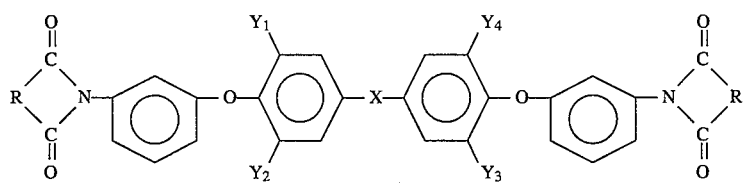

(2)

wherein X is a direct bond, a divalent hydrocarbon radical having from 1 to 10 carbon atoms, hexafluorinated isopropylidene, carbonyl, thio or sulfonyl, and $Y_1$–$Y_4$ are individually hydrogen, methyl radical, methoxy radical, chlorine or bromine atom, and R is a divalent radical selected from the group consisting of a monoaromatic radical, condensed polyaromatic radical, and noncondensed aromatic radical connected to each other with a direct bond or a bridge member.

3. A polyimide resin composition comprising an aromatic bisimide compound represented by the formula (10):

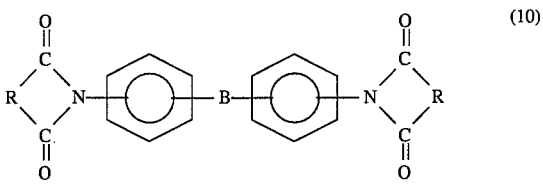

(10)

wherein B is a radical selected from a direct bond, divalent hydrocarbon radical having from 1 to 10 carbon atoms, hexafluorinated isopropylidene, carbonyl, thio, ether and sulfonyl, each nitrogen atom is individually para-, ortho- or meta-located to B and R is a divalent radical selected from the group consisting of a monoaromatic radical, condensed polyaromatic radical, noncondensed aromatic radical connected to each other with a direct bond or a bridge member, and/or by the formula (2):

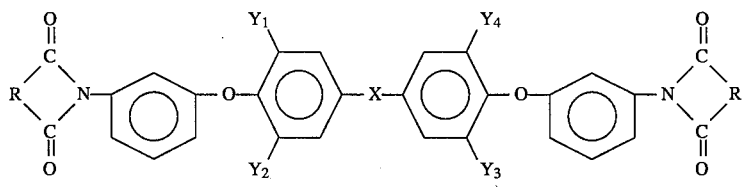

(2)

wherein X is a direct bond, a divalent hydrocarbon radical having from 1 to 10 carbon atoms, hexafluorinated isopropylidene, carbonyl, thio or sulfonyl, and $Y_1$–$Y_4$ are individually hydrogen, methyl radical, methoxy radical, chlorine or bromine atom, and R is a divalent radical selected from the group consisting of a monoaromatic radical, condensed polyaromatic radical, and noncondensed aromatic radical connected to each other with a direct bond or a bridge member; and the polyimide has recurring structural units represented by the formula (11):

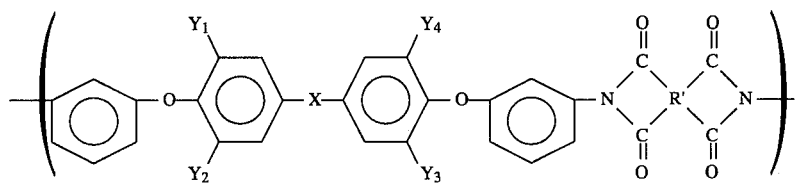

(11)

wherein X is a direct bond, a divalent hydrocarbon radical having from 1 to 10 carbon atoms, hexafluorinated isopropylidene, carbonyl, thio or sulfonyl, $Y_1$–$Y_4$ are individually hydrogen atom, methyl radical, methoxy radical, chlorine or bromine atom, and R' is a tetravalent radical having 2 or more carbon atoms and selected from the group consisting of an aliphatic radical, alicyclic radical, monoaromatic radical, condensed polyaromatic radical and noncondensed aromatic radical connected to each other with a direct bond or a bridge member.

4. A polyimide resin composition of claim 2 wherein the aromatic bisimide compound is represented by the formula (3):

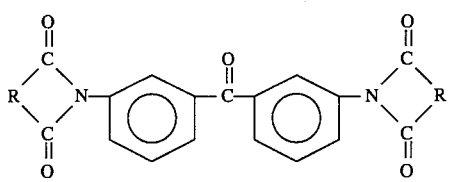

(3)

wherein R is the same as above.

5. A polyimide resin composition comprising a polyimide having recurring structural units of the formula (11):

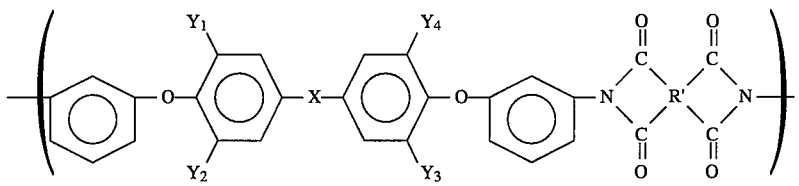

(11)

wherein X is a direct bond, a divalent hydrocarbon radical having from 1 to 10 carbon atoms, hexafluorinated isopropylidene, carbonyl, thio or sulfonyl, $Y_1$–$Y_4$ are individually hydrogen atom, methyl radical, methoxy radical, chlorine or bromine atom, and R' is a tetravalent radical having 2 or more carbon atoms and selected from the group consisting of an aliphatic radical,. alicyclic radical, monoaromatic radical, condensed polyaromatic radical and noncondensed aromatic radical connected to each other with a direct bond or a bridge member.

6. A polyimide resin composition of claim 5 wherein the aromatic bisimide compound is represented by the formula (7):

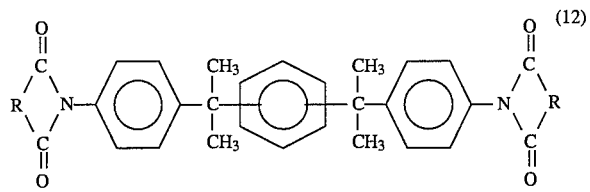

(12)

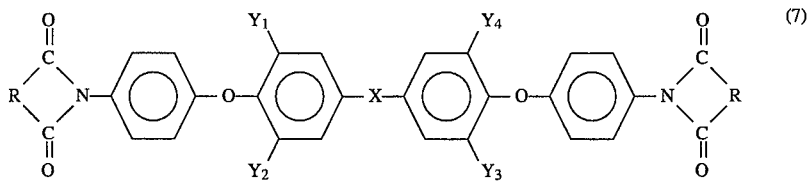

(7)

wherein X and $Y_1$–$Y_4$ are the same as above and R is a divalent radical selected from the grQUp consisting of a monoaromatic radical, condensed polyaromatic radical and noncondensed aromatic radical connected to each other with a direct bond or a bridge member.

7. A polyimide resin composition of claim 15 wherein the aromatic bisimide compound is represented by the formula(12):

wherein R is a divalent radical selected from the group consisting of a monoaromatic radical, condensed polyaromatic radical, and noncondensed aromatic radical connected to each other with a direct bond or a bridge member, and two isopropylidene radicals are located in para- or meta- position on a benzene ring.

8. A polyimide resin composition of claim 5 wherein the aromatic bisimide compound is represented by the formula (4):

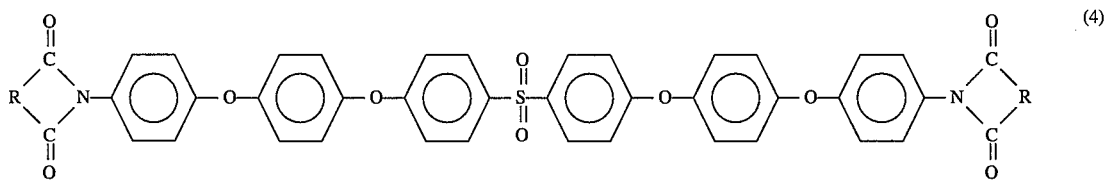

(4)

wherein R is a divalent radical selected from the group consisting of a monoaromatic radical, condensed polyaromatic radical and noncondensed aromatic radical connected to each other with a direct bond or a bridge member.

9. A polyimide resin composition of claim 5 wherein the aromatic bisimide compound is represented by the formula (13):

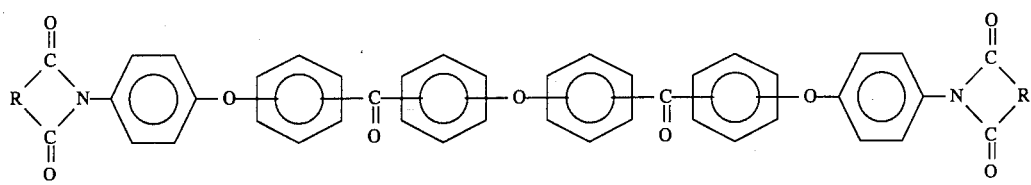

(13)

wherein R is a divalent radical selected from the group consisting of a monoaromatic radical, condensed polyaromatic radical and noncondensed aromatic radical connected to each other with a direct bond or a bridge member, and the two carbonyl radicals are located on meta- or para-position to the central ether bond, and the other two ether bonds on the outside are located on meta- or para-position to said carbonyl radicals, respectively.

10. A polyimide resin composition of claim 5 wherein the aromatic bisimide compound is represented by the formula(14):

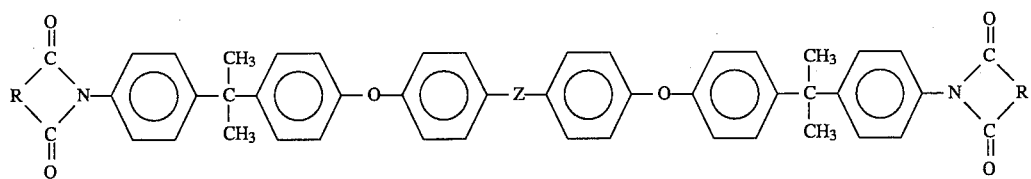

(14)

wherein Z is a radical selected from the group consisting of carbonyl or sulfonyl, and R is a divalent radical having 2 and more carbon atoms and selected from the group consisting of an aliphatic radical, alicyclic radical, monoaromatic radical, condensed polyaromatic radical and noncondensed aromatic radical connected to each other with a direct bond or a bridge member.

11. A polyimide resin composition of claim 5 wherein the aromatic bisimide compound is represented by the formula (15):

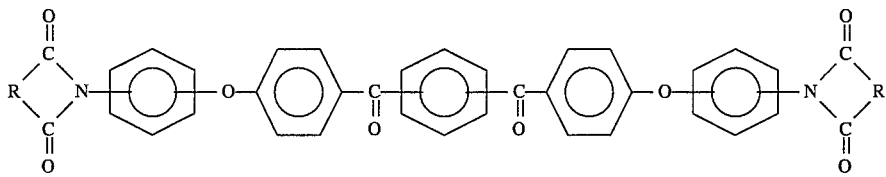

wherein R is a divalent radical selt from the group consisting of a monoaromatic radical, condensed polyaromatic radical and noncondensed aromatic radical connected to each other with a direct bond or a bridge member; the two carbonyl radicals are located on meta- or para-position on the central benzene ring; when the two carbonyl radicals are located on para-position on the central benzene ring, both temrinal nitrogen atoms are located on para- or recta-position to the ether linkages, respectively; and when the two carbonyl radicals are located on meta-position on the central benzene ring, both terminal nitrogen atoms are located on para- or meta-position to the ether linkages, respectively.

12. A polyimide resin composition of claim 5 wherein the aromatic bisimide compound is represented by the formula (16):

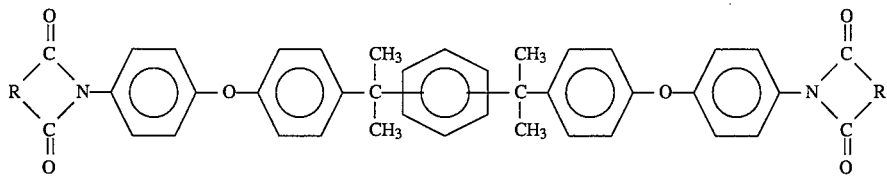

wherein R is a divalent radical selected from the group consisting of a monoaromatic radical, condensed polyaromatic radical and noncondensed aromatic radical connected to each other with a direct bond or a bridge member, and the two isopropylidene radicals are located on para- or meta-position on the central benzene ring.

13. A polyimide resin composition comprising a polyimide having recurring structural units represented by the formula (17):

connected to each other with a direct bond or a bridge member; and an aromatic bisimide compound.

14. A polyimide resin composition of claim 13 wherein the aromatic bisimide compound is represented by the formula (10):

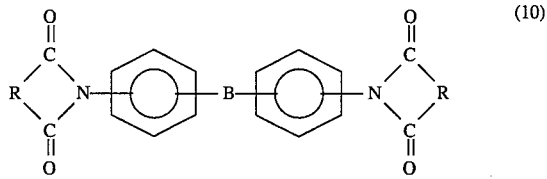

wherein B is a radical selected from a direct bond, divalent hydrocarbon radical having from 1 to 10 carbon atoms, hexafluorinated isopropylidene, carbonyl, thio, ether and sulfonyl, each nitrogen atom is individually para-, ortho- or meta-located to B and R is a divalent radical selected from the group consisting of a monoaromatic radical, condensed polyaromatic radical, noncondensed aromatic radical connected to each other with a direct bond or a bride member.

15. A polyimide resin composition of claim 13 wherein the aromatic bisimide compound is represented by the formula (2):

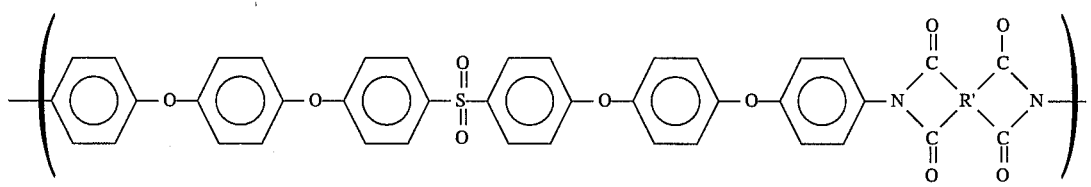

wherein R' is a tetravalent radical having 2 or more carbon atoms and selected from the group consisting of an aliphatic radical, alicyclic radical, monoaromatic radical, condensed polyaromatic radical and noncondensed aromatic radical

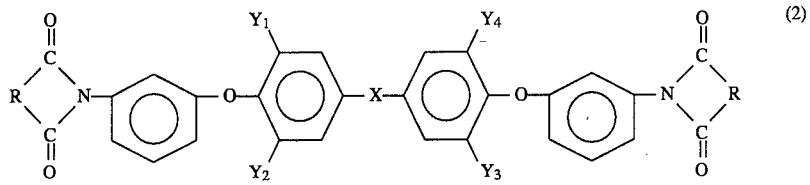

wherein X is a direct bond, a divalent hydrocarbon radical having from 1 to 10 Carbon atoms, hexafluorinated isopropylidene, carbonyl, thio or sulfonyl, and $Y_1$–$Y_4$ are individually hydrogen, methyl radical, methoxy radical, chlorine or bromine atom, and R is a divalent radical selected from the group consisting of a monoaromaticradical, condensed polyaromatic radical, and noncondensed aromatic radical connected to each other with a direct bond or a bridge member.

16. A polyimide resin composition of claim 13 wherein the aromatic bisimide compound is represented by the formula (7):

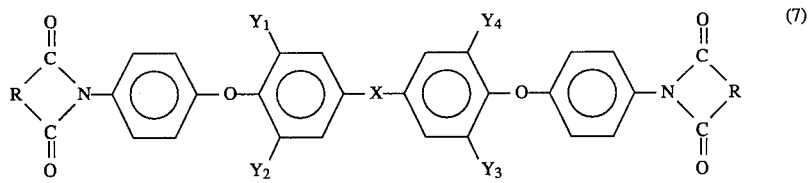

wherein X is a direct bond, a divalent hydrocarbon radical having from 1 to 10 carbon atoms, hexafluorinated isopropylidene, carbonyl, thio or sulfonyl, and $Y_1$–$Y_4$ are individually hydrogen, methyl radical, methoxy radical, chlorine or bromine atom, and R is a divalent radical selected from the group consisting of a monoaromatic radical, condensed polyaromatic radical, and noncondensed aromatic radical connected to each other with a direct bond or a bridge member.

17. A polyimide resin composition of claim 13 wherein the aromatic bisimide compound is represented by the formula (12):

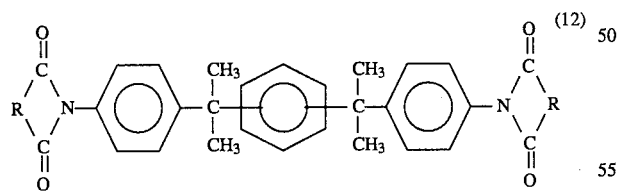

wherein R is a divalent radical selected from the group consisting of a monoaromatic radical, condensed. polyaromatic radical, and noncondensed aromatic radical connected to each other with a direct bond or a bridge member, and two isopropylidene radicals are located each other in para- or meta-position on a benzene ring.

18. A polyimide resin composition of claim 13 wherein the aromatic bisimide compound is represented by the formula (4):

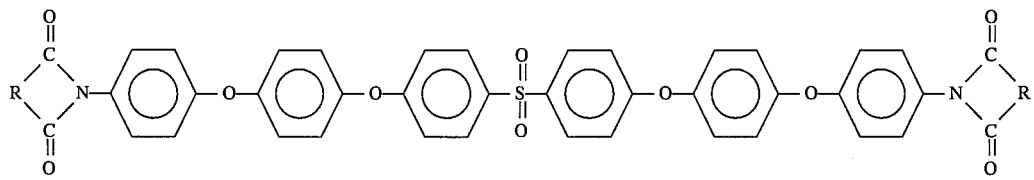

(4)

wherein R is a divalent radical selected from the group consisting of a monoaromatic radical, condensed polyaromatic radical and noncondensed aromatic radical connected to each other with a direct bond or a bridge member.

19. A polyimide resin composition of claim 13 wherein the aromatic bisimide compound is represented by the formula (13):

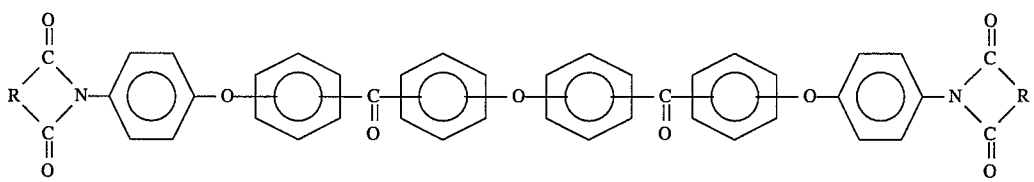

(13)

wherein R is a divalent radical selected from the group consisting of a monoaromatic radical, condensed polyaromatic radical and noncondensed aromatic radical connected to each other with a direct bond or a bridge member,. and the two carbonyl radicals are located on meta- or pa.ra-position to the central ether bond, and other two ether bonds on the outside are located on meta- or .para-position to said carbonyl radicals, respectively.

20. A polyimide resin composition of claim 13 wherein the aromatic bisimide compound is represented by the formula (14):

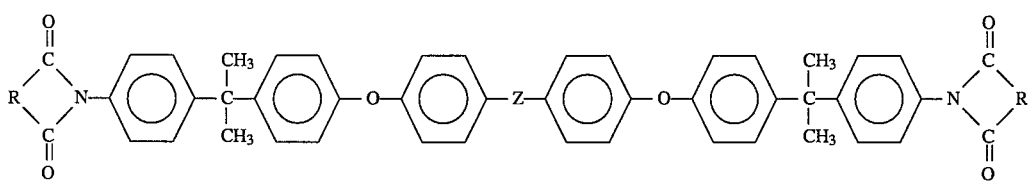

(14)

wherein Z is a radical selected from the group consisting of carbonyl and sulfonyl, and R is a divalent radical having 2 or more carbon atoms and selected from the group consisting of an aliphatic radical, alicyclic radical, monoaromatic radical, condensed polyaromatic radical and noncondensed aromatic radical connected to each other with a direct bond or a bridge member.

21. A polyimide resin composition of claim 13 wherein the aromatic bisimide compound is represented by the formula (15):

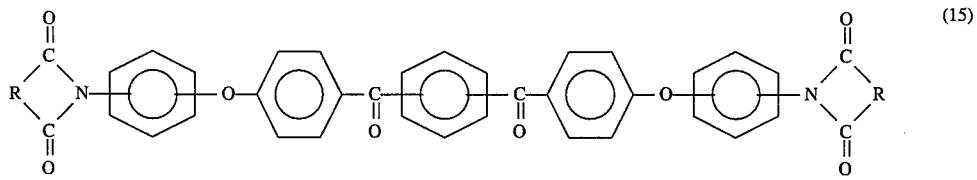

(15)

wherein R is a divalent radical selected from the group consisting of a monoaromatic radical, condensedpolyaromatic radical, and noncondensed aromatic radical connected to each other with a direct bond or a bridge member, and two isopropylidene radicals are located each other in .para- or meta-position on a benzene ring.

22. A polyimide resin composition of claim 13 wherein the aromatic bisimide compound is represented by the formula (16):

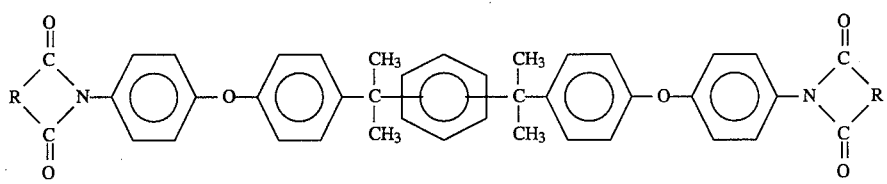

(16)

wherein R is a divalent radical selected from the group consisting of a monoaromatic radical, condensed polyaromatic radical and noncondensed aromatic radical connected to each other with a direct bond or a bridge member, and the two isopropylidene radicals are located on meta- or para-position to the central benzene ring.

* * * * *

UNITED STATES PATENT AND TRADEMARK OFFICE
CERTIFICATE OF CORRECTION

PATENT NO. : 5,457,154  
DATED : Oct. 10, 1995  
INVENTOR(S) : Masahiro Ohta, et al Page 1 of 2

It is certified that error appears in the above-indentified patent and that said Letters Patent is hereby corrected as shown below:

On title page, item [86], PCT No. to read –PCT/JP92/0039.

Column 71,

Claim 5, line 18, after "radical" delete "..." and insert -- , --; and  
line 21, after "member" insert --and an aromatic bisimide compound--.

Claim 6, line 36, delete "grOUp" and insert therefor --group--.

Claim 7, line 42, delete "15" and insert therefor --5--.  
Column 75,  
Claim 11, line 17, delete "temrinal" and insert therefor --terminal--; and  
line 18, delete "recta" and insert therefor --meta--.  
Column 76,  
Claim 14, line 42, delete "bride" and insert therefor --bridge--.  
Column 77,  
Claim 15, line 12, delete "Carbon" and insert therefor --carbon--.  
line 16, delete "monoaromaticradical" and insert therefor --monoaromatic radical--.  
Column 79,  
Claim 19, line 31, after "member," delete ".";  
line 32, delete "pa.ra" and insert therefor --para--; and  
line 34, before "para" delete ".".

UNITED STATES PATENT AND TRADEMARK OFFICE
CERTIFICATE OF CORRECTION

PATENT NO. : 5,457,154
DATED : Oct. 10, 1995
INVENTOR(S) : Masahiro Ohta, et al

It is certified that error appears in the above-indentified patent and that said Letters Patent is hereby corrected as shown below:

Claim 21, column 81, lines 2 and 3, delete "condensedpolyaromatic" and insert therefor --condensed polyaromatic--; and
column 81, line 5, before "para" delete ".".

Signed and Sealed this

Fifth Day of November, 1996

*Attest:*

BRUCE LEHMAN

*Attesting Officer*        Commissioner of Patents and Trademarks